(12) United States Patent
Jones et al.

(10) Patent No.: US 11,132,055 B2
(45) Date of Patent: Sep. 28, 2021

(54) ENHANCING THE PERFORMANCE OF NEAR-TO-EYE VISION SYSTEMS

(71) Applicants: Frank Jones, Carp (CA); James Benson Bacque, Ottawa (CA); Mark Harris, Woodlawn (CA)

(72) Inventors: Frank Jones, Carp (CA); James Benson Bacque, Ottawa (CA); Mark Harris, Woodlawn (CA)

(73) Assignee: eSight Corp., Kanata (CA)

( * ) Notice: Subject to any disclaimer, the term of this patent is extended or adjusted under 35 U.S.C. 154(b) by 0 days.

(21) Appl. No.: 16/207,660

(22) Filed: Dec. 3, 2018

(65) Prior Publication Data

US 2019/0179409 A1 Jun. 13, 2019

Related U.S. Application Data

(60) Provisional application No. 62/593,999, filed on Dec. 3, 2017.

(51) Int. Cl.
*G06F 3/01* (2006.01)
*G02B 27/01* (2006.01)
*G02B 27/00* (2006.01)
*G02B 5/04* (2006.01)

(52) U.S. Cl.
CPC ......... *G06F 3/013* (2013.01); *G02B 27/0093* (2013.01); *G02B 27/0172* (2013.01); *G02B 27/0176* (2013.01); *G02B 5/04* (2013.01); *G02B 2027/0138* (2013.01); *G02B 2027/0156* (2013.01); *G02B 2027/0178* (2013.01); *G02B 2027/0187* (2013.01)

(58) Field of Classification Search
None
See application file for complete search history.

(56) References Cited

U.S. PATENT DOCUMENTS

| | | | | |
|---|---|---|---|---|
| 2012/0119978 A1* | 5/2012 | Border | ............... | G02B 27/0172 345/8 |
| 2014/0375790 A1* | 12/2014 | Robbins | ............... | G02B 27/017 348/78 |
| 2015/0355481 A1* | 12/2015 | Hilkes | .................... | G02C 5/124 351/204 |
| 2016/0262608 A1* | 9/2016 | Krueger | ................ | G06T 19/006 |
| 2018/0133431 A1* | 5/2018 | Malchano | ............ | A61N 5/0622 |

* cited by examiner

*Primary Examiner* — Ifedayo B Iluyomade
(74) *Attorney, Agent, or Firm* — Rosenberg, Klein & Lee

(57) ABSTRACT

The majority of applications for head mounted display (HMD) users, irrespective of whether they are for short-term, long-term, low vision, augmented reality, etc. yield a conflicting set of tradeoffs between user comfort and minimal fatigue and strain during use, ease of attachment, minimizing intrusiveness and aesthetics which must be concurrently balanced with and are often in conflict with providing an optical vision system that provides the user with a wide field of view and high image resolution whilst also offering a large exit pupil for eye placement with sufficient eye clearance. Further, individual users' needs vary as do their needs with the general task at-hand, visual focus, and various regions-of-interest within their field of view. To address these issues, it is necessary to provide a high performance optical system, eyepiece design, and system features which overcome these limitations.

19 Claims, 40 Drawing Sheets

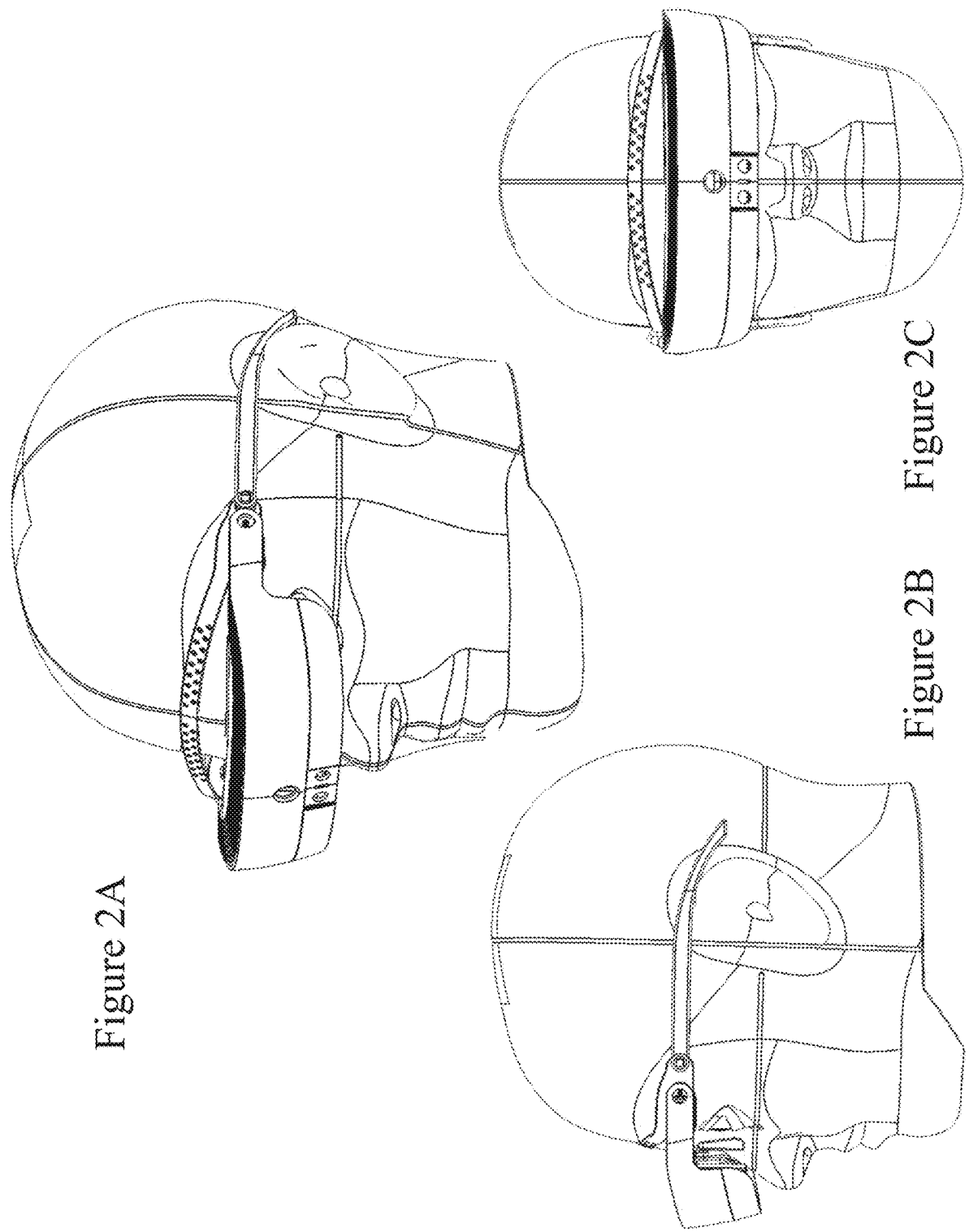

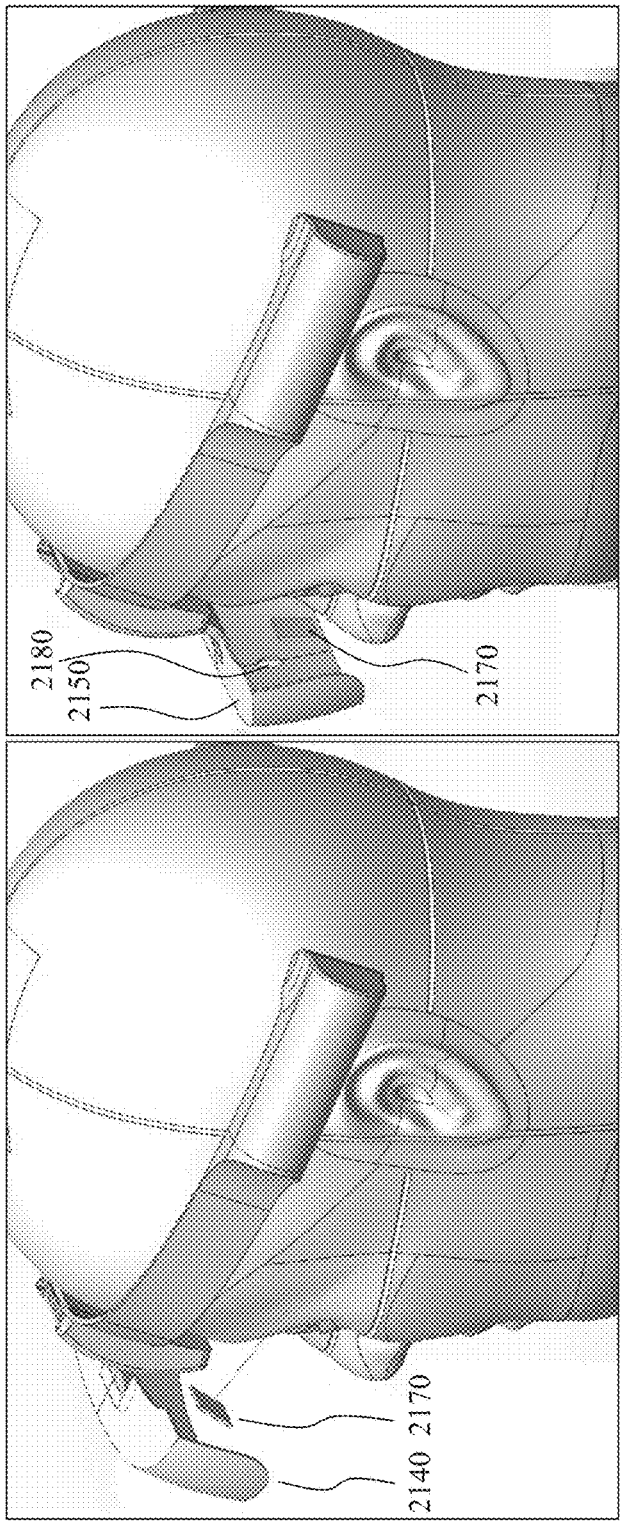
Figure 2N
Figure 2O
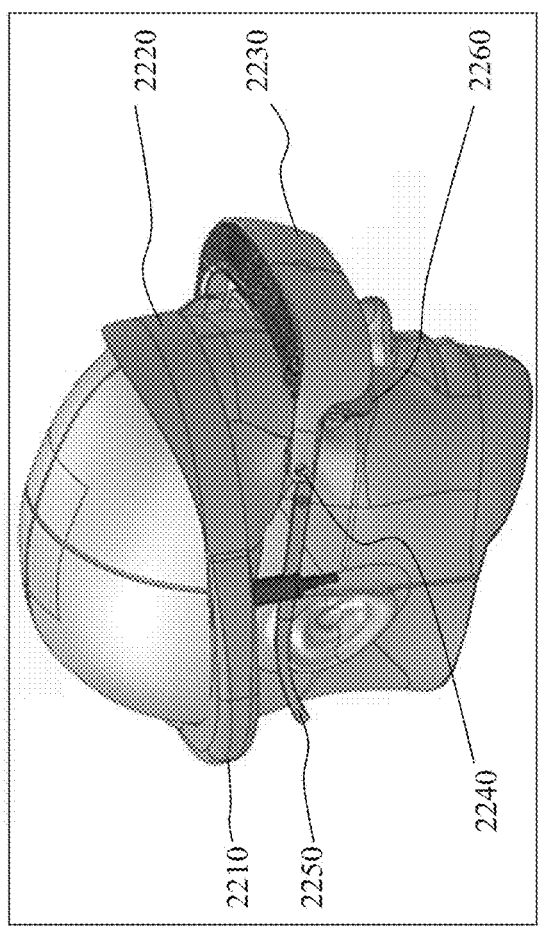
Figure 2P

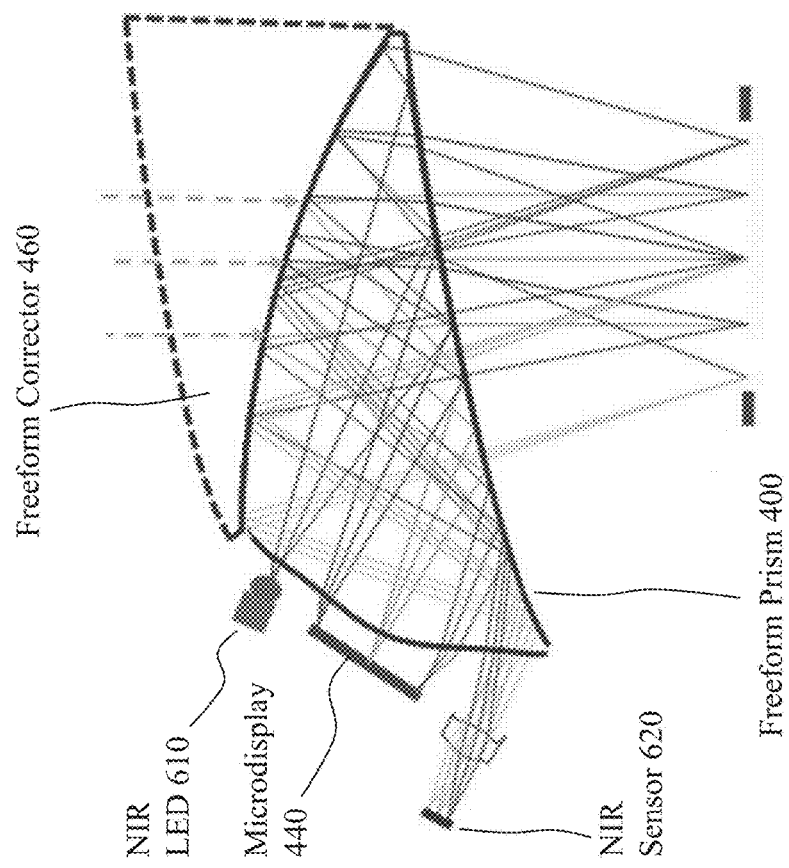
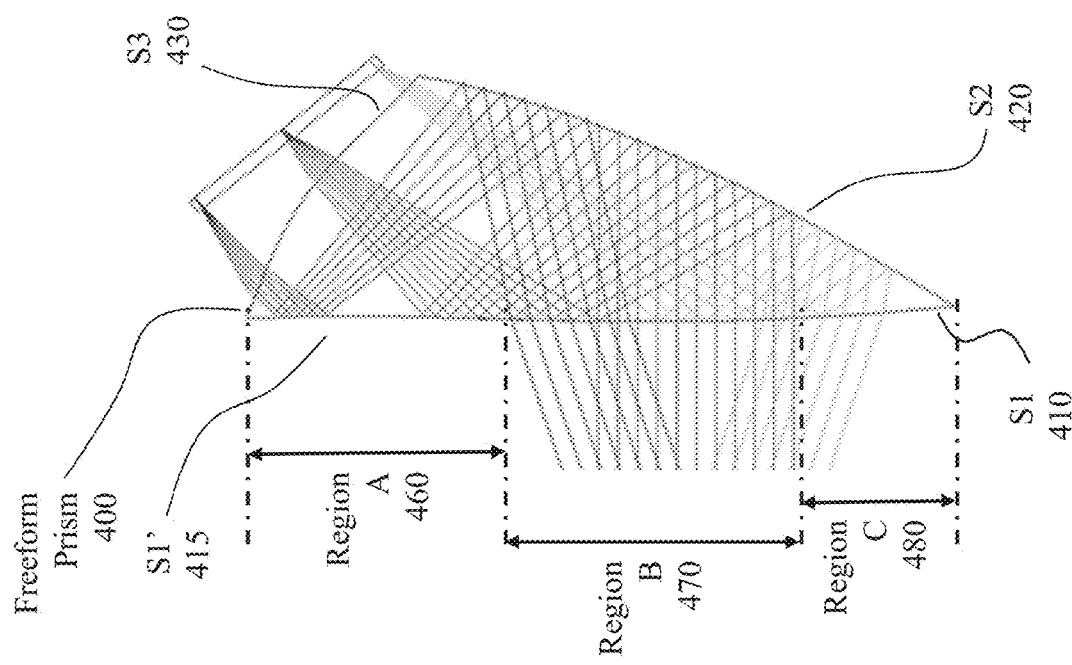
Figure 6
Figure 5

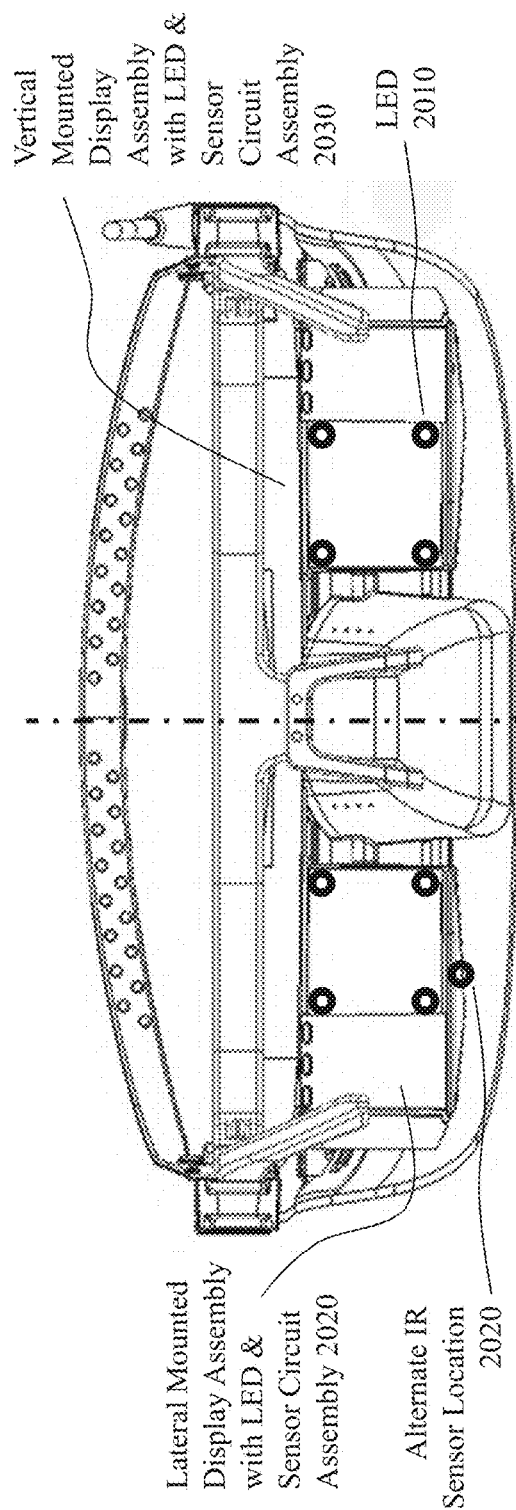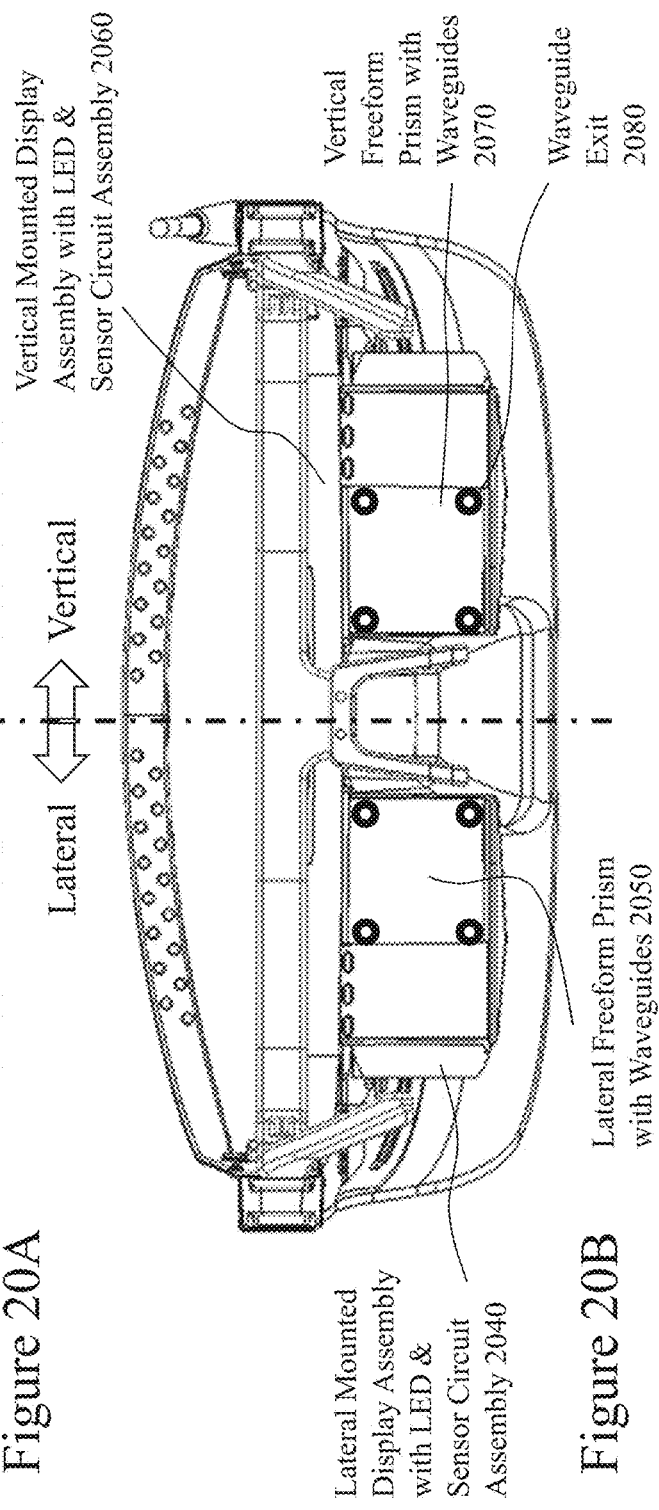
Figure 20A
Figure 20B

```
//Without dynamic IPD adjust, but performing separate distortion maps for R, G, B
// to allow for digital pre-compensation of chromatic aberration uniform sampler2D uSampler;
in vec2 vTexCoordRed;
in vec2 vTexCoordGreen;
in vec2 vTexCoordBlue;
out vec4 Color;
void main() {
Color.r = texture(uSampler, vTexCoordRed).r;
Color.g = texture(uSampler, vTexCoordGreen).g;
Color.b = texture(uSampler, vTexCoordBlue).b;
Color.a = 1.0;
};
```

Figure 21

```
//With dynamic IPD vergence adjust, and also performing separate distortion maps for R, G, B
// to allow for digital pre-compensation of chromatic aberration uniform sampler2D uSampler;
uniform float uXShift;
in vec2 vTexCoordRed;
in vec2 vTexCoordGreen;
in vec2 vTexCoordBlue;
out vec4 Color;
void main() {
if(vTexCoordRed.x+uXShift > 0.0f && vTexCoordRed.x+uXShift < 1.0f){
Color.r = texture(uSampler, vTexCoordRed + vec2(uXShift,0.0f)).r;
Color.g = texture(uSampler, vTexCoordGreen + vec2(uXShift,0.0f)).g;
Color.b = texture(uSampler, vTexCoordBlue + vec2(uXShift,0.0f)).b;
Color.a = 1.0;
}else{
Color = vec4(0.0f,0.0f,0.0f,1.0f);
}
};
```

Figure 22

```
//Configuration initialization
//Training mode detection – process
//Detect trigger change, assign mode change and perform {obtain userID
 retrieve configuration settings for NR2I-HMD
 configure dynamic image processing settings
 configure algorithms
 configure modes
 establish trigger conditions for configuration changes
 establish trigger conditions for mode changes
 If training=="N" then
         configure training
     else
         configure finish
END
If mode-trigger-detect=="Y" then
     select mode(trigger-change, trigger)
     accept-user
END
```

Figure 23

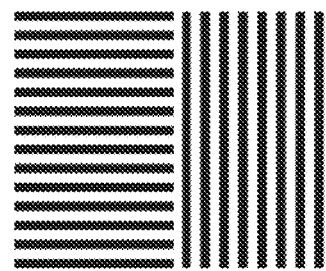
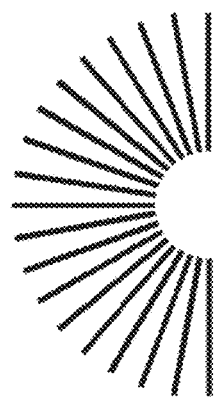
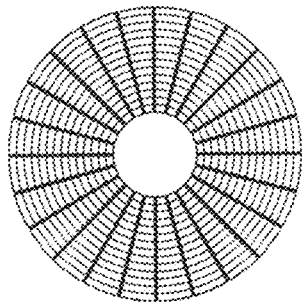
Figure 30
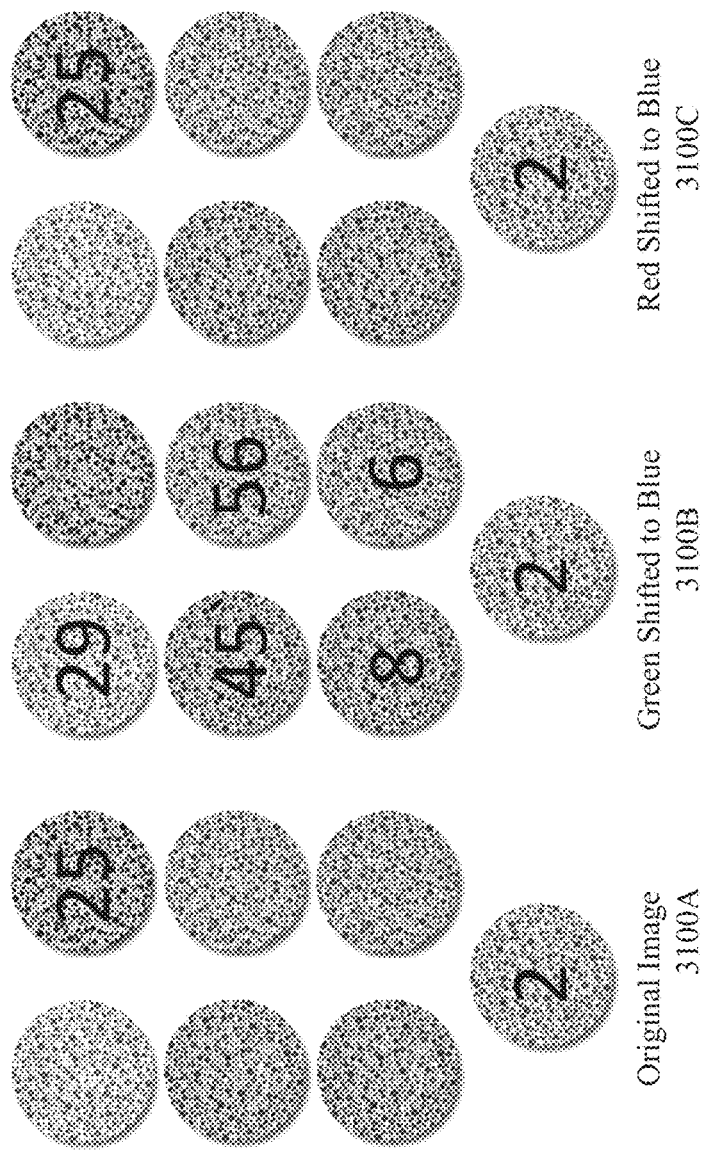
Figure 31

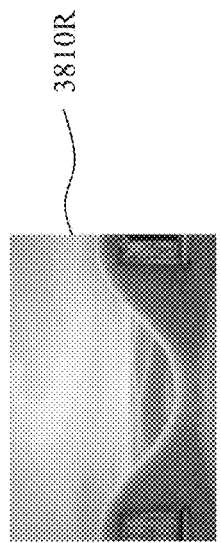
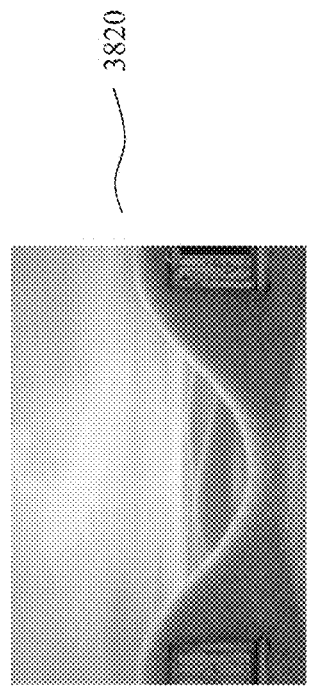
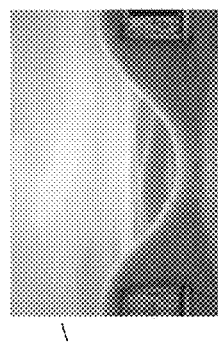
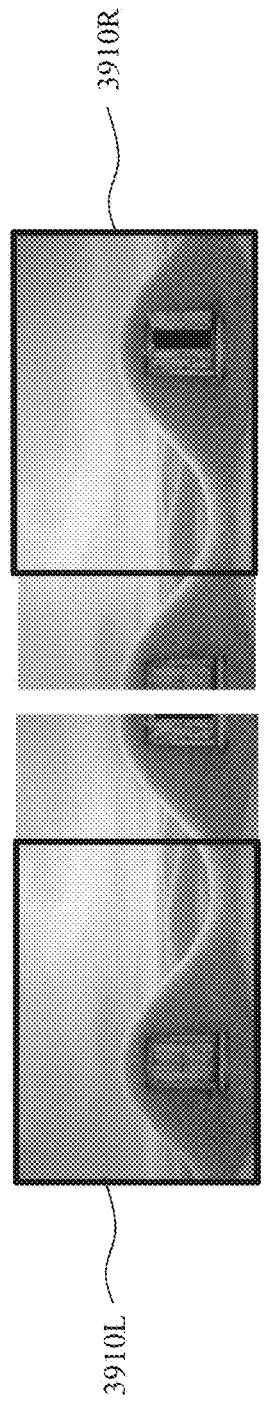
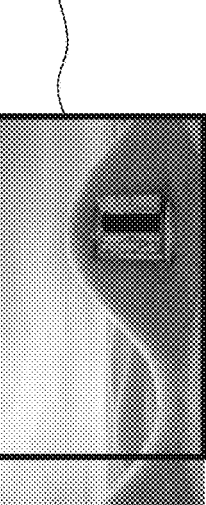
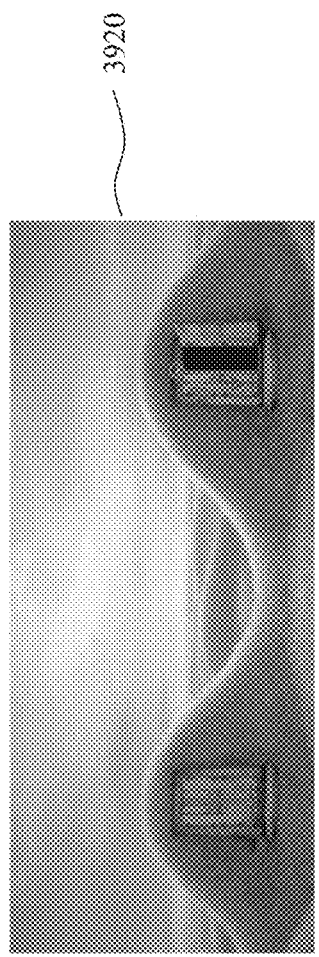
Figure 38
Figure 39

ENHANCING THE PERFORMANCE OF NEAR-TO-EYE VISION SYSTEMS

CROSS-REFERENCE TO RELATED APPLICATIONS

This application claims priority from U.S. Provisional Patent Application 62/593,999 filed Dec. 3, 2017 entitled "Enhancing the Performance of Near-to-Eye Vision Systems", the entire contents of which are incorporated herein by reference.

FIELD OF THE INVENTION

This invention relates to wearable NR2I vision systems and more particularly to providing wearable NR2I vision systems with wide field of view, high image resolution, low latency, large exit pupil for eye placement, sufficient eye clearance, elegant ergonomic design, and advanced automated features to improve performance and usability.

BACKGROUND OF THE INVENTION

Wearable near-to-eye (NR2I) vision systems or NR2I displays are a class of wearable device that creates a display in front of the user's field of vision from an electronic display. The display may be transparent such that the viewer can view the external world and the projected electronic display simultaneously or opaque wherein the viewer may directly view the electronic display or a projected electronic display, depending on the application. For example, a transparent display can overlay information and graphics on top of a real-world image, while an opaque display can provide an immersive theater-like experience. Further NR2I displays may provide information within the full visual field of view of the user or may alternatively provide information within part of the user's field of view.

NR2I displays can be broadly placed in two categories, immersive and see-through. Immersive NR2I displays block a user's view of the real world and create a large field of view image, typically 30°-60° for cinema glasses and 90° or more for virtual reality displays. See-through NR2I displays leave the user's view of the real world open and create either a transparent image or a very small opaque image that blocks only a small portion of the user's peripheral vision. The see-through category can be further broken down into two applications, augmented reality and smart glasses. Augmented reality headsets typically offer 20°-60° fields of view and overlay information and graphics on top of the user's view of the real world. Smart glasses in contrast typically have a smaller field of view and a display which the user glances at periodically rather than looking through the display continuously.

For users exploiting NR2I displays for augmented reality and/or correction of low vision, then the user is typically either going to wear the NR2I displays for specific tasks, for specific visual environments, etc. and hence there is an issue of repeatedly attaching and removing the NR2I display or they are going to be wearing the NR2I display for extended periods of time, potentially all their time awake. Accordingly, the majority of applications irrespective of whether they are for short-term, long-term, low vision, augmented reality, etc. yield a conflicting set of tradeoffs between user comfort and minimal fatigue and strain during use, ease of attachment, minimizing intrusiveness and aesthetics which must be concurrently balanced with and are often in conflict with providing an optical vision system within the NR2I display that provides the user with a wide field of view and high image resolution whilst also offering a large exit pupil for eye placement with sufficient eye clearance. Further, individual users' needs vary between users, and vary both with the general task at-hand and with a user's visual focus and intent upon various regions-of-interest within their field of view. Accordingly, it would be beneficial to provide NR2I systems that address these issues and provide a high performance optical system within an advance in the field of head-mounted displays and NR2I systems to provide an eyepiece design and system features which overcome these limitations. Herein we describe systems and methods that allow for an improved user experience when using NR2I HMDs.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to wearable NR2I vision systems and more particularly to provide wearable NR2I vision systems with wide field of view, high image resolution, large exit pupil for eye placement, sufficient eye clearance, elegant ergonomic design, and features to allow improved contrast, latency, and bio-mimicry of the user's experience in a more natural environment.

In accordance with an embodiment of the invention a near-to-eye (NR2I) display system comprising:
- a freeform prism lens (prism) parallel to a transverse plane of a user;
- a micro-display proximate a first face of the prism for displaying content to be displayed to a user of the NR2I system;
- an infra-red sensor to image a portion of the user's eye to which the prism relates proximate a different face of the prism that that proximate the micro-display and that proximate the user's eye;
- a plurality of infra-red optical sources to illuminate the user's eye;
- an integrated processing capability; and
- computer readable instructions within a non-volatile non-transitory storage medium for execution by the integrated processing capability in order to detect a direction of a preferred retinal location of the user based upon information acquired from the infra-red sensor.

In accordance with an embodiment of the invention the plurality of infra-red sources comprise at least one of:
- an optical infra-red source adjacent to the micro-display coupled to the user's eye via the prism;
- an optical infra-red source illuminating the user's eye directly;
- an optical infra-red source coupled via an optical waveguide disposed within an assembly comprising the prism;
- an optical infra-red source coupled via an optical waveguide formed within the prism.

In accordance with an embodiment of the invention the infra-red sensor does not have at least one of an optical lens and a pinhole disposed between it and the prism.

In accordance with an embodiment of the invention there is provided a near-to-eye eye-tracked head-mounted display (NR2I display), comprising:

a micro-display for generating an image to be viewed by a user, the micro-display having a display optical path and an exit pupil associated therewith;

a first plane located at the micro-display and a second plane located at the exit pupil;

an eye-facing image sensor configured to receive reflected optical radiation from the second plane reflected from a user's eye, the image sensor having a sensor optical path associated therewith; and display optics disposed in optical communication with the micro-display along the display optical path and in optical communication with the image sensor along the sensor optical path, the display optics having a selected surface closest to the micro-display and the image sensor, the display optics located relative to the micro-display and image sensor such that the display and image sensor optical paths impinge upon differing respective portions of the selected surface; wherein the display optical path within the display optics is substantially parallel to a line joining the centres of the user's eyes.

In accordance with the embodiment of the invention the micro-display, image sensor, and display optics form part of a bioptic assembly allowing the user to move the NR2I display between a first position with it disposed up such that the NR2I display is not within the user's line of sight and a second position with it disposed down such that the NR2I display is within the user's line of sight.

In accordance with an embodiment of the invention an eye-facing image sensor receives reflected optical radiation from a plurality of near infra-red optical sources wherein the plurality of optical sources are coupled to the user's eye at least one of directly without passing through the display optics, through the display optics, through a plurality of optical waveguide disposed separate to the display optics, and through a plurality of optical waveguide integrated within the display optics.

In accordance with an embodiment of the invention the NR2I display incorporates a lens disposed between the display optics and the user's eye and the image sensor allows for at least one of determination through eye-tracking of the presence of the lens and adjustment of at least one of estimated gaze direction and position of the micro-display relative to the display optics to compensate for the presence of the lens.

In accordance with an embodiment of the invention the NR2I display provides for an adjustment of a position of the micro-display relative to the display optics from an initial position is made in order to provide an adjusted optical path, the adjusted optical path being that the user would have through the display optics with a prescription lens to their prescription disposed between the display optics and user's eye.

In accordance with an embodiment of the invention the image sensor receives reflected optical radiation from a plurality of near infra-red optical sources which are integrated with the micro-display.

In accordance with an embodiment of the invention there is provided near-to-eye (NR2I) display system comprising:

a first assembly comprising at least a pair of temple arms, a nose bridge, a strap between the temple arms that bears some or all of the weight of an attached display assembly, and a first portion of a hinged attachment to a second assembly;

the second assembly, the second assembly comprising at least a micro-display, an optical train to allow a user to view the image created by the micro-display, an infra-red sensor used to image the user's eye(s), and a second portion of the hinged attachment to the first assembly;

a processing system that determines the direction of a user's preferred retinal location within the displayed image; wherein the processing of the users preferred retinal location is performed in dependence upon the angle of the hinged attachment between the two assemblies.

In accordance with an embodiment of the invention the optical train is either a horizontally disposed freeform prism or a horizontally disposed freeform prism with a freeform compensator for the user's direct field of view and the infra-red sensor is disposed in front of the user's eye.

In accordance with an embodiment of the invention there is provided a high dynamic range optical sensor comprising an optical sensor and at least one micro-shutter of a plurality of micro-shutters.

In accordance with an embodiment of the invention there is provided near-to-eye (NR2I) display system comprising a micro-display disposed in a predetermined position relative to the front of an eye of a user of the NR2I display, an optical train to couple the micro-display to the user's eye and allow the user to view their external environment through the optical train, and a plurality of micro-shutters disposed with respect to the optical train between the external environment and the optical train.

In accordance with an embodiment of the invention the NR2I allows a to view a synthesized image comprising a first portion provided by one or more display regions of the micro-display, and a second portion provided by one or more environment regions of the external environment, wherein a first subset of the plurality of micro-shutters associated with the one or more display regions are configured to block the external environment and a second subset of the plurality of micro-shutters associated with the one or more environment regions are configured to pass the external environment.

In accordance with an embodiment of the invention there is provided a near-to-eye display system comprising:

a left optical assembly comprising a first micro-display disposed in a predetermined position relative to the front of a left eye of a user of the NR2I display and a first optical train to couple the first micro-display to the user's left eye;

a right optical assembly comprising a second micro-display disposed in a predetermined position relative to the front of a right eye of a user of the NR2I display and a second optical train to couple the second micro-display to the user's right eye;

a processor to generate the content to be displayed by the first micro-display and the second micro-display wherein an image to be viewed by the user is split into a first predetermined portion for display by the first micro-display and a second predetermined portion for display by the second micro-display; wherein a predetermined portion of the first predetermined portion of the image overlaps a predetermined portion of the second predetermined portion of the image such that the user can view a wide field of view.

In accordance with an embodiment of the invention there is provided a near-to-eye (NR2I) display system comprising:

an assembly comprising a freeform prism lens, a micro-display for projecting image-light onto a region of a first surface of said freeform prism-lens, said image light performing two internal reflections within the freeform prism-lens before exiting the freeform prism-lens for viewing by the user with an eye, wherein the micro-display is fixedly held in position by said assembly relative to said first surface of the freeform prism lens and proximate a temple of the user nearest the user's eye viewing the projected image-light, such assembly having attachment features such that lateral motion of the assembly across the user's horizontal field of view when attached to a body of the NR2I system is made possible.

In accordance with an embodiment of the invention there is a provided near-to-eye (NR2I) display system further comprising:

a second assembly comprising a second freeform prism lens, a second micro-display for projecting image-light onto a predetermined region of a first surface of said second freeform prism-lens, said image light performing two internal reflections within the second freeform prism-lens before exiting the second freeform prism-lens for viewing by the user with their other eye, wherein the second micro-display is fixedly held in position relative to said first surface of the second freeform prism lens and proximate the user's other temple by said second assembly, such assembly having attachment features such that lateral motion of the second assembly across the user's horizontal field of view when attached to the body of the NR2I system is made possible allowing the positions and separation of the assembly and second assembly to be established in dependence upon the positions and the inter-pupil distance of the user's eyes In accordance with an embodiment of the invention there is provided a near-to-eye (NR2I) display system comprising an assembly comprising:

freeform prism lens and a micro-display for projecting image-light onto a first surface of said freeform prism-lens, said image light projecting onto a second surface of said freeform prism-lens performing a first internal reflection to a third surface of the freeform prism-lens, a second internal reflection from the third surface towards a predetermined region of the second surface whereupon the light exits the freeform prism-lens towards the user's eye through said predetermined region; wherein external light is prevented from entering substantially all the second surface excluding said predetermined region through at least one of an applied coating to the second surface of the freeform prism-lens and opaque structures external to the freeform prism-lens.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 2A to 2C respectively depict a bioptic immersive NR2I-HMD system according to an embodiment of the invention exploiting a NR2I freeform prism-lens according to an embodiment of the invention wherein the user has pivoted the NR2I system down in front of their eyes;

FIGS. 2N to 2O respectively depict an alternative configuration for a bioptic immersive NR2I-HMD according to the embodiment of the invention in FIGS. 2G to 2M respectively exploiting a NR2I freeform prism-lens according to another embodiment of the invention wherein the user has positioned the NR2I-HMD out of their direct line of sight and in their line of sight;

FIG. 2P depicts an alternative configuration for a bioptic immersive NR2I-HMD according to an embodiment of the invention exploiting a NR2I freeform prism-lens according to another embodiment of the invention wherein the user has positioned the NR2I-HMD in their line of sight;

FIG. 5 depicts a freeform lens assembly according to an embodiment of the invention with the display vertically mounted above the left and right eyes of the user for the left and right eyes respectively indicating different regions of the freeform lens facet facing the user's eye;

FIG. 6 depicts a freeform lens assembly according to an embodiment of the invention for an exemplary NR2I-HMD employing a freeform corrector lens to reduce aberrations in a direct field-of-view image viewed by the user through the freeform lens assembly;

FIG. 20A depict the inner facing portion of a NR2I-HMD systems according to an embodiment of the invention wherein the dual display portions are set to maximum IMD and exploit NIR LEDs forming part of the display elements emitting to the pupil facing facet of the freeform prism;

FIG. 20B depicts the inner facing portion of a NR2I-HMD systems according to an embodiment of the invention wherein the dual display portions are set to minimum IMD and exploit optical light guides coupling from optical sources laterally mounted within the display elements to points on the pupil facing facet of the freeform prism;

FIG. 21 depicts an exemplary code segment for performing separate distortion map corrections for digital pre-compensation of chromatic distortion in the red, green, and blue display portions without dynamic IPD correction;

FIG. 22 depicts an exemplary code segment for performing separate distortion map corrections for digital pre-compensation of chromatic distortion in the red, green, and blue display portions with dynamic IPD vergence correction;

FIG. 23 depicts an exemplary code sequence for a configuration and initialization sequence for a NR2I-HMD according to an embodiment of the invention;

FIG. 30 depicts exemplary images to be presented to a user of a NR2I-HMD according to an embodiment of the invention for determining user astigmatism;

FIG. 31 depicts exemplary images of a colour-remapping to be presented to a user of a NR2I-HMD according to an embodiment of the invention for determining colour blindness and colour re-mapping parameters;

FIGS. 38 and 39 depict alternate binocular image projection techniques that may be employed within a NR2I-HMD system according to embodiments of the invention;

DETAILED DESCRIPTION

Figure 1A:
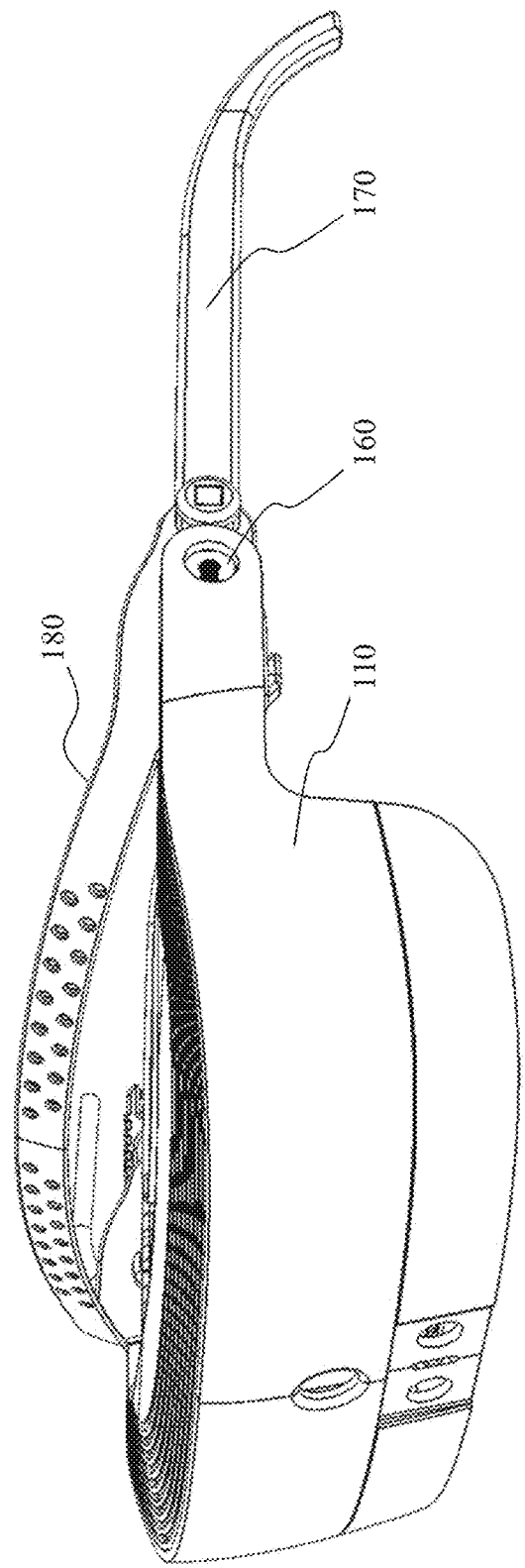
FIGS. 1A and 1B depict a near-to-eye (NR2I) head mounted display (HMD) system comprising a frame with temple-arms, a weight-relieving strap, a demountable display assembly that pivots about a magnetic hinged attachment, allowing rotation of the display assembly together with additional forward-facing elements such as one or more image sensors, range-finders, and structured/unstructured light sources.

The present invention is directed to wearable NR2I vision systems and more particularly to providing wearable NR2I vision systems with wide field of view, high image resolution, large exit pupil for eye placement, sufficient eye clearance, and elegant ergonomic design which may employ user gaze-direction tracking to implement certain features.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users. Reference to terms "including", "comprising", "consisting" and grammatical variants thereof do not preclude the addition of one or more components, features, steps, integers or groups thereof and that the terms are not to be construed as specifying components, features, steps or integers. Likewise, the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

A "near-to-eye head-mounted display" (NR2I-HMD system, NR2I-HMD, NR2I display or simply NR2I system of NR2I) as used herein and throughout this disclosure refers to a wearable device that incorporates an image presentation device operating in conjunction with a microprocessor such that a predetermined portion of an image may be presented to the user on the image presentation device (NR2I display). The image presentation device is typically an LCD display, LED display, or OLED display although any display generation device capable of being mounted and supported as part of a NR2I may be considered. As noted supra a NR2I may be configured as immersive, wherein the user views the display absent any direct external visual view, or non-immersive, wherein the user views the display with direct external visual view. Configurations of NR2I and their associated NR2I display may include immersive with direct viewer viewing of NR2I display, immersive with indirect viewer viewing of NR2I display through an intermediate optical assembly, non-immersive with direct viewer viewing of NR2I display which is substantially transparent, immersive with indirect viewer viewing of NR2I display through an intermediate optical assembly. Optical sub-assemblies for indirect viewer viewing of the NR2I display may employ the NR2I display to the sides of the viewer's head or above the viewer's eyeline. Non-immersive configurations may employ a non-transparent display or optical assembly where the display presents to a smaller field of view than the user's full field of view or is within their peripheral vision such that it does not overlay the central portion of their field of view.

A NR2I may be monocular or binocular. A NR2I display may be fixed, i.e. when worn it is in a fixed configuration relative to the user's head, or bioptic, i.e. when worn it allows the user to vary the NR2I configuration relative to their head in two (2), three (3), or more predetermined positions and/or may be continuously or pseudo-continuously variable. In some instances, the NR2I may pivot automatically between positions based upon user's head position or it may be moved manually etc. The NR2I display may be mounted to a frame worn by the user that simply supports the NR2I display or the frame may include one or two lenses, prescription lenses, filters, polarizing elements, photochromic elements, electrochromic elements, etc. The NR2I display may be fixed to the frame or demountably attached to the frame. The NR2I display may include additional elements such as electronics, one or more cameras, one or more optical emitters, one or more wireless interfaces, one or more wired interfaces, and one or more batteries.

A NR2I display may present an image to the user which may be acquired from a camera also forming part of the NR2I or a camera associated with the user such as through a remotely attached camera for example. Alternatively, the image(s)—video content may be acquired from a portable electronic device, a fixed electronic device, a cable set-top box, satellite set-top box, or any video source. The image presented to the user may be as directly acquired, processed to fit display, etc. or aligned to elements within the field of view based upon image processing such that, for example, a schematic overlay may be aligned to a circuit being worked upon by the user. Within other embodiments of the invention the image may be processed to augment/enhance the visual perception of the user.

An NR2I display may include a microprocessor together with any other associated electronics including, but not limited to, memory, user input device, gaze tracking, inertial sensors, context determination, graphics processor, and multimedia content generator may be integrated for example with the NR2I, form part of an overall assembly with the NR2I, form part of the PED, or as discrete unit wirelessly connected to the NR2I and/or PED. Accordingly, for example, the NR2I displays may be coupled wirelessly to the user's PED whereas within another embodiment the NR2I may be self-contained.

A "freeform optical element" as used herein and through this disclosure refers to, but is not limited to, an optical element such as a lens, prism, mirror, etc. which exploits one or more freeform optical surfaces.

A "freeform optical surface" as used herein and through this disclosure refers to, but is not limited to, an optical surface that is by design non-rotationally symmetric and/or has non-symmetric features. These surfaces leverage a third independent axis, the C-axis from traditional diamond turning terminology, during the creation process to create these optical surfaces with as designed non-symmetric features. Such freeform optical surfaces may exploit, for example, the Zemike polynomial surface or its derivatives, multi-centric radial basis function (RBF) surfaces, Q-polynomial surfaces, non-uniform rational B-splines (NURBS). In some instances, multicentric RBF surfaces are an added layer on an optical surface shape that may itself vary, for example, from a basic spherical surface to a Zemike surface.

A "wearable device" or "wearable sensor" as used herein and through this disclosure refers to, but is not limited to, miniature electronic devices that are worn by the user including those under, within, with or on top of clothing and are part of a broader general class of wearable technology which includes "wearable computers" which in contrast are directed to general or special purpose information technologies and media development. Such wearable devices and/or wearable sensors may include, but not be limited to, smartphones, smart watches, smart glasses, environmental sensors, medical sensors, biological sensors, physiological sensors, chemical sensors, ambient environment sensors, position sensors, and motion sensors.

A "wearer", "user" or "patient" as used herein and through this disclosure refers to, but is not limited to, a person or individual who uses the NR2I either as a patient requiring visual augmentation to fully or partially overcome a vision defect or as an ophthalmologist, optometrist, optician, or other vision care professional preparing a NR2I for use by a patient. A "vision defect" as used herein may refer to, but is not limited, a physical defect within one or more elements of a user's eye, a defect within the optic nerve of a user's eye, a defect within the nervous system of the user, a higher order brain processing function of the user's eye, and an ocular reflex of the user. A "wearer" or "user" may also be an individual with healthy vision, using the NR2I in an application other than for the purposes of ameliorating physical vision defects. Said applications could include, but are not necessarily limited to gaming, augmented reality, night vision, computer use, viewing movies, environment simulation, training, remote-assistance, etc. Augmented reality applications may include, but are not limited to, medicine, visual assistance, engineering, aviation, training, remote-assistance, tactical, gaming, sports, virtual reality, environment simulation, and data display.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, a wearable device and an electronic reader.

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, a gaming console, a digital set-top box, an analog set-top box, an Internet enabled appliance, an Internet enabled television, and a multimedia player.

A "server" as used herein, and throughout this disclosure, refers to one or more physical computers co-located and/or geographically distributed running one or more services as a host to users of other computers, PEDs, FEDs, etc. to serve the client needs of these other users. This includes, but is not limited to, a database server, file server, mail server, print server, web server, gaming server, or virtual environment server.

An "application" (commonly referred to as an "app") as used herein may refer to, but is not limited to, a "software application", an element of a "software suite", a computer program designed to allow an individual to perform an activity, a computer program designed to allow an electronic device to perform an activity, and a computer program designed to communicate with local and/or remote electronic devices. An application thus differs from an operating system (which runs a computer), a utility (which performs maintenance or general-purpose chores), and a programming tools (with which computer programs are created). Generally, within the following description with respect to embodiments of the invention an application is generally presented in respect of software permanently and/or temporarily installed upon a PED and/or FED.

"User information" as used herein may refer to, but is not limited to, user behavior information and/or user profile information. It may also include a user's biometric information, an estimation of the user's biometric information, or a projection/prediction of a user's biometric information derived from current and/or historical biometric information.

"Biometric" information as used herein may refer to, but is not limited to, data relating to a user characterised by data relating to a subset of conditions including, but not limited to, their iris, pupil, cornea, retina shapes and characteristics, environment, medical condition, biological condition, physiological condition, chemical condition, ambient environment condition, position condition, neurological condition, drug condition, and one or more specific aspects of one or more of these said conditions. Accordingly, such biometric information may include, but not be limited, blood oxygenation, blood pressure, blood flow rate, heart rate, temperate, fluidic pH, viscosity, particulate content, solids content, altitude, vibration, motion, perspiration, EEG, ECG, energy level, etc. In addition, biometric information may include data relating to physiological characteristics related to the shape and/or condition of the body wherein examples may include, but are not limited to, fingerprint, facial geometry, baldness, DNA, hand geometry, odour, and scent. Biometric information may also include data relating to behavioral characteristics, including but not limited to, typing rhythm, gait, and voice.

"Electronic content" (also referred to as "content" or "digital content") as used herein may refer to, but is not limited to, any type of content that exists in the form of digital data as stored, transmitted, received and/or converted wherein one or more of these steps may be analog although generally these steps will be digital. Forms of digital content include, but are not limited to, information that is digitally broadcast, streamed or contained in discrete files. Viewed narrowly, types of digital content include popular media types such as MP3, JPG, AVI, TIFF, AAC, TXT, RTF, HTML, XHTML, PDF, XLS, SVG, WMA, MP4, FLV, and PPT, for example, as well as others, see for example http://en.wikipedia.org/wiki/List_of_file_formats. Within a broader approach digital content mat include any type of digital information, e.g. digitally updated weather forecast, a GPS map, an eBook, a photograph, a video, a Vine™, a blog posting, a Facebook™ posting, a Twitter™ tweet, online TV, etc. The digital content may be any digital data that is at least one of generated, selected, created, modified, and transmitted in response to a user request; said request may be a query, a search, a trigger, an alarm, and a message for example.

"Selection" or "user selection" or "user feedback" as used herein may refer to, but is not limited to any means of the user interacting with the NR2I system, including manual pressing of a button or switch, a gesture that is made in front of the NR2I system and detected by one or more forward-facing cameras, a tapping on the device whose vibrations are detected by inertial or vibration sensors within the device, an audio cue such as a click or vocal command, such as "stop" "go" or "select", etc., or detection via the eye-tracking system, for instance detected gaze-direction and blink-detection, or any electronic signal from a different device to which the user has access, and with which the Nr2I system is in communication, for instance an external mobile phone or personal electronic device.

A "profile" as used herein may refer to, but is not limited to, a computer and/or microprocessor readable data file comprising data relating to settings and/or limits of an adult device. Such profiles may be established by a manufacturer of the adult device or established by an individual through a user interface to the adult device or a PED/FED in communication with the adult device.

An "infra-red source" as used herein may refer to, but is not limited to, an optical emitter emitting within the near infra-red region of the electromagnetic spectrum such as within the wavelength range 750 nm to 2,500 nm (2.5 µm). This may be generally sub-divided based upon choice of semiconductor employed for the devices such that, for example, gallium arsenide (GaAs) and gallium aluminium arsenide (GaAlAs) for 750 nm-950 nm, indium gallium arsenide (InGaAs) and aluminium gallium arsenide (AlGaAs) for 95-1150 nm, indium gallium arsenide phosphide (InGaAsP) for 1150 nm-1700 nm, and gallium indium arsenide antimonide (1700 nm-2500 nm). Semiconductor devices may include light emitting diodes (LED) such as surface-emitting LED (SLED) and edge-emitting LED (ELED), superluminescent diodes (SLEDs), laser diodes (LDs) and vertical cavity surface emitting lasers (VCSELs).

An "infra-red detector" as used herein may refer to, but is not limited to, an optical receiver or display capable of detecting signals within the near infra-red region of the electromagnetic spectrum. Common materials for NIR detectors include silicon (Si) and indium gallium arsenide (InGaAs) which may be employed as photodiodes or phototransistors discretely, in linear arrays or two-dimensional (2D) arrays to form an "infra-red image sensor". Such devices may exploit associated silicon processing circuits or in the instances of CMOS or charge-coupled devices (CCDs) be formed integrally with the silicon circuits.

An "optical waveguide" as used herein may refer to, but is not limited to, a structure designed to confine light to propagating within the optical waveguide through total internal reflection or index contrast based confinement. An optical waveguide may be designed to support a single optical mode, a monomode optical waveguide, whereas other optical waveguides may be designed to support a limited number of modes or many modes, so-called multimode optical waveguides. Optical waveguides may be formed in materials transparent to the target optical wavelength range through different processes including, but not limited to, molding, stamping, etching and doping. For example, optical waveguides may be formed by locally increasing the refractive index to form a core of an optical waveguide such as via an ion exchange processes within glass materials such as silver-sodium ion exchange, for example, or ion implantation and/or locally lowering the refractive index to form a cladding of the optical waveguide such as by laser induced defect/damage within a glass or etching the material away to surround the optical waveguide with air. Optical waveguides may be formed by coating filaments with a lower index material, e.g. polymer coating glass or polymer-polymer or glass-glass etc. Optical waveguides may be formed in glasses, polymers, crystals, semiconductors etc. and may have different geometries including, but not limited to, circular, elliptical, square, and rectangular.

A "coronal plane" (frontal plane) as used herein refers to a vertical plane running from side to side which divides the body or any of its parts into anterior and posterior portions. A "sagittal plane" (lateral plane) as used herein refers to a vertical plane running from front to back which divides the body or any of its parts into right and left sides. An "axial plane" (transverse plane) as used herein refers to a horizontal plane which divides the body or any of its parts into upper and lower parts. A "median plane" as used herein refers to a sagittal plane through the midline of the body; divides the body or any of its parts into right and left halves.

0. REFERENCE TO RELATED APPLICATIONS

The disclosures described and depicted below in respect of FIGS. 1 to 39 respectively in this patent specification extend and build-upon inventions established by the inventors including the following referenced patent applications which are herein included in their entirety by reference and citation herein:
- 0.A "Apparatus and Method for Augmenting Sight" filed Apr. 2, 2007 with application No. U.S. 60/921,468 and its formalization and continuations including U.S. Ser. No. 12/891,430; U.S. Ser. No. 13/371,521; U.S. Ser. No. 13/947,376; U.S. Ser. No. 15/163,790; U.S. Ser. Nos. 15/475,802; and 15/709,984.
- 0.B "Apparatus and Method for Enhancing Human Visual Performance in a Head Worn Video System" filed Feb. 17, 2012 with application No. U.S. 61/599,996 and Jun. 13, 2012 with application No. U.S. 61/659,128 and their formalizations and continuations including U.S. Ser. No. 13/769,353 and U.S. Ser. No. 15/361,185.
- 0.C "Apparatus and Method for a Bioptic Real Time Video System" filed Dec. 3, 2010 with application No. U.S. 61/419,359 and its formalization and continuations including U.S. Ser. No. 13/309,717; U.S. Ser. No. 14/562,241; and U.S. Ser. No. 15/181,874.
- 0.D "Apparatus and Method for a Dynamic 'Region of Interest' in a Display System" filed Nov. 19, 2011 with application No. U.S. 61/262,766 and its formalization and continuations including U.S. Ser. No. 12/060,964; U.S. Ser. No. 12/891,430; U.S. Ser. No. 15/163,790; and U.S. Ser. No. 15/475,802.
- 0.E "Apparatus and Method for Fitting Head Mounted Vision Augmentation Systems" filed Dec. 31, 2012 with application No. U.S. 61/747,380 and its formalization and continuations including U.S. Ser. No. 14/758,623 and U.S. Ser. No. 15/585,809.
- 0.F "Methods and Devices for Optical Focus and Depth Information Extraction" filed May 10, 2015 with application No. U.S. 62/237,141 and its formalization PCT/CA2016/000248.
- 0.G "Methods and Devices for Optical Aberration Correction" filed Apr. 22, 2015 with application No. U.S. 62/150,911 and its formalization and continuations including U.S. Ser. No. 15/135,805 and U.S. Ser. No. 15/799,075.
- 0.H Methods and Devices for Demountable Head Mounted Displays filed Jul. 6, 2017 with application No. U.S. 62/188,831 and its formalization PCT/CA2016/000189.
- 0.I "Language Element Vision Augmentation Methods and Devices" filed Jan. 12, 2016 with application No. filed 62/277,510 and its formalization U.S. Ser. No. 15/404,700.
- 0.J Large Exit Pupil Wearable Near-to-Eye Vision Systems exploiting Freeform Eyepieces" filed Aug. 12, 2016 with application No. U.S. 62/374,208 and its formalization U.S. Ser. No. 15/676,053.

1. OPTICAL TRAIN DESIGN

Many methods have been explored to achieve an NR2I optical system which fulfils the requirements outlined in the background. These methods include applying catadioptric techniques, introducing new elements such as aspherical surfaces, holographic and diffractive optical components, exploring new design principles such as using projection optics to replace an eyepiece or microscope type lens system in a conventional NR2I design, and introducing tilt and decenter or even freeform surfaces. Within these different methods that of freeform optical technology has demonstrated promise in designing the required compact NR2I systems. In particular, a wedge-shaped freeform prism-lens takes advantage of total internal reflection (TIR), which helps minimize light loss and improve the brightness and contrast of the displayed images.

2. NR2I DISPLAY DESIGN

Figure 1B:
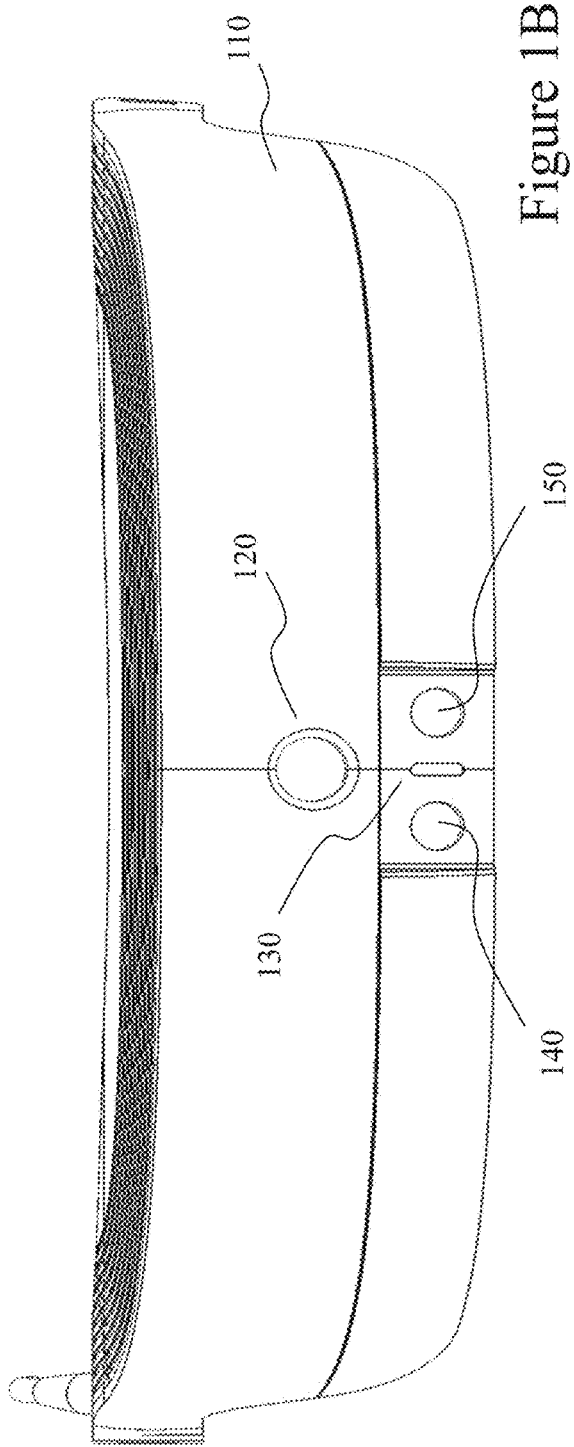

Referring to FIGS. 1A and 1B depict a near-to-eye (NR2I) head mounted display (HMD) system comprising a frame with temple-arms 170, a weight-relieving strap 180, a Demountable Display Assembly 110 that pivots about a magnetic hinged attachment 160, allowing rotation of the display assembly together with additional forward-facing elements such as one or more image sensors 120, rangefinders 140 and 150, and a structured/unstructured light source 130.

Figures 2D, 2E, 2F:
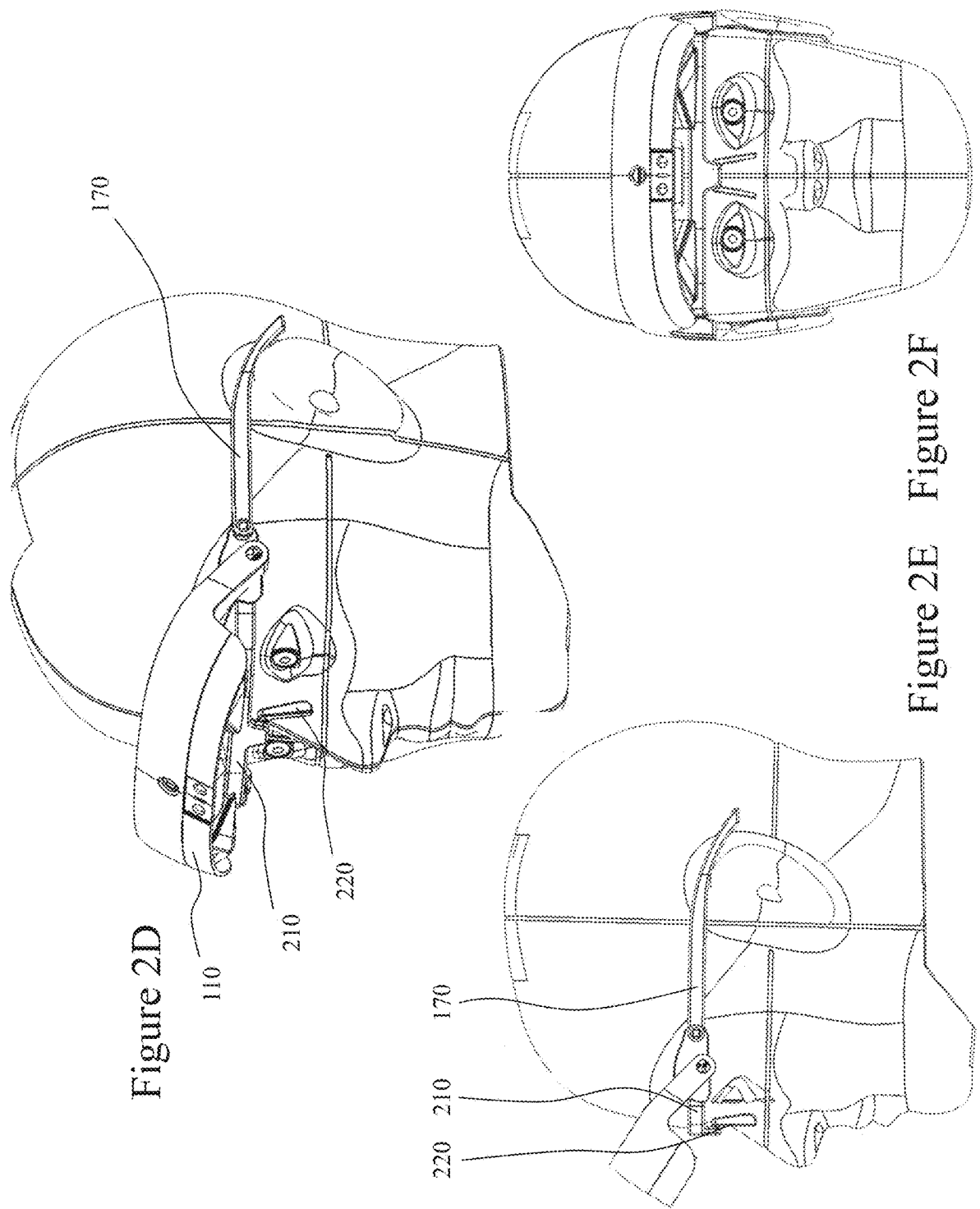
FIGS. 2D to 2F respectively depict the bioptic immersive NR2I-HMD system according to the embodiment of the invention depicted in FIGS. 2A to 2C exploiting a NR2I freeform prism-lens according to an embodiment of the invention wherein the user has pivoted the NR2I system up.

Referring to FIGS. 2A to 2C respectively there are depicted side perspective, side elevation, and front elevation views of a bioptic immersive NR2I-HMD (BI-NR2I-HMD) system according to an embodiment of the invention exploiting freeform prism-lenses according to embodiments of the invention such as described and depicted below. Within FIGS. 2A to 2C the user has the BI-NR2I system pivoted down in front of their eyes whilst referring to FIGS. 2D to 2F respectively then there are depicted the same side perspective, side elevation, and front elevation views of the BI-NR2I-HMD system wherein the user has raised the Demountable Display Assembly 110 of BI-NR2I-HMD system up and views their external environment directly. The BI-NR2I-HMD system is attached to a frame 210 that sits onto the bridge of the user's nose via a bridge piece 220 and the upper surfaces of their ears in a similar manner to conventional eyeglasses via temple-arms 170. However, the BI-NR2I-HMD system as depicted can be pivoted into and out of the line of sight of the user.

Within other embodiments of the invention the NR2I-HMD system may be rigidly attached such that it can only be viewed immersively (I-NR2I-HMD) when worn or the NR2I-HMD system may be transmissive (T-NR2I-HMD) or bioptic transmissive (BT-NR2I-HMD) allowing the user to view the external world whilst viewing the NR2I display content concurrently and then pivot the HMD out of the way. Whilst FIGS. 1 to 2F depict a NR2I-HMD design based upon a frame with temple arms, similar to standard glasses—safety eyewear etc., and a weight relieving strap across the forehead it would be evident that other designs may employ embodiments of the invention including, but not limited to, those based upon elastic straps around the user's head, solid ring based frames that mount around the user's head. Optionally, the HMD may be supported upon the user's ears, nose bridge, head, forehead, shoulders, or neck or combinations thereof. Optionally, the NR2I-HMD system may be demountable from the frame such as described by the inventors within World Patent Application PCT/CA2016/000,189 filed Jul. 6, 2016 entitled "Methods and Devices for Demountable Head Mounted Displays." The NR2I-HMD system may also support additional positions either discretely or in a continuous manner such as described and depicted in U.S. Pat. Nos. 8,976,086 and 9,372,348 entitled "Apparatus and Method for a Bioptic Real Time Video System."

In brief overview and referring to FIGS. 2A to 2F respectively, the NR2I system incorporates a pair of frames and a NR2I display which is controlled by a microprocessor. The microprocessor may be a general-purpose microcontroller, microprocessor, or computer o some embodiments of the invention but in other embodiments of the invention it may be an application specific integrated circuit (ASIC) or field programmable gate array (FPGA). The frame may be a lens less frame solely intended to allow the wearer to wear and support the NR2I display and form part of the NR2I system or alternatively it may be a frame with a single prescription lens or a pair of prescription lenses. Optionally, the frame may support non-prescription lenses such as reactive sunglasses, sunglasses, etc. Alternatively, it may be a baffled frame wherein "baffles" are disposed at predetermined locations around the frame to fill regions around the NR2I display/system and the user's head such that the effect of ambient light is reduced which may be particularly beneficial in high ambient light environments. Optionally, the lenses within the frames may be polarizing sheets such as employed in sunglasses, photochromic glass as employed in sunglasses, and filter(s) either in combination with prescription elements or in isolation. Optionally, within other designs with transmissive NR2I functionality a neutral density filter or photochromic glass may be disposed to the side distal from the user to reduce ambient lighting either by a fixed amount or variable amount.

Alternate means of securing the NR2I displays to the user's head whilst still providing bioptic operation are shown in FIGS. 2G to 2P respectively representing two different approaches. Referring initially to FIGS. 2G to 2J respectively there is depicted an alternative configuration for a bioptic immersive NR2I-HMD according to an embodiment of the invention exploiting a NR2I freeform prism-lens according to another embodiment of the invention wherein the user has the NR2I-HMD positioned in multiple positions. As depicted the NR2I-HMD comprises a headband 2120 extends from the user's forehead and around past the user's ears, with a housing 2110 within which, for example, one or more batteries, display and control electronics for the NR2I displays, wireless interface electronics for coupling the NR2I-HMD with a PED and/or FED may be housed. On the front of the headband the headband 2120 has a slider housing 2130 which a slider 2140 can move vertically. Attached to the slider 2140 is the NR2I-Housing 2150 comprising an external casing within which are housed a NR2I display or NR2I displays according to whether the NR2I-HMD is monocular or binocular. When monocular the casing may be as shown across both of the user's other eye or only across one eye. The housing 2110 by virtue of being mounted towards the rear of the user's head offsets forward weight of the NR2I-Housing 2150.

Optionally, the housing 2110 may facilitate the attachment of one or more weights and/or batteries such that counterbalancing of the housing 2110 against the NR2I-Housing 2150 may be tuned to the user. The headband 2120 may stop on one side of the user's head or it may continue around the user's head to the other side. Optionally, the other side of the headband 2120 may also end in a second housing 2110. Optionally, when the headband 2120 fits around both sides of the user's head then the headband 2120 may be a single piece-part of it may alternatively comprise a pair of piece-parts wherein one forms a track provided in the top-front of the headband into which a mating structural member may slide allowing the headband 2120 to be adjusted. Similarly, the housing(s) 2110 may be slidably positioned onto the headband allowing the NR2I-HMD to be fitted to accommodate a range of user physical dimensions such as overall head width, head length, distance from forehead to ears etc.

Figure 2G:
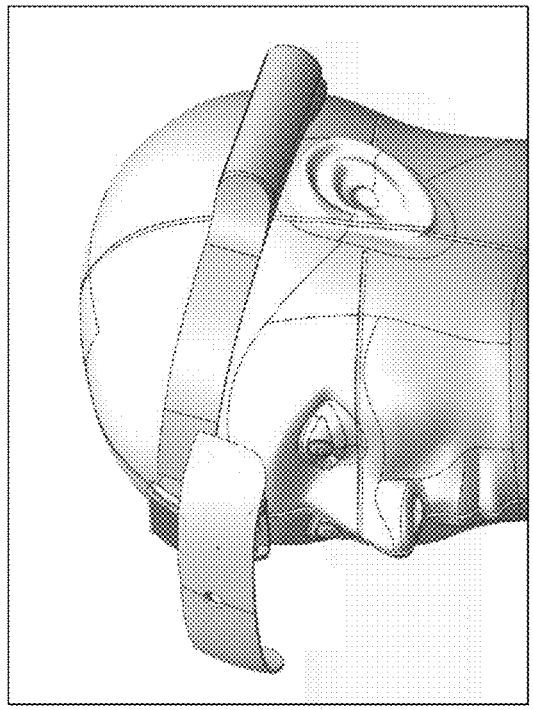
FIGS. 2G to 2J respectively depict an alternative configuration for a bioptic immersive NR2I-HMD according to an embodiment of the invention exploiting a NR2I freeform prism-lens according to another embodiment of the invention wherein the user has the NR2I-HMD positioned in multiple positions.
Figure 2H:
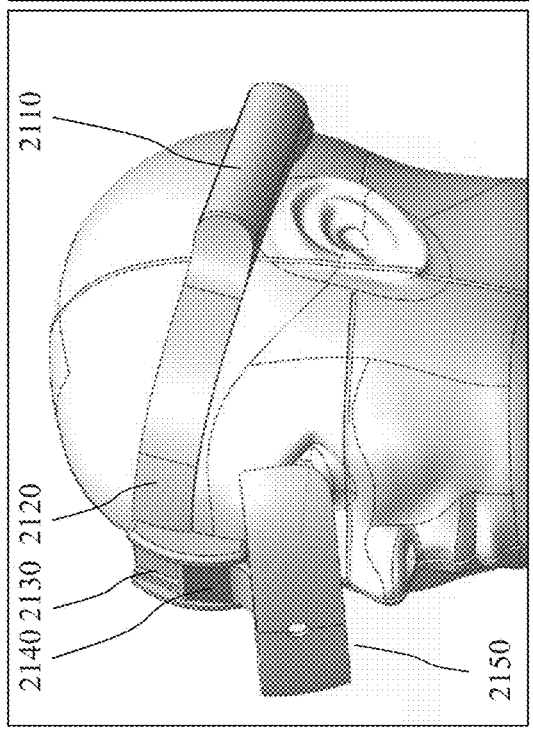
Figure 2I:
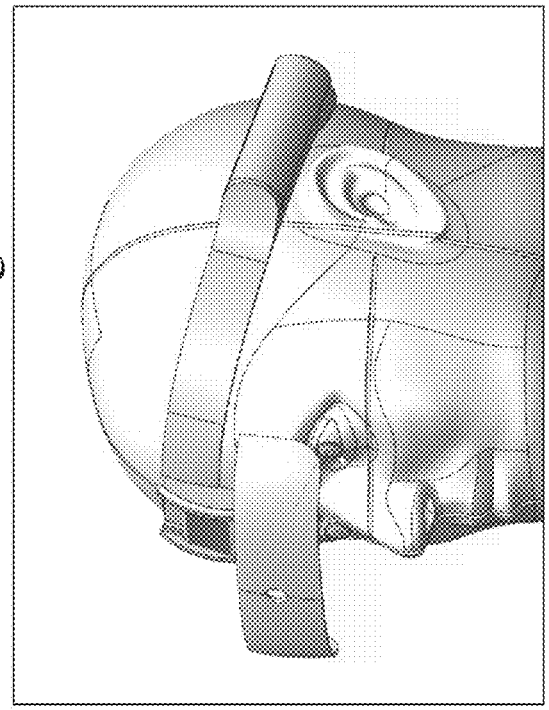
Figure 2J:
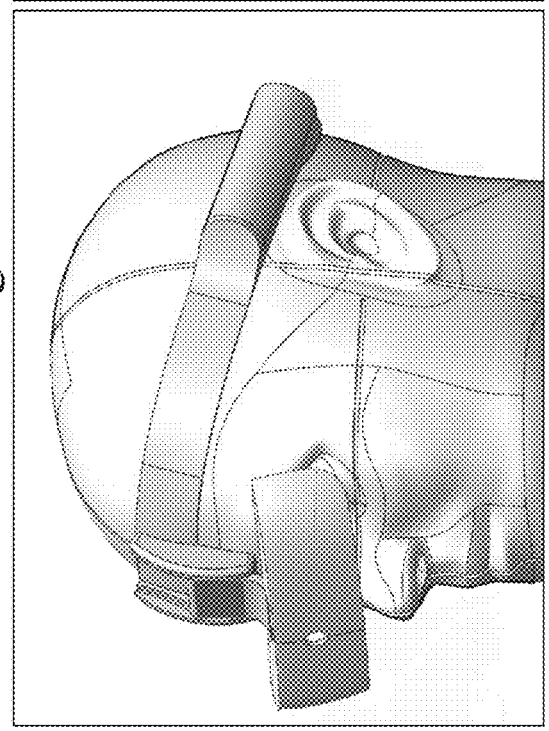

Within FIGS. 2G to 2J respectively the NR2I-HMD is depicted as follows:

FIG. 2G in a first use configuration where the NR2I-Housing 2150 is in front of the user's eyes and with their head level the center of the NR2I display(s) are directly within their line of sight;

FIG. 2H in a second use configuration where the NR2I-Housing 2150 is in front of the user's eyes and with their head level the center of the NR2I display(s) are below their line of sight;

FIG. 2I in a third use configuration where the NR2I-Housing 2150 is raised up out of their line of sight; and FIG. 2J in a fourth use configuration where the NR2I-Housing 2150 is raised up out of their line of sight but visible by movement of the user's eyes upwards.

Figure 2K:
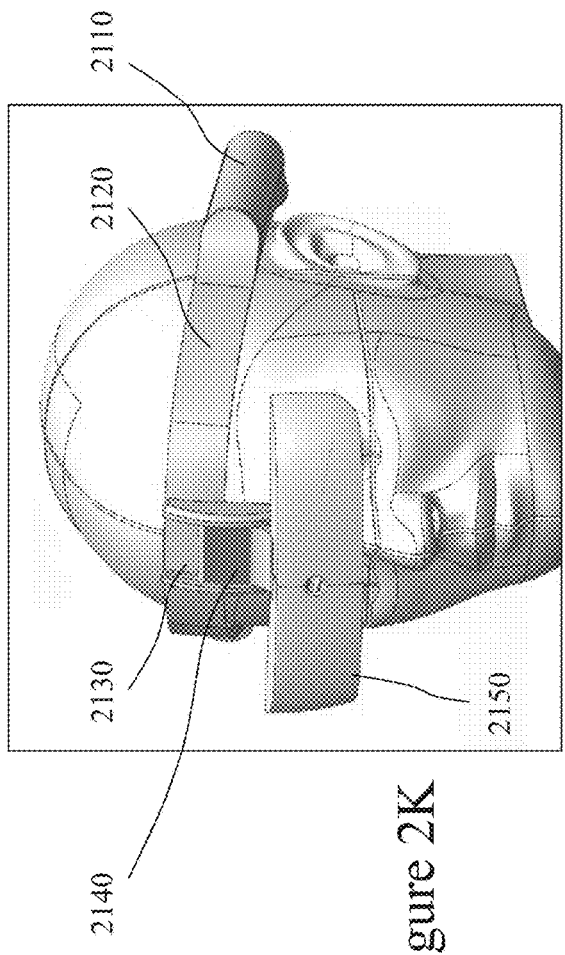
FIGS. 2K to 2M respectively depict an alternative configuration for a bioptic immersive NR2I-HMD according to the embodiment of the invention in FIGS. 2G to 2J respectively exploiting a NR2I freeform prism-lens according to another embodiment of the invention wherein the user has the NR2I-HMD in different positions in front of their eyes.
Figure 2M:
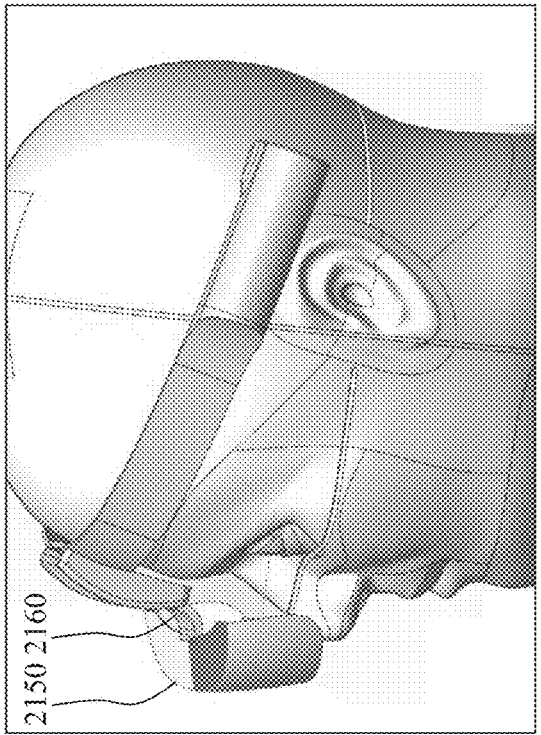
Figure 2L:
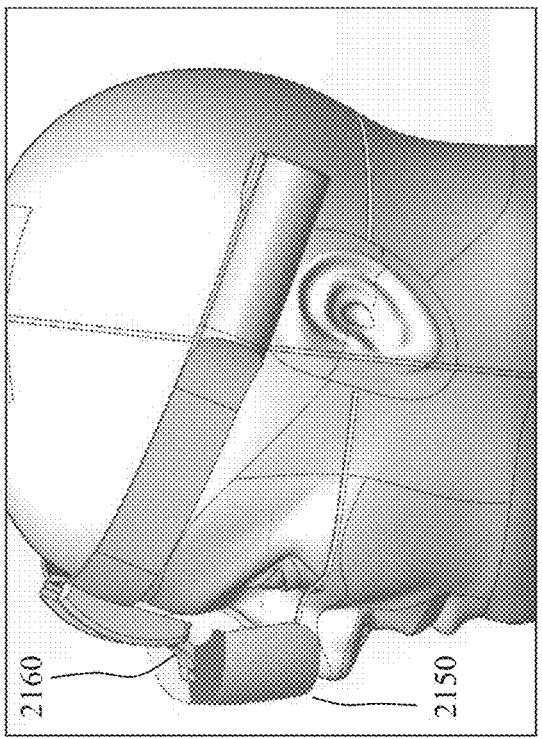

Now referring to FIGS. 2K to 2M respectively there is depicted an alternative configuration for a bioptic immersive NR2I-HMD according to the embodiment of the invention in FIGS. 2G to 2J respectively exploiting a NR2I freeform prism-lens according to another embodiment of the invention wherein the user has the NR2I-HMD in different positions in front of their eyes. Within FIGS. 2K to 2M respectively the NR2I-HMD is depicted as follows:

FIG. 2K in the first use configuration where the headband 2120 can now be seen to run around both sides of the user's head;

FIG. 2L in the first use configuration where the NR2I-Housing 2150 is slid fully onto the slider coupling 2160 at the bottom of the slider 2140 such that the NR2I displays are at a predetermined minimum distance from the user's eyes (minimum eye relief); and FIG. 2M in the first use configuration where the NR2I-Housing 2150 is slid fully out on the slider coupling 2160 at the bottom of the slider 2140 such that the NR2I displays are at a predetermined maximum distance from the user's eyes (maximum eye relief).

Accordingly, the slider coupling 2160 allows the NR2I-Housing 2150 to be moved to different distances from the user's eyes in any of the user configurations. Now referring to FIGS. 2N to 2O respectively there are depicted views of the alternative configuration for a bioptic immersive NR2I-HMD according to the embodiment of the invention in FIGS. 2G to 2M respectively exploiting a NR2I freeform prism-lens according to another embodiment of the invention wherein the user has positioned the NR2I-HMD out of their direct line of sight and in their line of sight respectively. For illustration purposes only the NR2I display 2170 is depicted within the NR2I-Housing 2150. Within the center of the NR2I-Housing 2150 is a window 2180 which may be transparent relative to an opaque, transparent or partially opaque NR2I-Housing 2150. The window 2180 may protect one or more optical imaging devices, e.g. CCD camera, one or more infrared range finders, etc. within embodiments of the invention.

Now referring to FIG. 2P there is depicted an alternative configuration for a bioptic immersive NR2I-HMD according to an embodiment of the invention exploiting a NR2I freeform prism-lens according to another embodiment of the invention wherein the user has positioned the NR2I-HMD in their line of sight. Accordingly, the NR2I-HMD comprises a head mounted frame comprising a rear portion 2210 which fits around the sides and rear of the user's head and a front portion 2220 which fits around the front of the user's head at their forehead level. Coupled to the front portion 2220 is the NR2I-Housing 2230 via pivot mounts 2240 on either side of the user's head. Also depicted in FIG. 2P are a conventional set of eyewear frames 2250 and their lenses 2260. Accordingly, the NR2I-HMD can be work with or without such eyewear frames. Optionally, within another embodiment of the invention the pivot mount 2240 may be only on one side of the user's head.

The rear portion 2210 provides a housing for, for example, one or more batteries, display and control electronics for the NR2I displays, wireless interface electronics for coupling the NR2I-HMD with a PED and/or FED. However, within other embodiments of the invention some circuits for the NR2I-HMD may also be housed within the front portion 2220. As with the design depicted in FIGS. 2G to 2O the rear portion 2210 may provide a counterbalancing for the NR2I-Housing 2230 on the user's head whilst the front portion 2220 resting on the user's forehead provides weight relief. The front portion 2220 may also slidably connect with the rear portion allowing for adjustment of the NR2I-HMD with respect to the user's head. Optionally, the pivot mounts 2240 may slide relative to the front portion 2220 of the frame allowing the distance of the NR2 displays relative to the user's eyes to be adjusted.

Whilst FIGS. 1 to 2P depict a single field-of-view camera centrally located on the front of the NR2I display, alternate functional decompositions are considered. In particular, one or more forward-facing cameras may instead be mounted to the headband so that their directional orientation remains unchanged as the NR2I display position is changed. Further, two forward-facing optical imaging devices, one on each side of the headband, may be used to provide a wider field of view and/or stereoscopic image capture. Similarly, one or more forward facing infrared range finders and/or optical scanners may be mounted to the headband so that their orientation remains unchanged as the NR2I display position is changed. Range finder(s) may provide additional information to the user in their immersive use of the NR2I-HMD whilst an optical scanner or optical scanners may provide environment information which is displayed in conjunction with a field of view or region of interest image derived from the one or more optical imaging devices.

Figure 2Q:
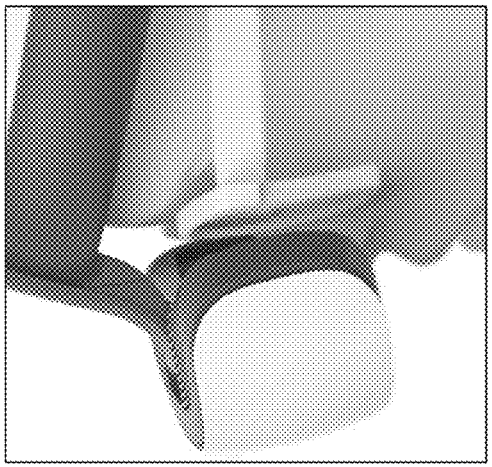
FIGS. 2Q and 2R depict the alternative configuration for a bioptic immersive NR2I-HMD according to the embodiment of the invention in FIGS. 2G to 2O at minimum eye relief with a user not wearing eyewear and a maximum eye relief with a user wearing eyewear.
Figure 2R:
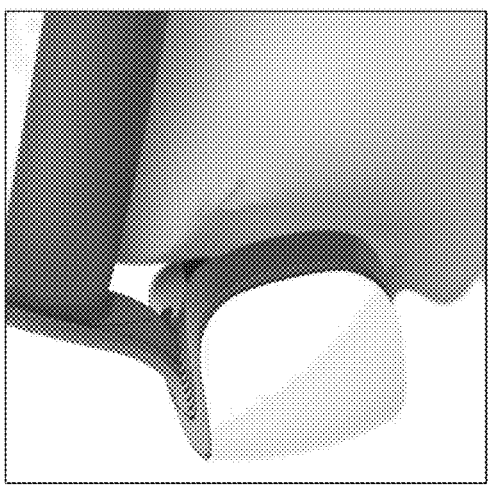

All embodiments of the NR2I display system may allow the use of prescription lenses disposed between the NR2I display and the user's eye. FIG. 2P depicts the prescription lenses being supported from the frame and temple arms of the NR2I head-mounting system. FIG. 2P depicts the use of regular prescription lenses and frames underneath the Display/Headband assemblies. Further, referring to FIGS. 2Q and 2R depict the alternative configuration for a bioptic immersive NR2I-HMD according to the embodiment of the invention in FIGS. 2G to 2O. FIG. 2Q depicts the NR2I-Housing at minimum eye relief with a user not wearing eyewear. FIG. 2R depicts the NR2I-Housing at a maximum eye relief with a user wearing eyewear. For example, according to an embodiment of the invention the minimum eye relief is 15 mm whilst the maximum eye relief is 35 mm although it would be evident that other minimum, maximum, and ranges of accommodation may be implemented.

Removal of heat is a problem for NR2I display systems. In an embodiment the display assembly is provided with vertical openings at the front of the display housing, allowing airflow into the housing and achieving a "chimney effect". Behind the front of the housing may be mounted a heat sink, employing a plurality of heat-pipes to the more dissipative devices within the display assembly. Thus heat is moved away from the user's forehead, and dissipated at the front of the device. The openings allowing airflow may be only present at locations where the user does not touch the assembly, for instance disposed towards the centre of the assembly, so that the user does not feel the heat when touching the device for adjustment, removal, etc.

Figure 2T:
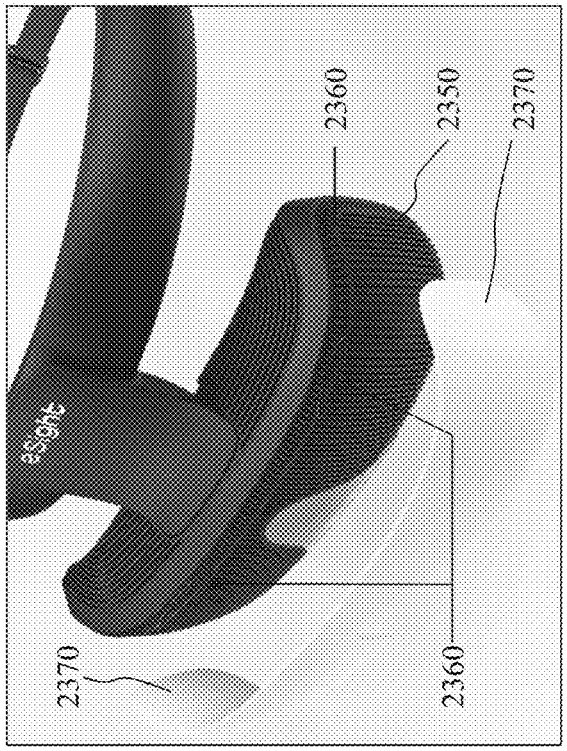
FIG. 2T depicts the bioptic immersive NR2I-HMD according to an embodiment of the invention depicted in FIG. 2S with the front cover removed to show thermal management aspects of the NR2I display portion of the NR2I-HMD.
Figure 2S:
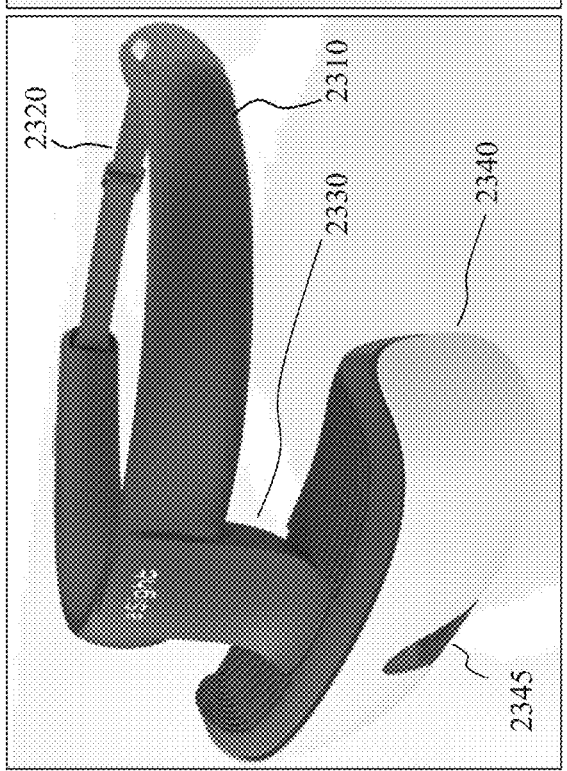
FIG. 2S depicts an alternative configuration for a bioptic immersive NR2I-HMD according to an embodiment of the invention exploiting a NR2I freeform prism-lens according to another embodiment of the invention wherein the user has positioned the NR2I-HMD in their line of sight.

Now referring to FIG. 2S there is depicted an alternative configuration for a bioptic immersive NR2I-HMD according to an embodiment of the invention exploiting a NR2I freeform prism-lens according to another embodiment of the invention wherein the user has positioned the NR2I-HMD in their line of sight. Accordingly, as depicted a headband 2310 runs around the sides and front of a user's head and has an adjustment 2320 at the rear for tightening the NR2I-HMD for different users. Disposed at the front of the headband 2330 is a Slider Assembly 2330 allowing the vertical position of the NR2I Housing 2340 to be adjusted for the user when in use as well as allowing it to be transitioned to a position where the NR2I Housing 2340 is out of the user's line of sight. In this embodiment of the invention any optical imaging devices, optical sources, IR emitters, optical scanners etc. are disposed within the portion of the NR2I Housing 2340 at the lower middle behind the Window 2345.

The NR2I Housing 2340 may further be adjusted as described above to provide different accommodation distances to the user. Optionally, the Slider Assembly 2330 may, within another embodiment of the invention, be replaced with a fixed mounting or adjusted and fixed so that no subsequent vertical adjustment is provided.

Referring to FIG. 2T there is depicted the bioptic immersive NR2I-HMD according to an embodiment of the invention depicted in FIG. 2S with the front cover of the NR2I Housing removed to show thermal management aspects of the NR2I display portion of the NR2I-HMD. Accordingly, a Cover 2370 is shown detached from the Housing Body 2350. The outer surface of the Housing Body 2370 being a Grid/Ribbed Structure 2360 allowing air flow through the upper surface of the Housing Body 2370 as well as around the front of the Housing Body 2370 as the Cover 2370 in combination with the Grid/Ribbed Structure 2360 provides for air flow between the Housing Body 2350 and the Cover 2370.

The Housing Body 2350 may be formed from a lightweight thermally conductive material such as aluminium, a metal, an alloy, a ceramic, a thermally conductive plastic or a combination of such materials or two or more thermally conductive plastics. In addition to the Grid/Ribbed Structure 2360 providing a heat-sink it would be evident that the structure through the ribs etc. can act as heat-pipes to provide high thermal conductivity from the front/side portions of the heat-sink to the upper surface, for example.

Within embodiments of the invention portions of the HMDs containing a battery or batteries may be detachable allowing for these to be swapped. Optionally, a battery permanently disposed within the HMD may provide sufficient short-term power to allow for "hot swapping" of the battery or where two or more battery assemblies are employed then one may be removed whilst the other maintains power to the HMD.

Within another embodiment of the invention a HMD may also include an electrical interface supporting a demountable memory device such as a memory card, USB memory device, etc. allowing configuration information, personalization etc. for the HMD to be stored within the demountable memory device such that multiple users can employ the same HMD wherein each has a demountable memory device they connect to establish configuration information, personalization etc. Alternatively, the HMD extracts this from a PED and/or FED to which the HMD is paired through a wireless interface such that pairing the HMD with another PED and/or FED results in the new configuration/personalization information being extracted and employed by it.

Within the NR2I HMDs depicted and described in respect of FIGS. 2G to 2T the Slider Housing 2130 may have a curved forward facing surface against which the rear surface of Slider 2140 moves. This rear surface may be similarly curved or alternatively contact the Slider Housing 2130 at a predetermined number of points. Accordingly, where the Slider Housing 2130 is curved the vertical motion of the Slider 2140 results in the NR2I-Housing 2150 rotating such that the NR2I-Housing 2150 describes an arcuate motion as it traverses from one extreme of its range to the other extreme of its range. The subsequent motion of the HMD Housing forward/backwards to provide the required accommodation is a linear slide although within another embodiment of the invention this may also be profiled to provide vertical motion in combination with horizontal motion.

Within the embodiments of the invention described and depicted in respect of the Figures the NR2I display(s)/system(s) have dual optical trains, one for each eye. Within other embodiments of the invention the NR2I display(s)/system(s) may be designed/configured for a single eye, e.g. the user's left or right, or may be configured in split design allowing the use of either one of or both of left and right elements. Optionally, a bioptic NR2I may provide a single element lifting into/out of the line of sight or it may provide one or two elements for left/right or left and right eyes individually. Also attached to the frame is a headband 180 such as depicted in FIG. 1A and as described within World Patent Application PCT/CA2016/000,189 filed Jul. 6, 2016 entitled "Methods and Devices for Demountable Head Mounted Displays." This provides additional support such that the NR2I display load is not all directly borne by the user's nose and ears. The headband 180 may be attached using attachment clips. An additional strap may be attached around the rear of the user's head and attach via the same attachment clips as the headband 180 or via different attachment clips. Optionally, the rear strap may attach at the ends of the arms of the frame that project along the side of the user's head either behind their ears, proximate the ears, in front of their ears or proximate their temples etc.

The NR2I display may include one or more image capture devices such image sensor 120 in FIG. 1B, this being for example a CCD camera. For example, in a typical configuration the NR2I display would include a camera (image sensor) 120 facing forward although in other embodiments of the invention two or more cameras may be integrated with different viewpoints relative to the user's line of sight, e.g. forward, lateral, rear, etc. Optionally, these cameras may be at different tilt angles relative to the body of the NR2I such that, for example, a forward-facing camera 120 is normally employed but the user can swap to a camera pointing down or substantially down. Optionally, a visible camera and an infrared (IR) camera may be integrated allowing the user in some applications to view thermal imagery as well as their normal sight. Within embodiments of the invention the micro-displays within the NR2I may display information acquired from the camera(s) and/or one or more other sources of content including, but not limited to, other cameras, video cameras, web content, documents, streaming video, etc.

Figure 3:
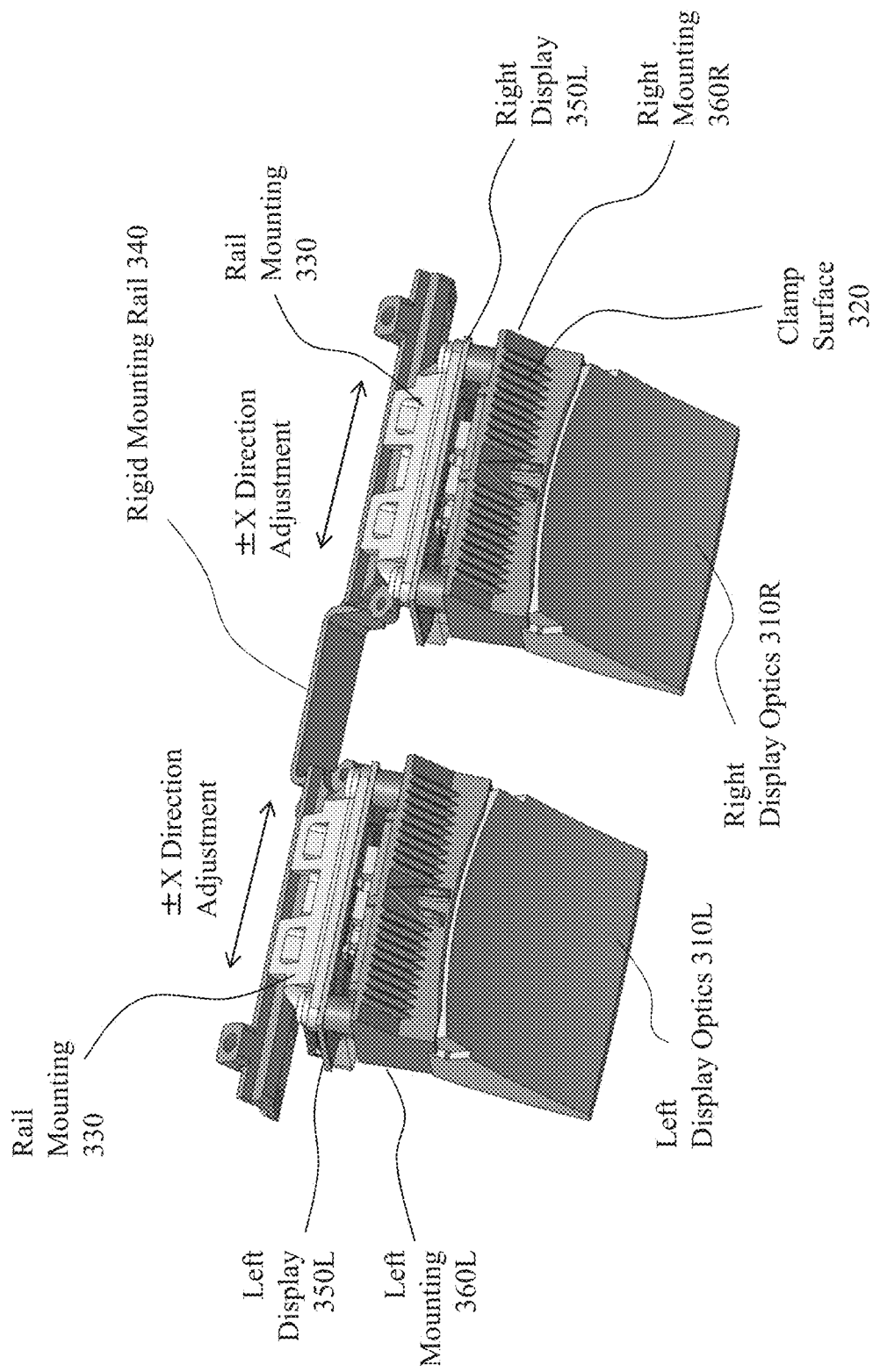
FIG. 3 depicts an optical sub-assembly within an exemplary NR2I-HMD according to an embodiment of the invention allowing the structure of the optical sub-assembly (optical train) to be viewed with the pair of individually movable freeform lenses and the display mounted to each.

Optionally, the NR2I display may include one or more eye and/or pupil tracking sensors with their associated electronics either forming part of the NRI display electronics by design or by addition. Referring to FIG. 3 there is depicted an optical sub-assembly within an exemplary NR2I-HMD according to an embodiment of the invention allowing the structure of the optical sub-assembly (optical train) to be viewed with the pair of individually movable freeform lenses and the display mounted to each. Accordingly, a binocular configuration for a Display Optics Sub-Assembly is depicted wherein a Left Display 350L is coupled to a Left Display Optics 310L via Left Mounting 360L. Similarly, a Right Display 350R is coupled to a Right Display Optics 310R via Right Mounting 360R. Each of these assemblies being slidably mounted to a Rigid Mounting Rail 340 via a Rail Mounting 330. Within the configuration shown the positions of the left and right assemblies are locked when the Display Optics Sub-Assembly is mounted within the body of the Demountable Display Assembly 110 portion of the NR2I and a plate or plates clamped against the Clamp Surfaces 320 thereby restricting the ±X direction movement of the optical sub-assemblies once assembled. As depicted each of the left and right portions can be set individually whilst in another embodiment, they may be linked such that moving one moves the other in the opposite direction such that the IPD increases/decreases equally centered upon a center point of the Display Optics Sub-Assembly which for example is referenced to the centre of the user's nasal bridge through the mechanical structure of the Demountable Display Assembly 110.

It would be evident that the other axes of configuring the NR2I may be established based upon other physical portions of the Demountable Display Assembly 110 referencing with respect to the user's nasal bridge, for example, if the Demountable Display Assembly 110 or Frame includes a Nose Bridge Assembly. This Nose Bridge Assembly may establish the height of the Demountable Display Assembly 110 relative to the user's nose as well as the depth in the Z dimension. If the Nose Bridge Assembly is part of the frame, then the Demountable Display Assembly 110 would through its attachment points be positioned appropriately each time the Frame and Demountable Display Assembly 110 are assembled for that user.

As depicted in FIG. 3 the display is disposed above the user's eye line through the Left Display Optics 310L and Right Display Optics 310R. Alternatively, the assemblies might be rotated by 90° such that the Left Display Optics 310L and Right Display Optics 310R together with their Left Display 350L and Right Display 350R are all disposed horizontally with respect to the user's eyeline. A similar Rigid Mounting Rail 340 with modified Rail Mounting 330 may still be employed or alternatively a different mechanical configuration may be employed.

Figures 4A, 4B:
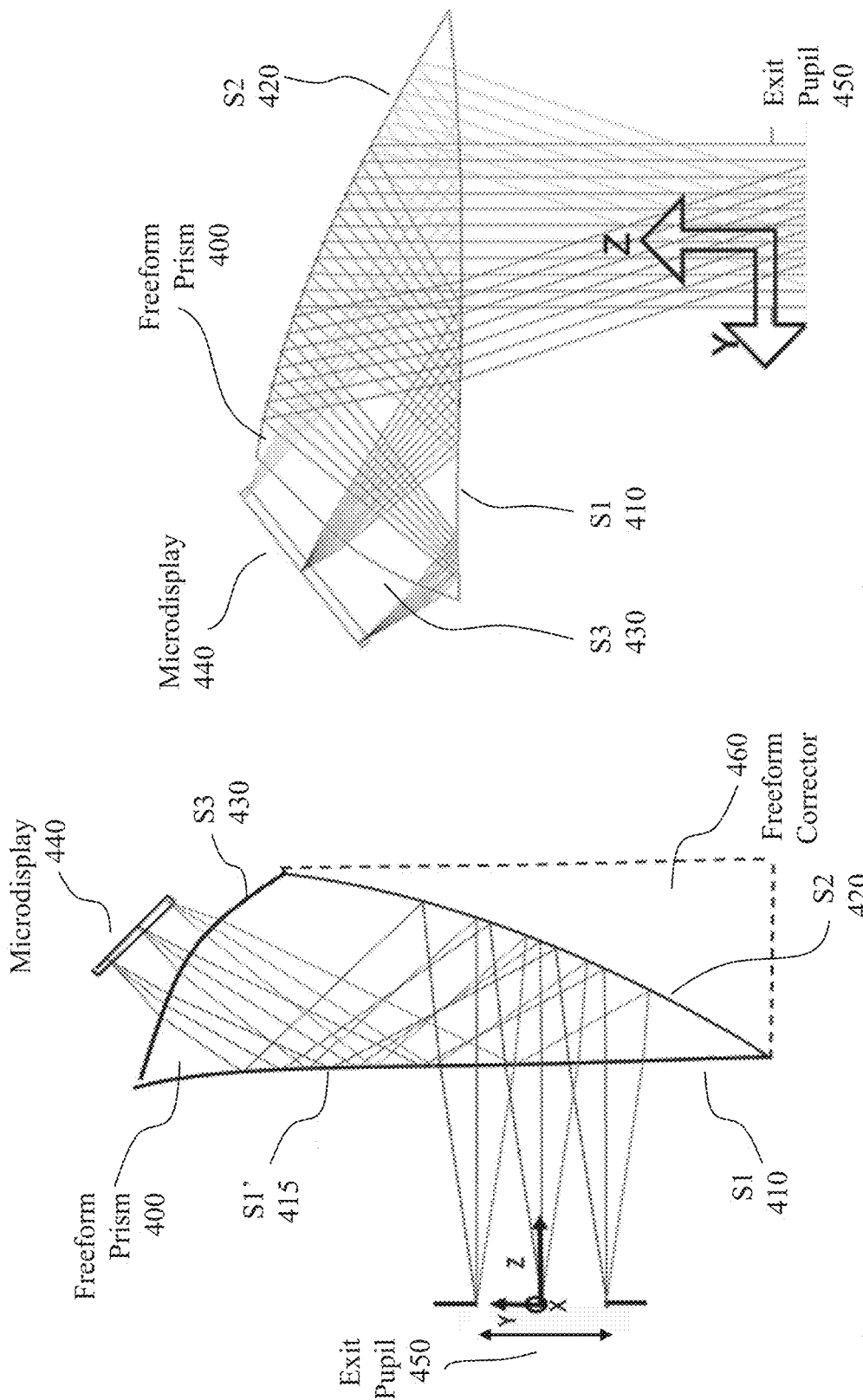
FIG. 4A depicts a freeform lens assembly according to an embodiment of the invention with the display laterally mounted to the left and right temples of the user for the left and right eyes respectively.
FIG. 4B depicts a freeform lens assembly according to an embodiment of the invention with the display vertically mounted above the left and right eyes of the user for the left and right eyes respectively.

Referring to FIG. 4A there is depicted a schematic layout of a typical Freeform Prism 400 design consisting of three optical surfaces, labelled as S1 410, S2 420, and S3 430. The freeform prism-lens 400 serves as the NR2I viewing optics that projects, and optionally magnifies, the image displayed on a MicroDisplay 440 to the user's vision. For the sake of convenience, the surface adjacent to the exit pupil is labeled as S1 410 in the refraction path and as S1' 415 in the reflection path. The center of the exit pupil 450 may be set by the inventors as the origin of the global coordinate system and the surfaces are specified with respect to this global reference. The inventors have further adopted the convention of tracing the system backward, namely from the eye position to the MicroDisplay 440. The overall system was set to be symmetric about the YOZ plane, but not the XOZ plane as common within the prior art. In FIG. 4A the Z-axis is along the viewing direction, X-axis is parallel to the horizontal direction aligning with inter-pupillary direction, and the Y-axis is in the vertical direction aligning with the head orientation. Accordingly, an optical "ray" emitted from a point on the MicroDisplay 440 is refracted first by the surface S3 130 disposed towards the MicroDisplay 440. After two consecutive reflections by the surfaces S1' 115 and S2 120, this ray is transmitted through the surface S1 110 and reaches the exit pupil 150 of the system. To enable optical see-through capability, an auxiliary lens, referred to as a freeform corrector 460, may be coupled and/or cemented to the wedge-shaped freeform prism-lens 400 in order to minimize the ray shift and distortion introduced to the rays from a real-world scene.

A freeform prism-lens typically is symmetric about the plane in which the surfaces are rotated and decentered and the optical path is folded. For instance, the prism-lens schematic in FIG. 4A was set to be symmetric about the vertical YOZ plane. The optical surfaces are decentered along the vertical Y-axis and rotated about the horizontal X-axis so that the optical path is folded in the vertical YOZ plane to form a prism-lens structure. With this type of plane-symmetry structure, it is very challenging to achieve a wider field of view for the folding direction than the direction with symmetry. Accordingly, prior art freeform prism-lenses typically fold the optical path in the direction corresponding to the direction of narrower FOV as shown in FIG. 4A, which makes it easier to achieve total internal reflection (TIR) in surface S1' 415 and maintain a valid prism-lens structure. As most display applications typically prefer a landscape-type display, then NR2I systems typically align the wider FOV direction horizontally and the narrower FOV direction vertically. As a result, most of the freeform prism-lens-based NR2I optical systems mount the microdisplays above the user's eyebrow(s), which leads to a front-heavy system and compromises overall ergonomic design.

Accordingly, it would be evident that the freeform prism-lens 400 designs that fold the optical path along the wider FOV direction allow for mounting of the microdisplays on the temple sides of the user and mitigate ergonomic challenges. In the prior art, there are instances of freeform prism-lens designs folded in the direction corresponding to the wider FOV. However, such prior art designs exploiting microdisplays which were both larger (18 mm, 0.7" diagonal) overall and with larger pixels (~15 μm) and yielded optical trains for NR2I systems that had smaller exit pupil and inferior ergonomics and usability than that targeted by embodiments of the present invention.

For users exploiting NR2I systems to overcome vision degradation etc. then the user is looking at longer periods of use than common within the commonly touted application of NR2I displays in gaming systems and/or vision augmentation at work. Potentially, the user is wearing them all their waking day, e.g. 15, 16, 17 hours a day, 7 days a week, and 365 days a year. In this environment large exit pupil and effective ergonomics are important for comfort, usability, etc.

Referring to FIG. 4B respectively there is depicted a 2D optical layout of a freeform prism-lens absent any auxiliary optical elements as can be employed within the NR2I system according to an embodiment of the invention. A ray emitted from a point on the MicroDisplay 440 is first refracted by the surface S3 430 next to the MicroDisplay 440. After two consecutive reflections by the surfaces S1' 415 and S2 420, the ray is transmitted through the surface S1 410 and reaches the exit pupil 450 of the system. The first surface (i.e., S1 410 and S1' 415) of the prism-lens is required to satisfy the condition of total internal reflection for rays reflected by this surface S1' 415. The rear surface S2 420 of the prism-lens may, optionally, be coated with a mirror coating for immersive NR2I systems thereby blocking the user's view of the real-world scene except as presented upon the MicroDisplay 440. Alternatively, the surface S2 420 may be coated with a beam-splitting coating if optical see-through capability is desired using the auxiliary lens (not shown for clarity). The coating on surface S2 may be wavelength-selective, for example with a wavelength transfer-function as shown in FIG. 12, to allow the passing of infra-red light, while reflecting visible light.

It should be noted that in the design disclosed according to an embodiment of the invention is presented with the global reference coordinate system centered with respect to the exit pupil, like most of the existing freeform prism-lens designs. However, the reference axes are set differently from the existing designs presented within the prior art. Here the Z-axis is along the viewing direction, but the Y-axis is parallel to the horizontal direction aligning with inter-pupillary direction, and the X-axis is in the vertical direction aligning with the head orientation. In other words, the reference coordinate system is rotated 90-degrees around the Z-axis. As a result, the overall prism-lens system is symmetric about the horizontal (YOZ) plane, rather than a typical left-right symmetry about the vertical plane. The optical surfaces (S1 410, S2 420, and S3 430) are decentered along the horizontal Y-axis and rotated about the vertical X-axis. As a result, the optical path is folded in the horizontal YOZ plane, corresponding to the direction of wider field of view, to form a prism-lens structure. This arrangement allows the MicroDisplay 440 to be mounted on the temple side of the user's head.

Referring to FIG. 5 there is depicted a freeform prism-lens according to the embodiments of the invention depicted in respect of FIGS. 4A and 4B respectively. As depicted the surface adjacent to the exit pupil is labeled as S1 410 in the refraction path and as S1' 415 in the reflection path but is now depicted as being divided into three regions along these surfaces S1 410 and S1' 415 which are denoted as Region A 460, Region B 470, and Region C 480. Within Region A 460 all optical paths from the micro-display, for example MicroDisplay 440 in FIGS. 4A and 4B respectively, to the exit pupil, for example Exit Pupil 450 in FIGS. 4A and 4B respectively, are reflected by surface S1 410 and hence are defined by reflection paths on surface S1' 415. Within Region C 480 all optical paths from the MicroDisplay to the exit pupil are transmitted by surface S1 410 and hence are defined by refraction paths on surface S1 410. However, the middle region, Region B 470, the optical paths from the micro-display to the exit pupil are a combination of both those reflected by surface S1 410 and hence are defined by reflection paths on surface S1' 415 and those transmitted by surface S1 410 and hence are defined by refraction paths on surface S1 410.

Optionally, the NR2I display may include one or more eye and/or pupil tracking sensors with their associated electronics either forming part of the NRI display electronics by design or by addition. Such a configuration is depicted in FIG. 6 wherein the Freeform Prism-Lens 400 is depicted with a Freeform Corrector 460 and the MicroDisplay 440. In addition, there are depicted Near Infra-Red (NIR) LED 610 providing infra-red illumination of the user's eye and NIR Sensor 620 which provides NIR detection and spatial signal(s) such that the user's eye is tracked allowing this information to be used either in respect of modifying the image presented to the user, augmentation content provided to the user, etc. It would be evident that if spatial separation of the NIR optical signals from the visible signals from the MicroDisplay 140 can be achieved that placement of the NIR LED 610 and NIR Sensor 620 may be varied from that depicted of either side the MicroDisplay 440.

Optionally, disposed within the NR2I display is a light source/flashlight to provide illumination for the user. Optionally, two or more light sources/flashlights may be provided. Additionally, the NR2I system may include a range finder. As depicted in FIG. 1B such a range finder, second camera etc. may be fitted as depicted with first and second optical elements 140 and 150 respectively within the central portion of the NR2I display depicted in FIG. 1B. The NR2I display may communicate to another electronic device, e.g. a PED and/or FED, exploiting a wired and/or wireless link. A wired link may exploit industry standard or custom connector interfaces and/or communications standards.

NR2I displays may support a single or multiple display technologies according to the design of the NR2I display and the resulting specifications placed on the micro-display and therein the design and implementation of the freeform prism-lens. Accordingly, the micro-display(s) may be liquid crystal, e.g. Liquid Crystal on Silicon (LCOS), Light Emitting Diode (LED) based, or Organic Light Emitting Diode (OLED) technology. Within immersive embodiments of the invention the freeform prism-lens may be reflective by design and/or exploit a reflective coating. In transmissive embodiments of the invention the freeform prism-lens may be anti-reflection coated prior to assembly with additional optics such as the Freeform Corrector 160 in FIG. 1A. The visual image presented to the user may be the same, different, external view acquired with camera, or external content acquired from a PED/FED and/or remote source. For example, within an immersive NR2I system the image from the Camera 120 may be presented to both eyes whilst the user's left eye is presented with the digital content overlaid to the image and the user's right eye is not or vice-versa. Optionally, one eye of the user is presented with the image with or without digital content overlay whilst the other eye is presented with a modified image, such as with highlighted edges, for example. Within other embodiments of the invention with dual cameras, e.g. stereoscopic image acquisition, then the user is presented with left and right images with or without digital content overlay, image modification etc. If, for example, the user is employing a NR2I device with visible and infrared cameras or receiving dual camera feeds from visible and infrared cameras then these may be presented to the user in different eyes, for example.

Figure 7:
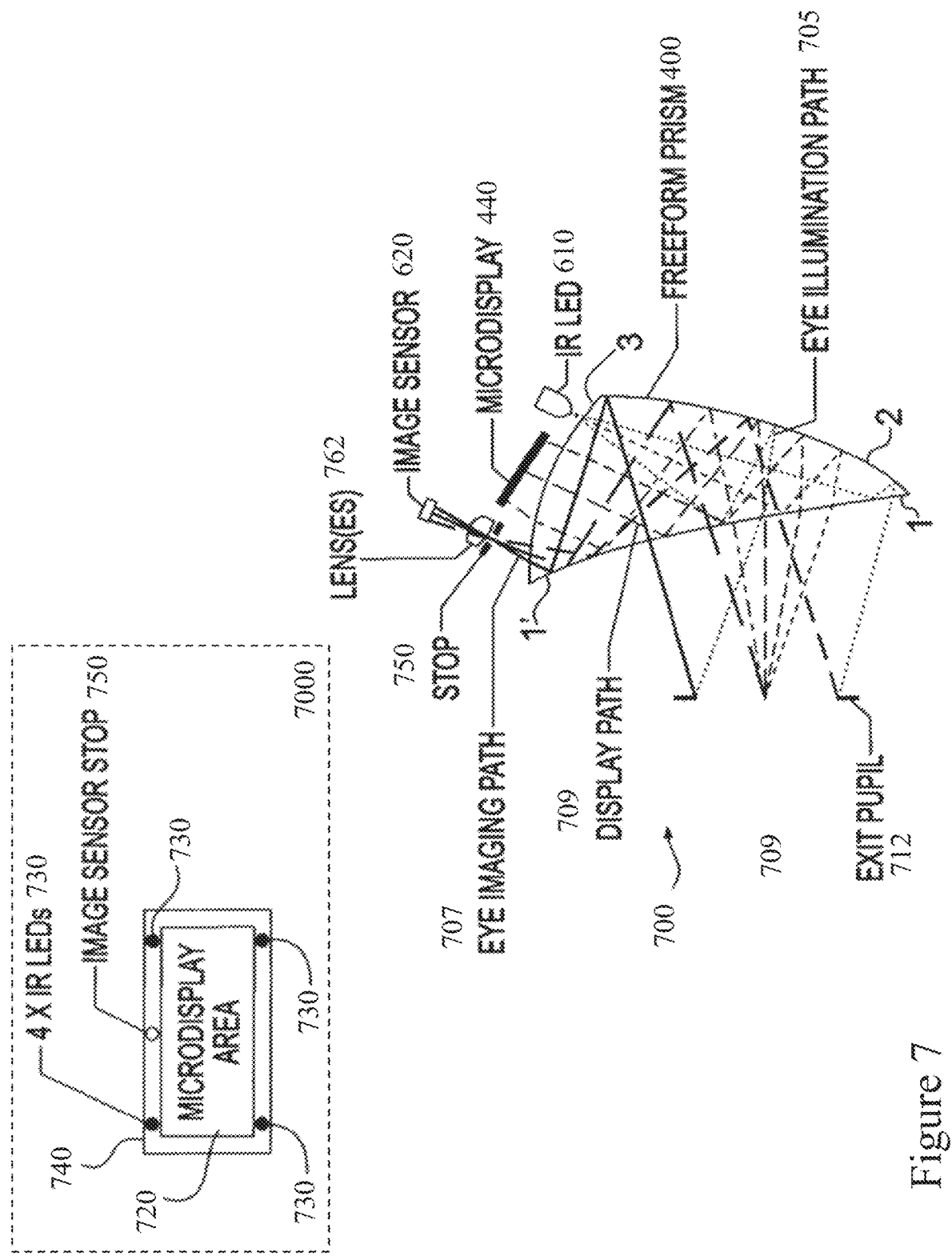
FIG. 7 depicts a freeform lens assembly according to an embodiment of the invention for an exemplary NR2I-HMD employing an infra-red LED and imaging sensor upon the same facet as the display element for determining the orientation of the user's eye relative to the freeform lens.

Now referring to FIG. 7 there is depicted a configuration for eye-tracking employing a wedge-shaped Freeform Prism 400 in conjunction with a MicroDisplay 440, a NIR LED 610 and NIR Image Sensor 620. In this embodiment, the Freeform Prism 400 is required to serve three core functions:

- as an illumination optic that collimates/transmits the light from one or multiple NIR LEDs 610 to locally or uniformly and non-invasively illuminate the eye area to be imaged;
- as the core element of an eye imaging optic that captures NIR-illuminated eye images using one or multiple NIR sensors (image sensors) 620 to enable eye movement tracking; and
- as an eyepiece optic of a NR2I-HMD system allowing the user to view images displayed on the MicroDisplay 440.

These three unique optical paths may be combined by the same Freeform Prism 400 to achieve the capabilities of eye tracking and display. Additionally, the same Freeform Prism 400 when coupled to, e.g. cemented, with a freeform corrective lens, e.g. Freeform Corrector 460, enables a transmissive or see-through capability for the NR2I-HMD system. Alternatively, Freeform Prism 400 may omit the core function as an illumination optic as described below in respect of FIG. 9, for example.

Accordingly, FIG. 7 schematically illustrates the integrated System 700 where the illumination, imaging and display optics comprise the same Freeform Prism 440 and the illumination LEDs 610 and a pinhole-like Stop 750 are placed around the edge of the MicroDisplay 440 to form a high-quality eye image. This being an example of the Stop 750 and NIR LED 610 configuration. The Stop 750 and LEDs 610 may be placed in other locations at the periphery around in the MicroDisplay 440 as depicted in inset 7000. In addition, the Stop 750 and NIR LEDs 610 may or may not be co-planar with the MicroDisplay 440. Additional lenses may be used in one or more of the illumination path 705, eye imaging path 707, and display path 709 to improve the system performance. Moreover, at the surface closest to the MicroDisplay 440, surface 3, the Illumination Path 505, Eye Imaging Path 507, and Display Path 509 may impinge upon differing respective portions of surface 3 although partial overlap is permitted. In subsequent images where only an IR sensor is shown, the optional presence of a stop 750 and/or lens(es) 762 may be provided but these are omitted for clarity within the subsequent Figures.

In order to support transmissive or see-through capability, surface 2 of the Freeform Prism 440 may be coated to provide a half mirror if total internal reflection of all rays for the Illumination Path 505, Eye Imaging Path 507, and Display Path 509 cannot be achieved. Coatings may be employed to provide selective filtering such as shown in FIG. 12. Optionally, in some embodiments of the invention in order to ease the design constraint a coating reflective to the NIR signals may be deposited upon surface 2 of the Freeform Prism 440 so that the total internal reflection criterion to avoid half-mirroring for the Display Path 709. The rays from the MicroDisplay 440 may be reflected by the surface 2 while the rays from a real-world scene are transmitted. As depicted in FIG. 6 a Freeform Corrector 460 comprising two freeform surfaces is cemented or otherwise mechanically and optically coupled/combined with the Freeform Prism 440 to correct the viewing axis deviation and aberrations introduced by the Freeform Prism 440 to the real-world view path (not shown for clarity). Typically, to allow the Freeform Corrector 460 to be cemented against surface 2 of the Freeform Prism 440 then the surface of the Freeform Corrector 460 against the Freeform Prism 440 is designed to have the same geometry as surface 2 of the Freeform Prism 440 and whilst the other surface of the Freeform Corrector 460 is optimized to correct for axis deviation, optical aberrations etc. The Freeform Corrector 460 generally does not significantly increase the footprint or weight of the overall system. Overall, the exemplary System 700 provides a lightweight, compact, robust, and eye tracked NR2I-HMD solution with an unobtrusive form factor.

Figure 8:
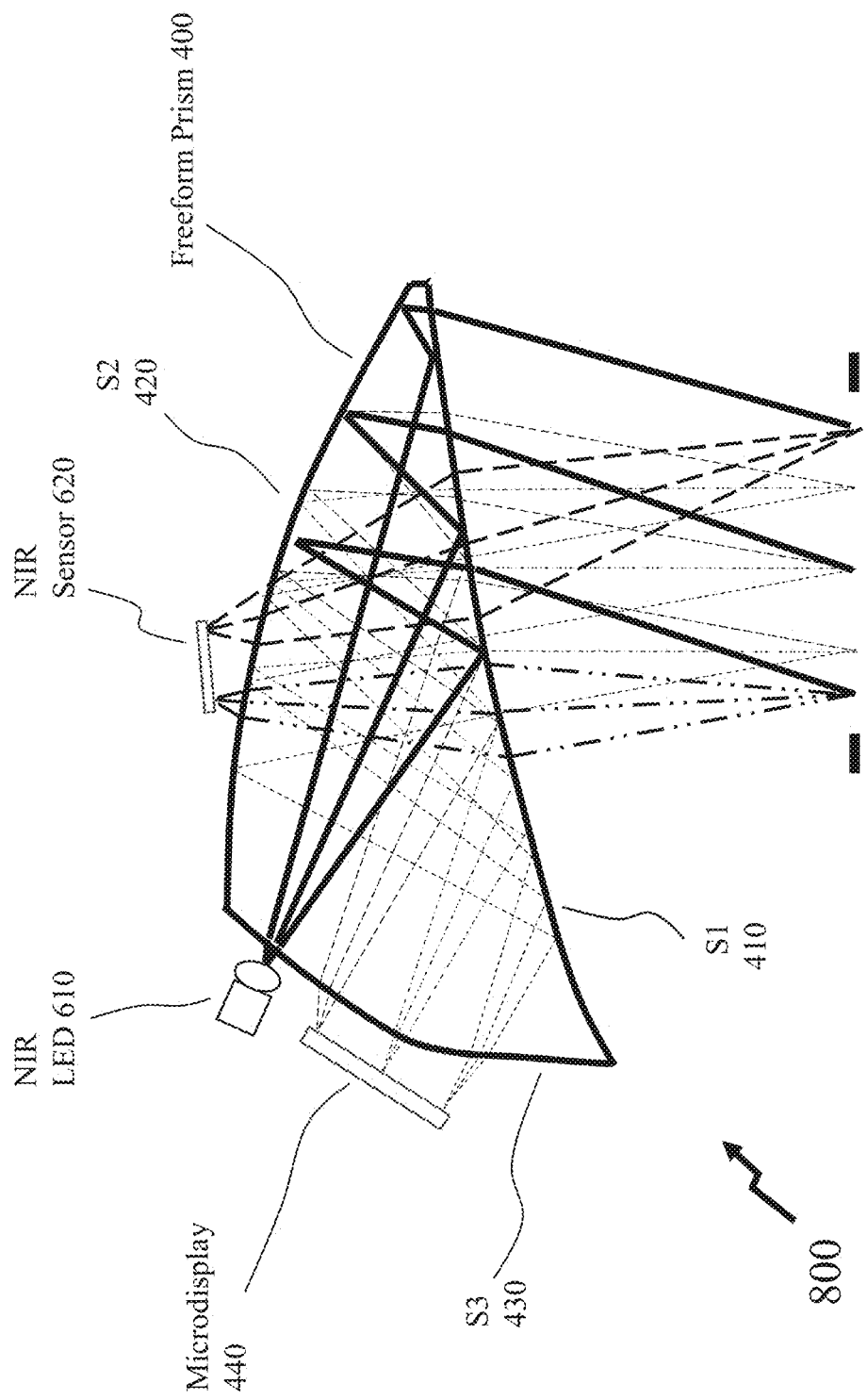
FIG. 8 depicts a freeform lens assembly according to an embodiment of the invention for an exemplary NR2I-HMD employing an infra-red LED and imaging sensor upon different facets of the freeform lens for determining the orientation of the user's eye relative to the freeform lens.

Now referring to FIG. 8 there is depicted a System 800 again comprising a Freeform Prism 400 together with MicroDisplay 440, NIR LED 610 and NIR Sensor 620. In this embodiment the NIR LED 610 and MicroDisplay 440 are disposed relative to surface S3 430 whilst the NIR sensor 620 is disposed relative to surface S2 420. As depicted the Freeform Prism 400 is horizontal supporting a wide lateral field of view (FOV). Both the NIR LED 610 and MicroDisplay 440 are reflected twice by the Freeform Prism 400 whereas the NIR Sensor 620 receives signals reflected from the wearer's eyes by direct transmission through the surfaces S2 420 and S1 410 of the Freeform Prism. As depicted, there is no lensing or pinhole applied to the NIR Sensor 620. In an immersive NR2I system the surface S2 420 may be coated to be reflective in the visible spectrum and transmissive in the NIR. In other embodiments according to the placement of the NIR LED 610 and design of the NIR Sensor 620 the NR2I may be transmissive with no coating on the surface S2 420 or a partially reflecting visible coating.

Figure 12A:
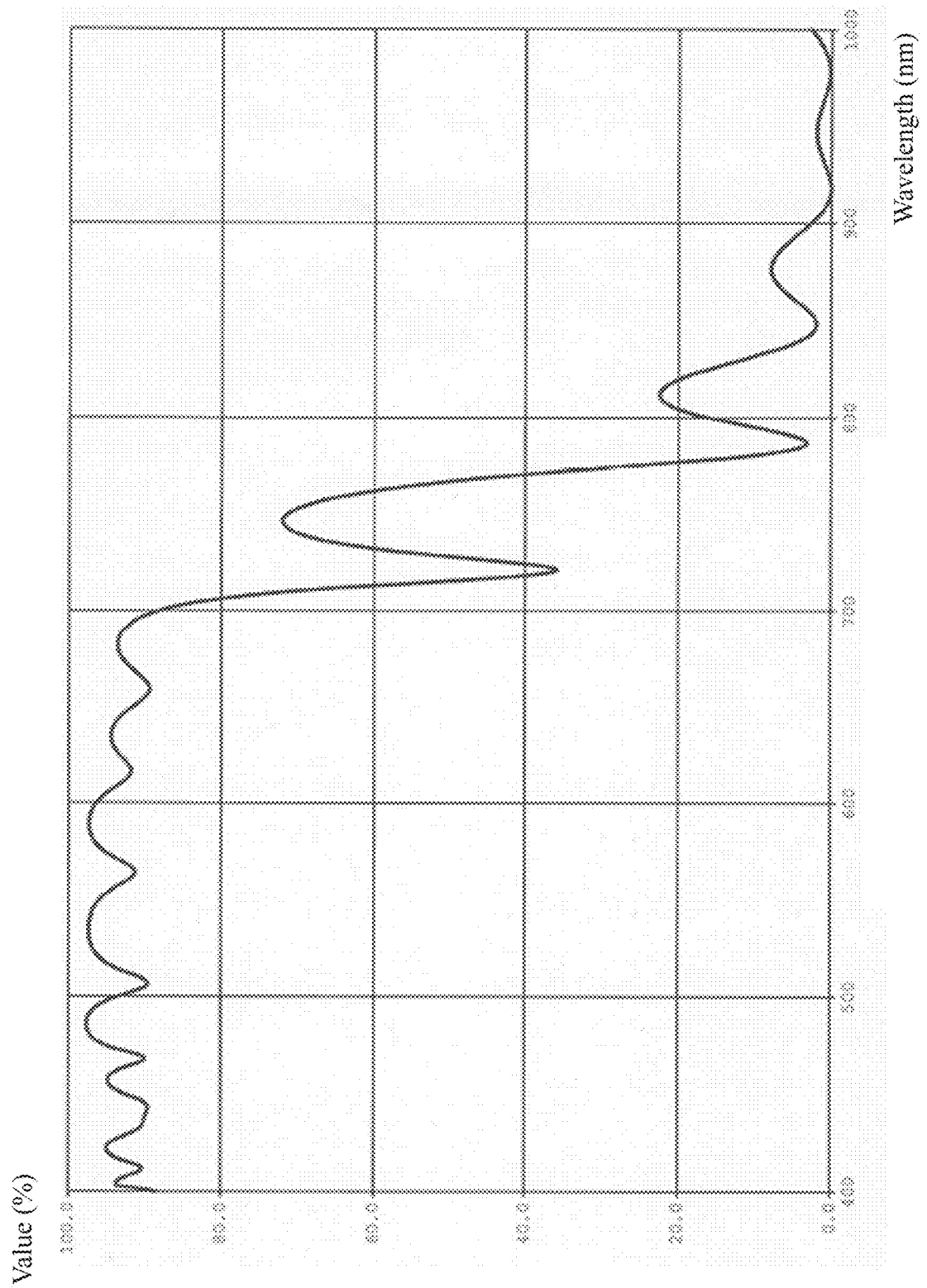
FIG. 12A depicts an exemplary transmission or reflection characteristic for a coating applied to a freeform lens assembly according to an embodiment of the invention for an exemplary NR2I-HMD employing multiple sources of NIR directly and indirectly coupled to the user's eye together with an imaging sensor for determining the orientation of the user's eye relative to the freeform lens.
Figure 12B:
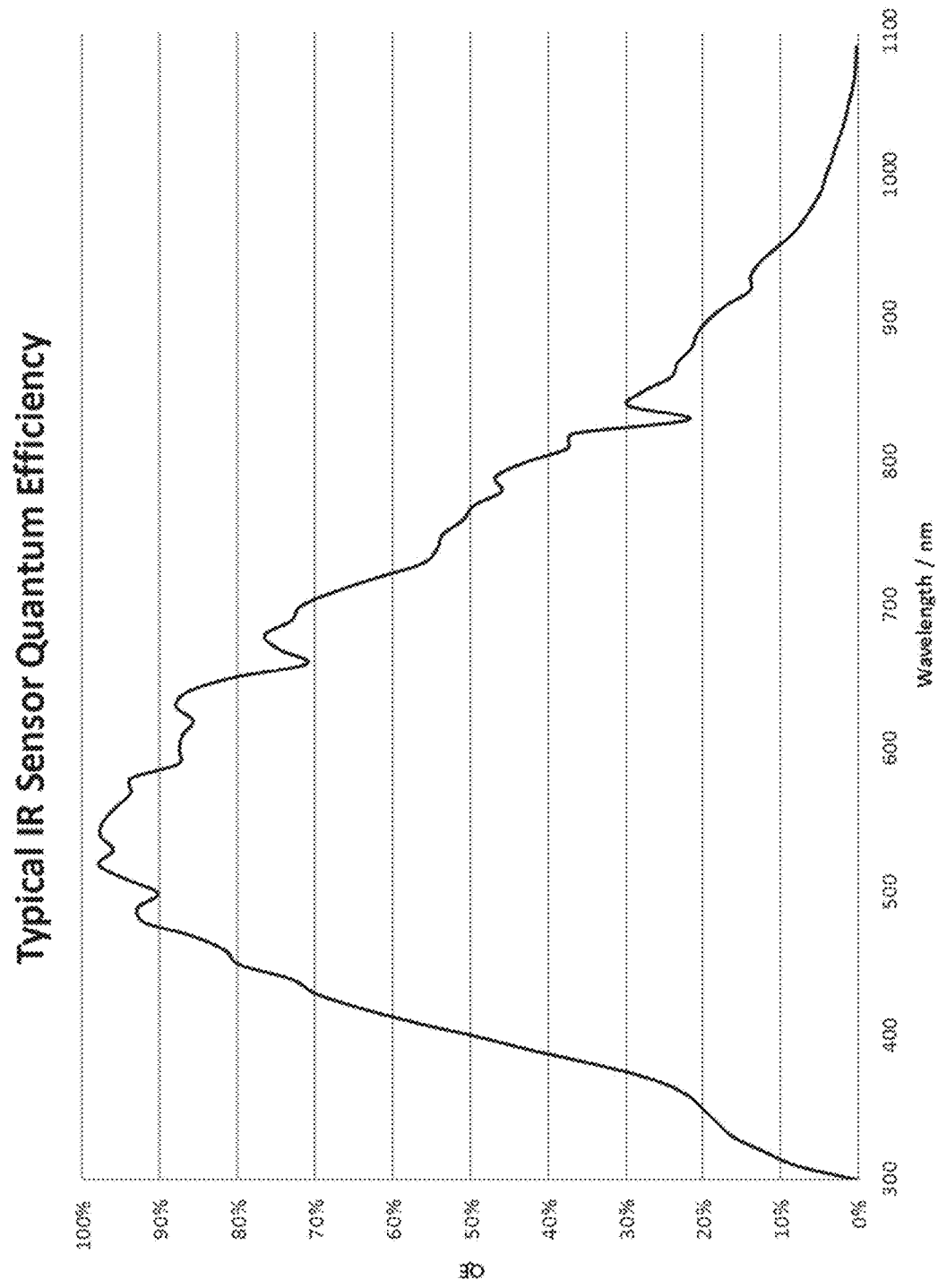
FIG. 12B depicts a typical IR image-sensor quantum-efficiency-curve.

Optionally, the NIR Sensor 620 may be disposed at the far left or at the far right, or top or bottom of the prism to allow clear forward viewing with an external corrector applied. Optionally, a pinhole lens may be applied for the NIR Sensor 620 as may a micro-lens. Optionally, NIR LEDs could be integrated into the MicroDisplay 440 through monolithic integration or hybrid integration. Where a wavelength-selective coating is used to allow simultaneous infra-red transmission and visible-reflection or vice-versa, the choices of IR emitter and filter corner-frequency in combination with the quantum efficiency curve of the infra-red image sensor used to image the eye is critical to overall system performance. A typical IR image-sensor quantum-efficiency-curve is shown in FIG. 12B. Note that the efficiency of the sensor improves dramatically as one approaches the shorter more energetic wavelengths of visible light. By illuminating the user's eye using IR emitters closer to the 790-900 nm region rather than above 900 nm, though there is additional loss through the filter-coating as shown in FIG. 12A, this can be more than made up by exploiting the improved quantum efficiency of the sensor as these shorter wavelengths. In a preferred embodiment, IR sources in the 790-900 nm spectrum are employed for this reason.

Figure 9:
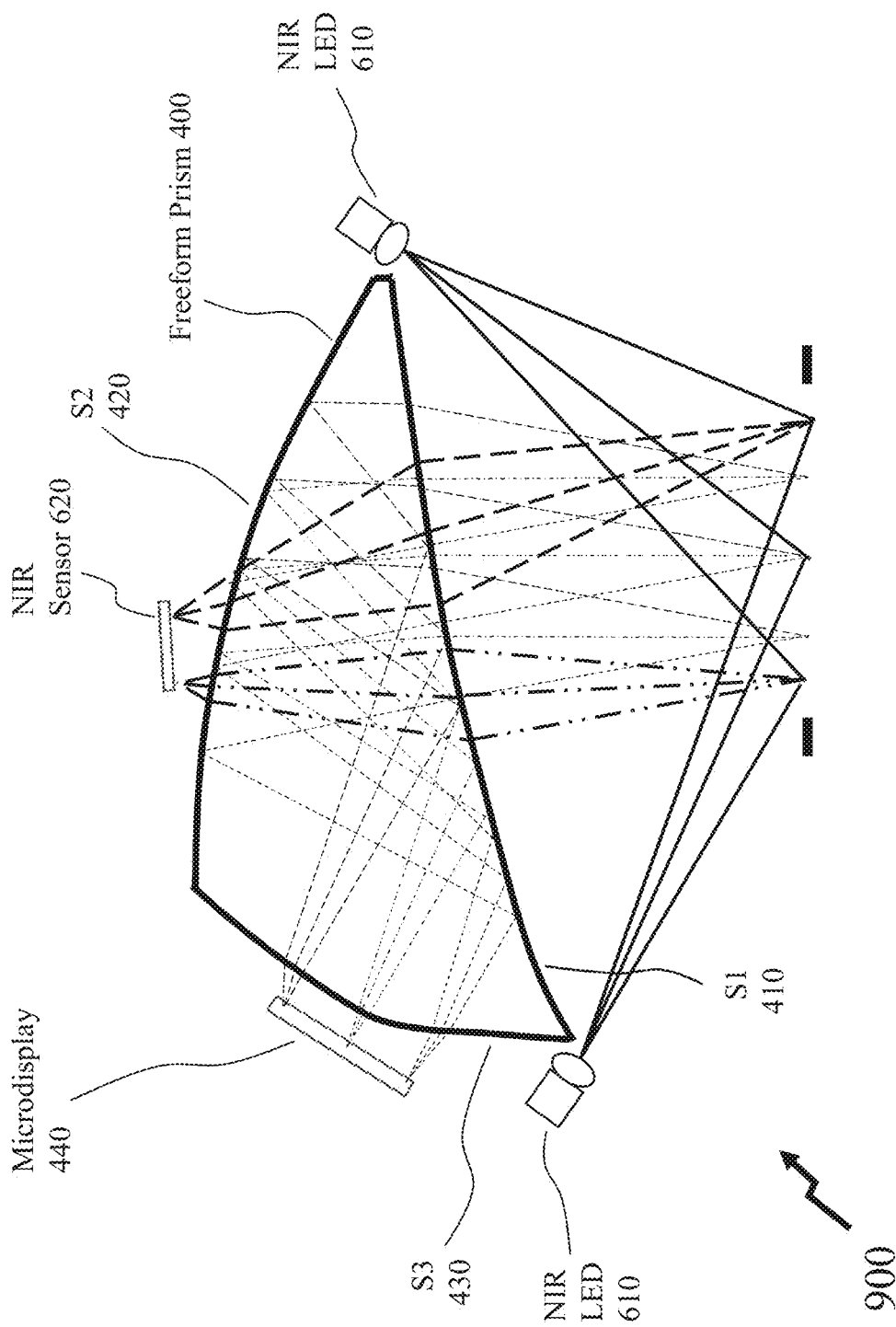
FIG. 9 depicts a freeform lens assembly according to an embodiment of the invention for an exemplary NR2I-HMD employing multiple infra-red LEDs laterally disposed relative to the user's eye and an imaging sensor upon the rear facet of the freeform lens for determining the orientation of the user's eye relative to the freeform lens.

Now referring to FIG. 9 there is depicted a System 900 again comprising a Freeform Prism 400 together with MicroDisplay 440, NIR LED 610 and NIR Sensor 620. In this embodiment the NIR LED 610 and MicroDisplay 440 are disposed relative to surface S3 430 whilst the NIR sensor 620 is disposed relative to surface S2 420. As depicted the Freeform Prism 400 is horizontal supporting a wide lateral field of view (FOV). In System 900 the NIR LEDs 610 are not transmitted through the Freeform Prism 400 to the user's eye(s) whereas MicroDisplay 440 is reflected twice by the Freeform Prism 400. The NIR Sensor 620 receives signals reflected from the wearer's eyes by direct transmission through the surfaces S2 420 and S1 410 of the Freeform Prism. As depicted, there is no lensing or pinhole applied to the NIR Sensor 620 though this is within the scope of invention. In an immersive NR2I system the surface S2 420 may be coated to be reflective in the visible spectrum and transmissive in the NIR. In other embodiments according to the placement of the NIR LED 610 and design of the NIR Sensor 620 the NR2I may be transmissive with no coating on the surface S2 420 or a partially reflecting visible coating.

Optionally, the NIR Sensor 620 may be disposed at the far left or at the far right to allow clear forward viewing with an external corrector applied. Optionally, a pinhole lens may be applied for the NIR Sensor 620 as may a micro-lens. Optionally, NIR LEDs could be integrated into the MicroDisplay 440 through monolithic integration or hybrid integration.

Figure 10:
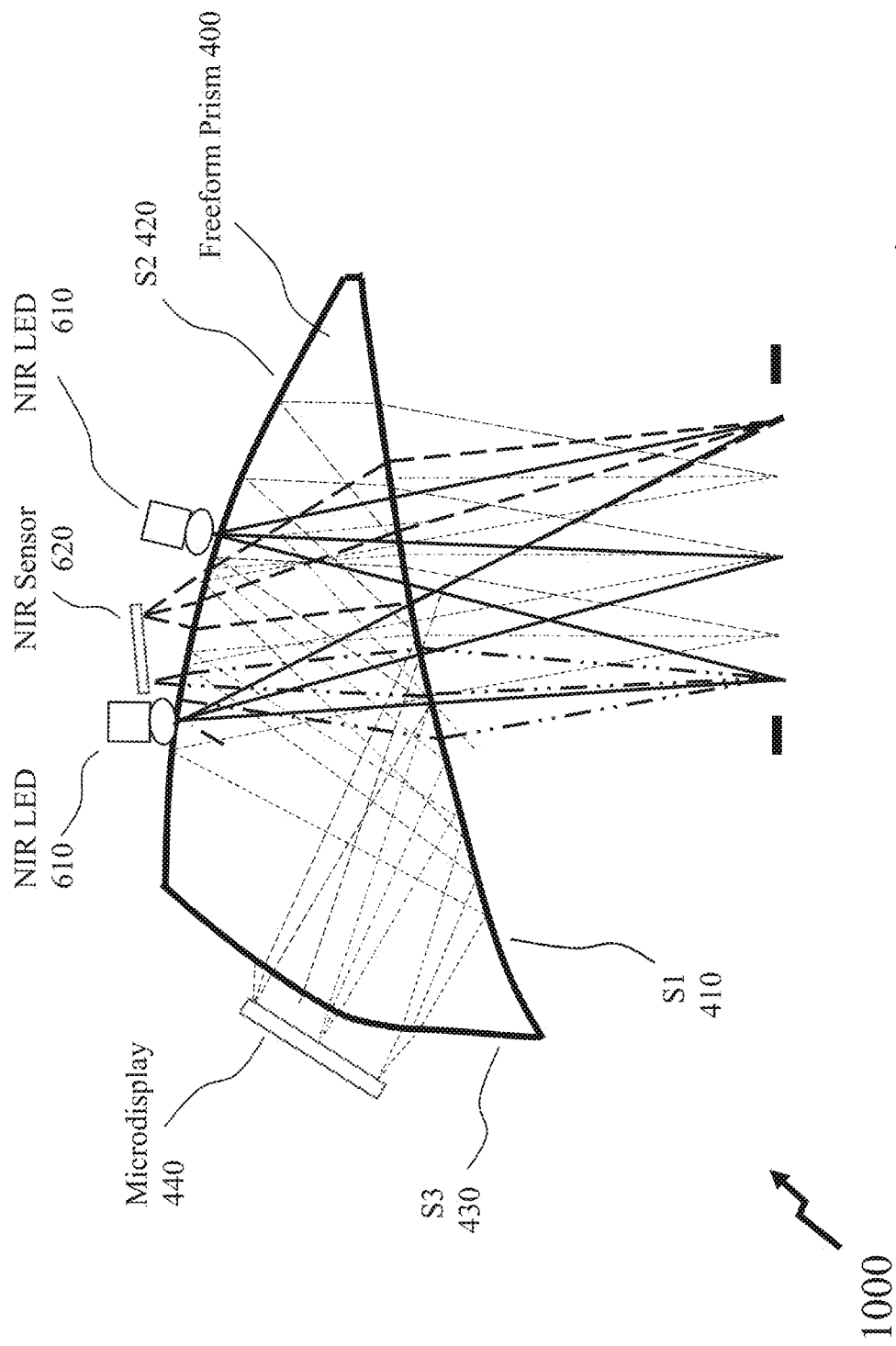
FIG. 10 depicts a freeform lens assembly according to an embodiment of the invention for an exemplary NR2I-HMD employing multiple near infra-red (NIR) LEDs laterally disposed upon the rear facet of the freeform lens together with an imaging sensor upon the rear facet for determining the orientation of the user's eye relative to the freeform lens.

Now referring to FIG. 10 there is depicted a System 1000 again comprising a Freeform Prism 400 together with MicroDisplay 440, NIR LED 610 and NIR Sensor 620. In this embodiment the NIR LEDs 610 and NIR Sensor 620 are disposed relative to surface S2 420 whilst the MicroDisplay 440 is disposed relative to surface S3 430. As depicted the Freeform Prism 400 is horizontal supporting a wide lateral field of view (FOV). In System 1000 the NIR LEDs 610 are transmitted through the Freeform Prism 400 to the user's eye(s) without reflection(s) whereas the MicroDisplay 440 is reflected twice by the Freeform Prism 400. The NIR Sensor 620 receives signals reflected from the wearer's eyes by direct transmission through the surfaces S2 420 and S1 410 of the Freeform Prism. As depicted, there is no lensing or pinhole applied to the NIR Sensor 620. In an immersive NR2I system the surface S2 420 may be coated to be reflective in the visible spectrum and transmissive in the NIR. In other embodiments according to the placement of the NIR LED 610 and design of the NIR Sensor 620 the NR2I may be transmissive with no coating on the surface S2 420 or a partially reflecting visible coating.

Optionally, the NIR LEDs 610 may be disposed at the far left or at the far right to allow clear forward viewing with an external corrector applied. Optionally, a pinhole lens may be applied for the NIR Sensor 620 as may a micro-lens. Optionally, NIR LEDs could be integrated into the MicroDisplay 440 through monolithic integration or hybrid integration. The design may optionally employ a single NIR LED 610, multiple NIR LEDs 610.

Figure 11:
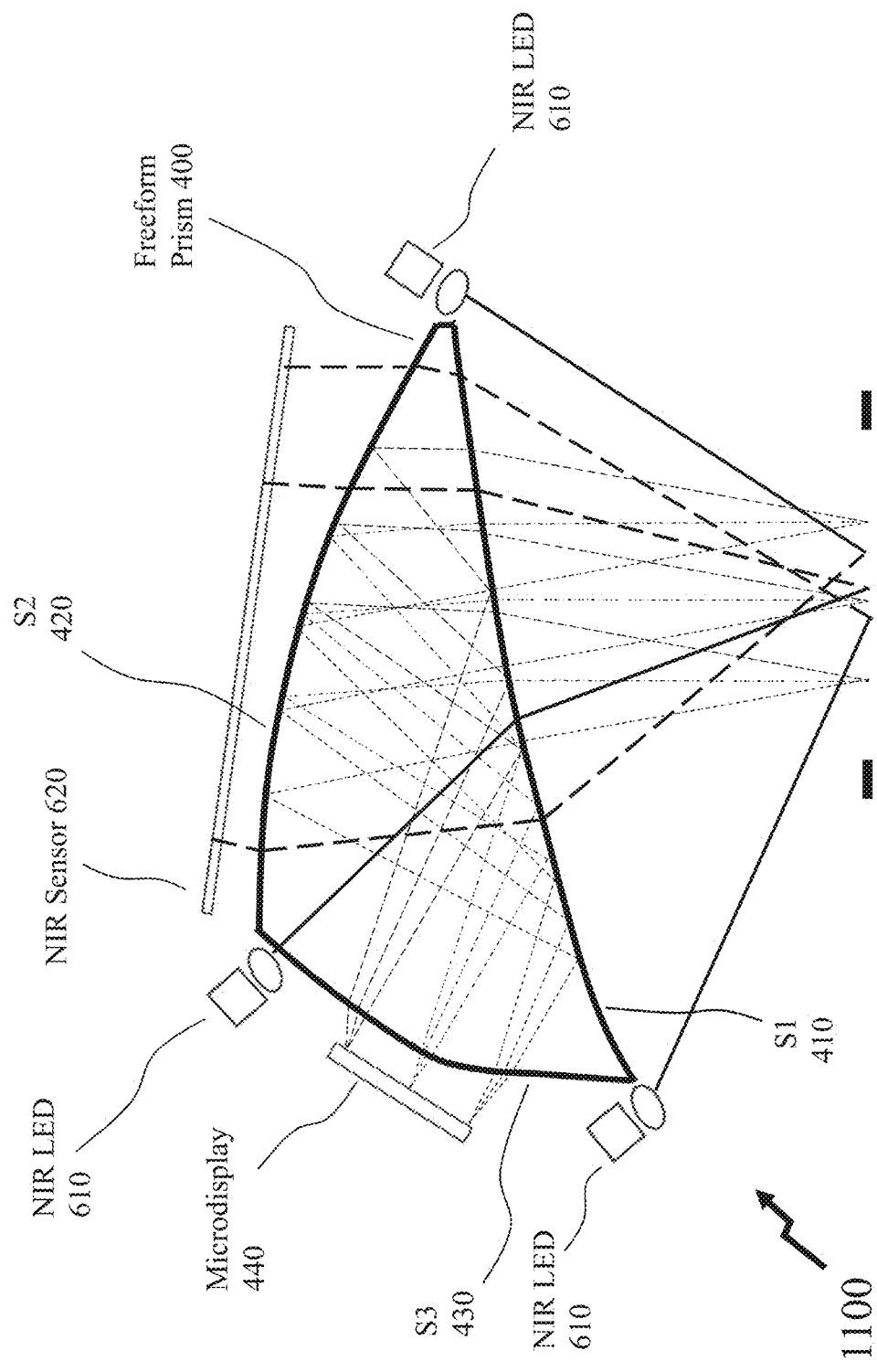
FIG. 11 depicts a freeform lens assembly according to an embodiment of the invention for an exemplary NR2I-HMD employing multiple sources of NIR structured light directly and indirectly coupled to the user's eye together with an imaging sensor upon the rear facet for determining the orientation of the user's eye relative to the freeform lens.

Now referring to FIG. 11 there is depicted a System 1100 again comprising a Freeform Prism 400 together with MicroDisplay 440, NIR LED 610 and NIR Sensor 620. As depicted in this embodiment the NIR LEDs 610 are disposed at different points and project both directly to the user's eye and through the Freeform Prism 440. As depicted the NIR Sensor 620 is disposed across the majority of the lateral width of surface S2 420 whilst the MicroDisplay 440 is disposed relative to surface S3 430 in common with the other embodiments of the invention depicted in FIGS. 7 to 10 supra. As depicted the Freeform Prism 400 is horizontal supporting a wide lateral field of view (FOV). The NIR Sensor 620 receives signals reflected from the wearer's eyes by direct transmission through the surfaces S2 420 and S1 410 of the Freeform Prism. As depicted, there is no lensing or pinhole applied to the NIR Sensor 620 but may be present. In an immersive NR2I system the surface S2 420 may be coated to be reflective in the visible spectrum and transmissive in the NIR. In other embodiments according to the placement of the NIR LED 610 and design of the NIR Sensor 620 the NR2I may be transmissive with no coating on the surface S2 420 or a partially reflecting visible coating.

Accordingly, with multiple directed IR signals from the NIR LEDs 610 the NIR sensor 620 can establish spatial positions for multiple IR signals simultaneously. If each NIR LED 610 is turned on/off in sequence or modulated at a discrete individual frequency or pattern in time relative to the other NIR LEDs 610 then each signal upon the NIR Sensor 620 can be associated uniquely to a source NIR LED 610. Further, through the use of a temporally patterned NIR illumination the correlation between transmitted and received NIR signals can be enhanced by reducing the impact of stray IR light on the system(s). In this manner using appropriate and suitable image processing the so-called "glint" locations (reflect NIR signals) can be spatially defined allowing the distances and positions of the glints to be established relative to one another. Based upon known spatial and physical relationships between the NIR LEDs 610 and a model of the eye/cornea then the orientation of the asymmetric eyeball relative to the NR2I-HMD can be established and accordingly the user's line of sight determined.

Optionally, using a given eye/corneal reference radius with the user's line of sight established by projecting a specific image to the user then a distance to the eye, referred to as relief, can be calculated based upon the assumed eye geometry. Optionally, an initial radius may be assumed, and the computed distance employed to re-estimate eye curvature/shape from reflected NIR signals and then iteratively close the loop using this new estimate of eye shape to establish a new relief measurement and iterate until convergence is achieved. Alternatively, a reduced number of NIR LEDs may be employed if they are employed in a manner to provide structured light, i.e. light with a predetermined spatial patter. For example, a NIR LED 610 may generate two or more discrete optical beams designed to propagate within or past the Freeform Prism 400 whilst those within may be designed to impinge the user's eye directly and after a single reflection or multiple reflections.

The optional eye tracking sensor is also in communication with the NR2I processing electronics and determines where in the visual field of view (FOV) the individual is looking. In one embodiment, this sensor operates by following the position of the user's pupil. Such eye tracking devices are common in prior art "heads-up-displays" (HUDs) utilized by military pilots. An embodiment of pupil-tracking using a horizontally-oriented wedge-shaped freeform prism-lens is shown in FIG. 3. In this embodiment the display is augmented with NIR LED 210 and NIR Sensor 220 with their light paths passing through freeform surface S3 and located proximal to the MicroDisplay 140.

NIR light is emitted, bounced off the user's eye, and returns to the IR sensor, whereupon the received image of the eye is digitized, and the pupil's motion tracked using digital motion-tracking algorithms. Although an embodiment contemplated may include two tracking sensors, because both eyes typically track together, one tracking device may be used. In another embodiment, the eye tracking sensor uses a combination of mirrors and prisms such that the optical path for the eye tracking sensor towards the eyes is implemented with additional design flexibility. Eye tracking is used to determine the region of interest (ROI) within the FOV and either select and/or adjust and/or augment the content being presented to the user. In instances where the NR2I display is employed to address visual degradation in the user's optical vision then the eye tracking can ensure, for example, that damaged areas of the user's retina are avoided for displaying salient content within the image, the modified image, overlay content etc. or a combination thereof. The NR2I system may be configured to support off-axis eccentric viewing with X-Y field-of-view (FoV) offsets that are applied to the detected direction-of-gaze, since in these cases the user's best viewing area diverges from the normal axis. The eye-tracking information would typically be averaged, filtered, etc. through software to minimize the sensitivity to random eye movements, blinks, etc., and to optimize the system for various usage models. For example, reading English requires specific eye tracking performance in the left to right direction that is different from that in the right to left direction, and different again from that in the vertical direction. Hysteresis thresholds, dead-bands, filter time-constants and gains in the eye-tracking system may be adjusted independently for different directions based on which user, the task being performed, as well as other parameters such as ambient and environmental conditions, or objects or scenes (a correlated set of detected objects defines a detected scene) which may indicate a specific mode of operation is desired as a user preference. A user-profile may comprise a plurality of these settings, and the user-profile automatically selected based on biometric user-identification derived from the eye-tracking system for example using corneal or retinal scanning.

Figure 42:
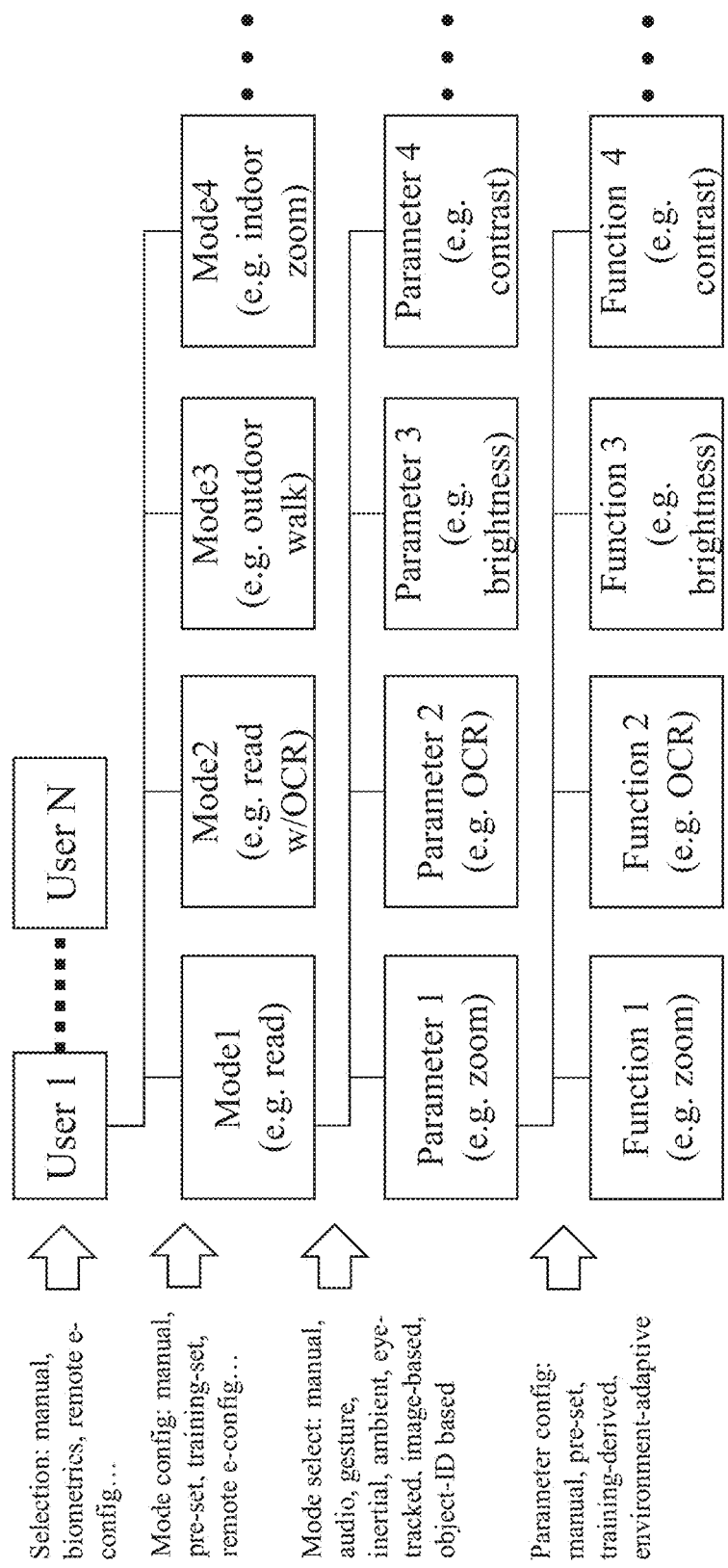
FIG. 42 depicts a schematic for an exemplary process according to an embodiment of the invention for supporting multiple users, where each user has multiple modes of using the NR2I display system.

Now referring to FIG. 42 there is depicted schematically a process for supporting multiple users each having multiple modes of using a NR2I display system according to an embodiment of the invention. Each mode having associated a set of parameters specific to that mode, and used to configure various functions of the NR2I display system. Either within the device itself, or accessible over a remote communications interface are stored the user IDs, modes and parameter settings. The selection of a particular user may be but not limited to a manual configuration (e.g. select user from a list), biometric training and selection (e.g., iris or corneal scan, fingerprint, etc.), or a remote configuration command.

Each user profile consists of both mode definitions and the parameter settings for device functions for that mode, as well as the trigger conditions for automatic mode selection. Operating modes may be manually configured, pre-set modes defined at initial device programming or configuration, derived from training or a training process, or remotely configured. The object of mode-configuration is to create operating modes which are most beneficial to the particular user for whom the mode and its associated parameter settings are created. Modes may be manually or automatically selected based on physical input such as a button-press, audio, gesture, inertial or vibration-feedback, ambient light conditions, eye-tracking data, image-content, depth-map information, or object recognition.

In any particular mode, the parameters for operating the devices sub-functions are defined and stored. Parameters may also be defined to be dynamic and responsive to image content or environment. The various parameter settings for each sub-function may be learned as a result of a training process in which optimal parameter settings for the particular user are learned. Operating modes are not mutually exclusive, for example indoor versus outdoor modes may be trained to automatically switch based on detected ambient light conditions, adjusting camera exposure, display brightness and contrast, while the device is simultaneously in a "read" mode wherein text within the captured image is identified, sent for optical character recognition, and re-rendered in fonts, colours, patterns etc. that have been pre-determined to have maximal readability for that user. Mode-selection criteria allow for inter-mode effects, for instance when in "read" mode, the OCR function may invoke text-to-speech synthesis when "outside" to improve user comprehension.

Typically user-specific modes and parameter settings are defined during initial device setup, user/device training and device configuration. Reference images may be used in this process to determine optimal settings for device parameters.

Accordingly, a gaze-tracking implementation in an NR2I system employing a wedge-prism was depicted in FIG. 6. In such systems the micro-display, the NIR emitter and the NIR sensor were collocated proximal the same face, and all light paths follow similar trajectories through the prism, with two internal reflections occurring within the prism. In contrast, within FIGS. 7 to 11 and 40 there are provided alternate configurations not disclosed nor taught within the prior art in respect to the configuration of a freeform prism lens, a micro-display, one or more NIR Sources and one or more NIR Sensors. For example, within a configuration according to an embodiment of the invention the NIR Sensor is located on the face opposite the user's eye (Surface S2), and light reflected from the user's eye performs no internal reflections within the prism before capture by the sensor. The eye may be illuminated using IR emitters at various locations as shown in FIGS. 7 through 11 both directly bypassing the freeform prism or through the freeform prism. Potential issues, advantages, disadvantages and particular features are described supra in respect of each of these Figures.

By placing in embodiments of the invention a NIR array sensor on the forward-face of the wedge freeform prism the sensor obtains an unobstructed view looking directly at the user's eye from the forward direction. The forward-face is designed based not on IR eye-tracking performance, but on user image quality, so the light-field received by eye-tracking sensor may be distorted. Factors such as distance from sensor to face, f-number, optical power of a single-pass through the prism (at IR wavelengths) and any potential additional optical element for eye-tracking (including but not limited to a pinhole stop or micro-lens) that may be interposed between sensor and face is adjusted such that NIR sensor images the user's eye in-focus at eye-relief of approximately 20 mm, and depth-of-field that includes the user's eye when the NR2I-HMD is in-use.

This optical pipeline may distort the image of the eye received by the NIR sensor and accordingly a compensation-function may be used to adjust the received x-y coordinates so that rectilinearity (image homo-morphism) is achieved between the observed eye and the captured and compensated image. This compensation for NIR sensor-to-eye-aberrations may be applied before any other processing is applied in order to determine gaze location. Further distortion and aberration may be introduced by prescription lenses or sunglasses disposed between the display optics and the user's eye. The presence of such lenses may be detected by the eye-tracking system by detecting the additional reflections off the lens' surfaces. When such lenses are detected, an additional IR-image compensation function may be applied so that proper registration and rectilinearity are achieved.

As discussed supra one or more structured light sources may be used in lieu of the broad illumination of the user's eye. In the structured-light methodology NIR light of a known source-pattern is projected towards the user's eye, and the a-priori knowledge of the geometry (and potentially timing) of the light source(s) allows processing of light reflected from the user's eye (typically the cornea) to establish the orientation of the user's eye. This structure may be both spatial and temporal. The structure may be varied in time, and a correlation function used to reduce the impact of noise and stray light. When multiple structured light sources are present, they may be illuminated in alternation and a variety of patterns. For example, using 4 NIR emitting points, e.g. 4 NIR-LEDs or 4 optical waveguides coupled to NIR sources, then these may be turned on in different combinations e.g. ABCD, ABC. ABD, BCD, the "one-missing" patterns, and other combinations. Dropping a LED that overlaps with a spurious reflection may be employed. If the position of the reflection of that LED's light is needed for gaze-estimation, it's position can be inferred from the known geometry and the position of the reflection of the other LED's light, e.g. triangle, square, trapezoid etc. Alternatively, or additionally, temporal modulation may be employed to provide a modulated output such that even if the LED signal overlays a spurious reflection the modulated output signal can be identified by correlating the received IR data with the known modulation pattern.

Within an embodiment of the invention a NIR LED or other light source may be placed at each of the four corners of a rectangle or square or three in a triangle etc. The eye's orientation may be calculated by correlating the deformation of the received image to expected deformations of the reflected structured light. In this manner the user's pupil position may be tracked. Further, the glint from corneal reflections may be used to determine gaze. The NIR LEDs may directly or indirectly illuminate the user's eye.

The centre of the pupil may be tracked by edge-detecting its boundary with the iris. The received IR image may be manipulated before edge-detection, e.g. using Canny edge detection CED such as described below in respect of FIG. 37. Multiple pupil edge-points may be used to improve accuracy and reduce noise in finding the pupil-centre. The surface of the cornea is most spherical near the centre, with decreasing radius near the edges, so preferential use of corneal reflections nearer the centre should be preferred. See for example FIG. 36—three of four LEDs lit, top-right is off, process flow of pupil-track is shown.

The visual axis (twixt fovea and nodal point of eye) and optical axis (twixt nodal point and object) are often misaligned even in the well-sighted, and for advanced macular degeneration (AMD) may be far off-axis at a different preferred retinal location (PRL).

If a bioptic hinge for the NR2I-HMD, which allows the HMD to be pivoted from the configuration in FIGS. 2A to 2C to that depicted in FIG. 2D to 2F, is aligned with user eye rotation then bioptic tilt compensation may not be required for eye/HMD reference frames. If the hinge is not perfectly aligned with the user's eye rotation axis, compensation for bioptic tilt may be performed to accommodate eye-NR2I geometry change as rotation occurs. Compensation between Nr2I reference frame and world-reference frame is made by knowing the bioptic angle. Bioptic angle may be measured and compensated relative to users' head-frame, or to world-frame, or both. These measurements may be made using angle-encoders or other direct measurement of bioptic angle, or the bioptic angle may be inferred from inertial sensors, accelerometers, and/or external magnetic-field detection internal to the NR2I display being rotated.

For structured light, measure distance from Nr2I to eye by inferring Z distance from x-y separation of reflection (glint) of structured light. Dots further apart mean eye is further away. Do this to learn eye-display geometry before the rest of processing, e.g. pupil size and direction. Filter out outliers, e.g. discard reflection from interposed prescription lenses, they are closer than some threshold eye-relief distance, and therefore must be spurious. May require compensation for eye-size and radius of curvature as well.

FIG. 12 depicts an exemplary transmission characteristic for a coating applied to a freeform lens assembly according to an embodiment of the invention for an exemplary NR2I-HMD employing multiple sources of NIR directly and indirectly coupled to the user's eye together with an imaging sensor for determining the orientation of the user's eye relative to the freeform lens. Accordingly, the coating provides transmission of visible light and reflection of NIR signals such that the coating may be applied to surface S2 420 of a Freeform Prism 400 within a transmissive NR2I system. Optionally, the simulated coating may provide high visible reflectivity and low NIR reflectivity such that the Region A 460 in FIG. 5 is coated with this thereby reflecting the emitted signals from the MicroDisplay 440 from surface S1 410 to surface S2 420 but allowing NIR signals from a NIR LED 610 to pass through towards the user's eye.

Figure 13A:
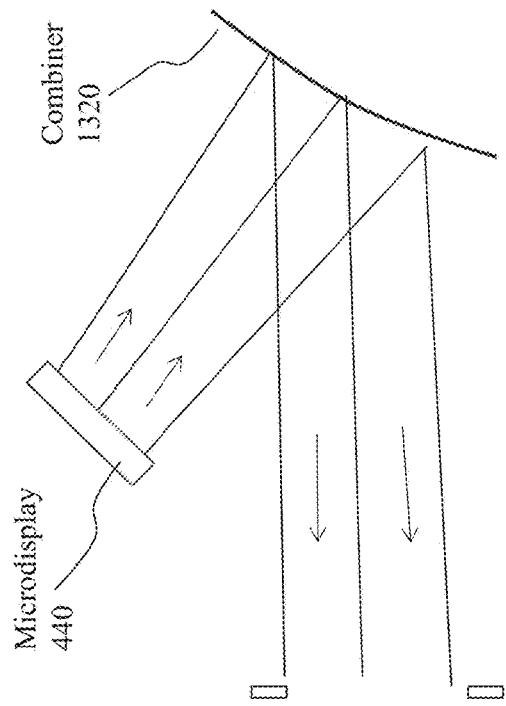
FIGS. 13A to 13D depict exemplary optical configurations for combining a micro-display with a user's field-of-view (FOV) according to embodiments of the invention.
Figure 13B:
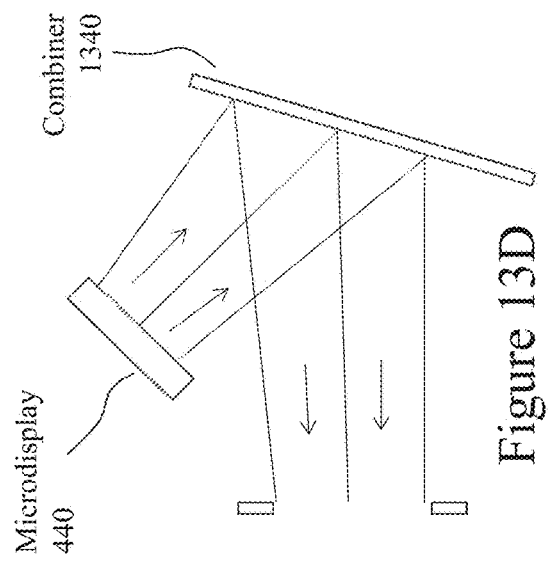
Figure 13C:
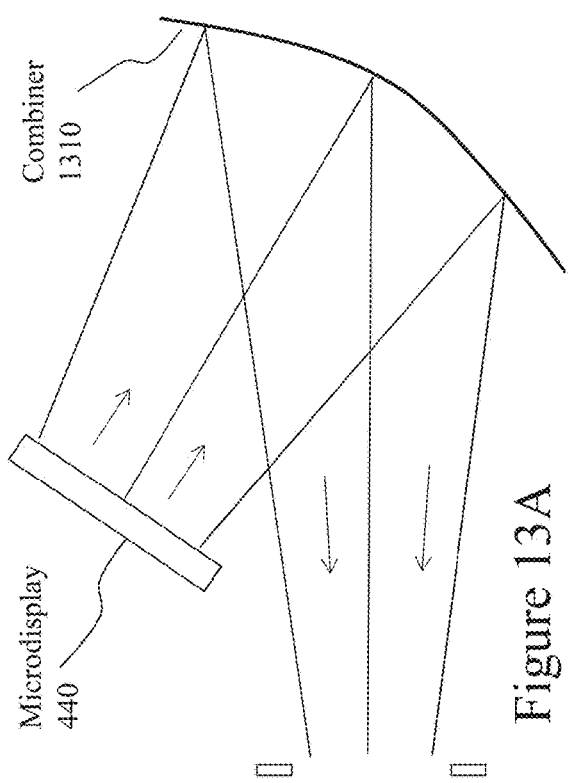
Figure 13D:
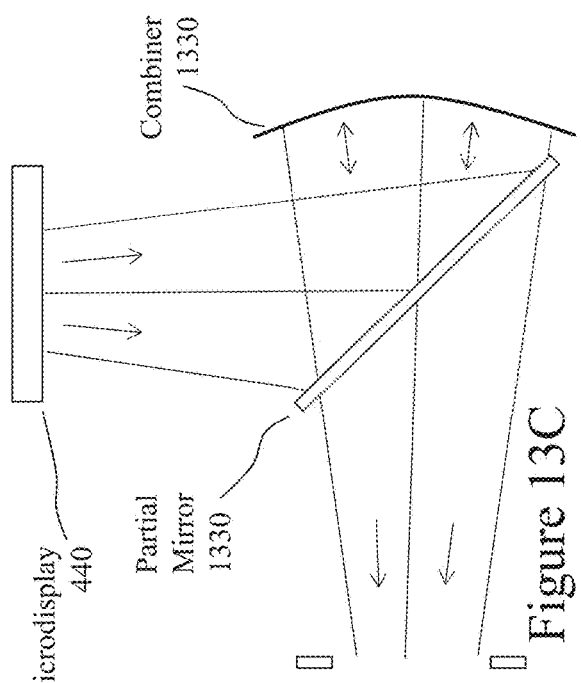

It would be evident to one skilled in the art that alternative optical trains (pipelines) may be employed as alternatives to a horizontal wedge shaped Freeform Prism 440 according to the requirements of the NR2I-HMD system. For example, as employed by the inventors a vertical wedge shaped freeform prism may be employed which is some respects is similar to the horizontal wedge shaped freeform prism although the lateral and vertical fields of view will generally tend to be less "landscape" and more square or "portrait" in geometry. Alternatively, as depicted in FIG. 13A a "concave" geometry first combiner 1310 may be employed with off-axis placement of the MicroDisplay 440 as an exemplary optical configuration for combining a micro-display with a user's field-of-view (FOV) according to an embodiment of the invention. Optionally, the concave mirror may be replaced. Alternatively, as depicted in FIG. 13B a "convex" geometry second combiner 1320 is employed whilst in FIG. 13C the image is projected onto a partial mirror, reflected forward and then reflected back by a third combiner 1330 towards the user's eye off a curved surface disposed in front, or below, with or without a partially-reflective surface interposed. Alternatively, in FIG. 13D a fourth combiner 1340 is employed surface is employed to reflect the image from the MicroDisplay 440. Whilst the surfaces depicted within FIGS. 13A to 13D are concave, convex and planar it would be evident that the actual geometry may be defined by a freeform surface to achieve the desired performance for the NR2I-HMD. Optionally, embodiments of the invention may employ Fresnel or multi-reflective surfaces and/or light guides to achieve the desired functionality.

In augmented-reality implementations, a controllable shutter may be employed to render the forward-view selectively opaque or partially opaque. This may be for the entire forward FOV or portions thereof. The whole forward-view may be controlled as a unit, or separately addressable portions of the forward-view may be opacity-controlled, for instance to allow a virtual overlay display at high contrast on top of the naturally-received image. This selective-opacity may be modulated at a high rate, for instance rates on the order of the refresh rate of the display, and in coordination with this refresh interval, in order to allow best perception of both the real-world and the overlaid virtual image.

Figure 14:
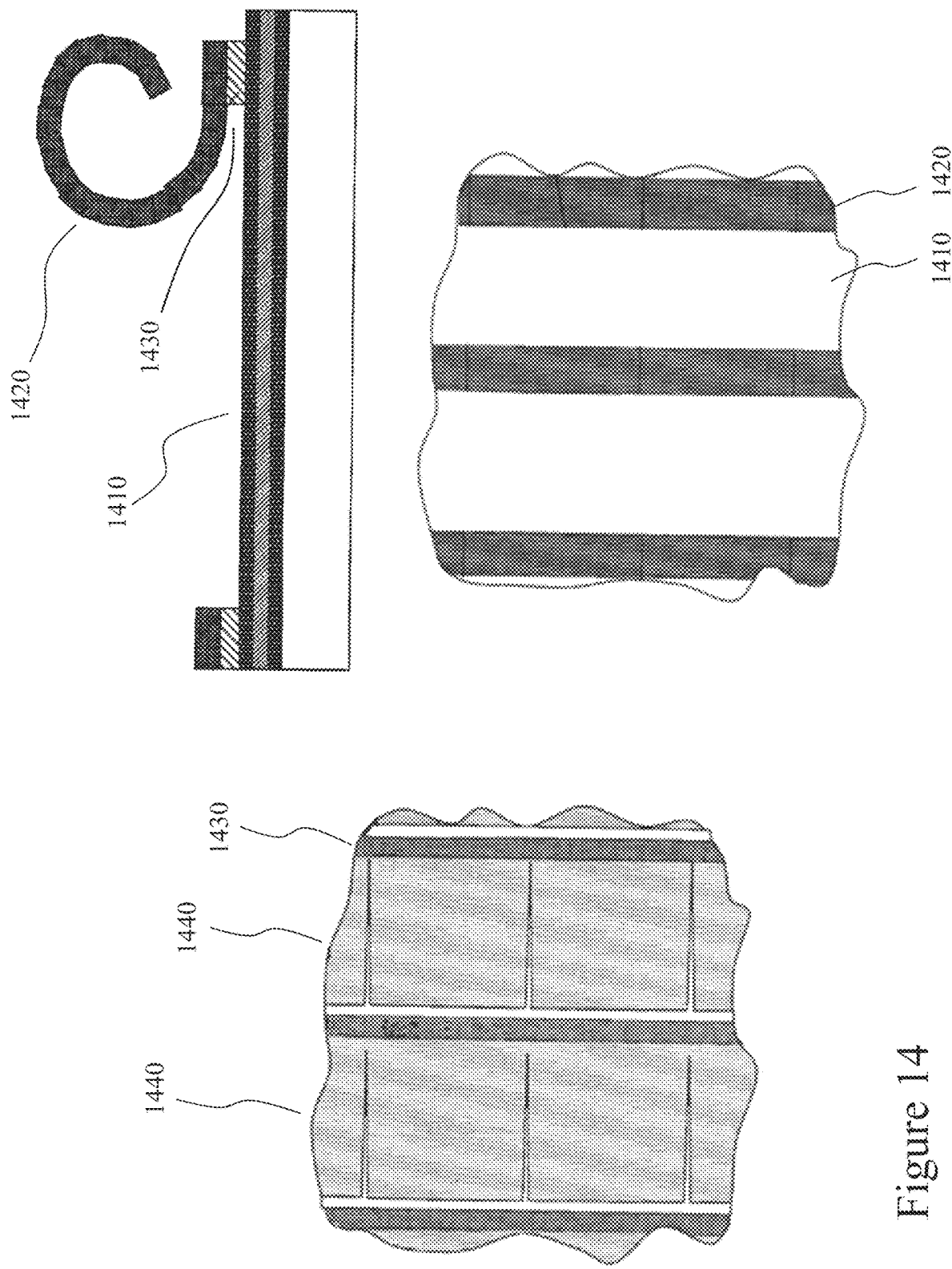
FIG. 14 depicts an exemplary micro-shutter design according to the prior art for use within an exemplary NR2I-HMD according to an embodiment of the invention for selectively blocking/unblocking the FOV image with respect to that projected by the display within the NR2I-HMD system.

Referring to FIG. 14 there is depicted an exemplary micro-shutter design according to the prior art (see Lamontagne et al. in U.S. Pat. No. 7,684,105) for use within an exemplary NR2I-HMD according to an embodiment of the invention for selectively blocking/unblocking the FOV image with respect to that projected by the display within the NR2I-HMD system. As depicted a series of thin films are deposited upon the surface of a display, lens, sensor, or carrier acting as the substrate. These being an underlying stack 1410 comprising an insulator, a diffusion barrier and/or adhesion promoter layer against the substrate with a transparent conducting layer atop and capped with an insulator layer. A release-sacrificial-anchoring layer 1430 and a reflective, resilient and stressed layer 1420. The stressed layer 1420 may comprise a plurality of sublayers in order to achieve the desired stress profile.

The diffusion barrier, adhesion promoter and insulator layer may be, for example, be a combination of Ti and TiNx. The transparent conducting layer may, for example, be ITO, SnO, ZnO, a thin Ag layer or a semi-transparent stack of Ti and Au. This layer should be reliable, cheap and preferably transparent throughout the visible spectrum and may be transmissive or reflective in the NIR according to the design of the NR2I-HMD. This is followed by the deposition of another insulator layer, for example SiO2. This layer should limit leakage current within the structure and may alternatively be a polymer or a dielectric like silicon dioxide, silicon nitride, carbon nitride, silicon carbide, titanium oxide, aluminium oxide and others. The release-sacrificial-anchor layer 1430 may, for example Si or W, and should give a very strong contact or anchoring point for the microblinds. It also should be readily partially removed during the fabrication process to release the microblinds and allow them to curl as a result of their inherent stress.

Finally, the deposition of reflective, resilient and stressed layer 1420, which has controlled optical properties and forms the microblinds, is carried out. The stress in reflective, resilient and stressed layer 1420 is important and can result from different coefficients of thermal expansion in different sublayers or from intrinsic stress induced by the deposition method itself. For example, using sputter deposition, a stress gradient can be introduced in the films by varying the deposition conditions. All these layers can be deposited using common technologies (dip coating, evaporation, CVD, PECVD or sputtering) for the flat glass manufacturing industry. The right choice of materials and deposition methods depends on the targeted performances.

Stressed layer 5 should be thin to allow a small radius of curvature and thus high transparency of the windows when all blinds are opened. Ideally, the materials should be resilient (not brittle or too ductile) to resist the fatigue of multiple actuations and have the long lifetime expected of a window pane. The total thickness of these layers will be provided such that they remain cost effective, provide reliable mechanical structure and are thick enough to reflect or absorb light. The total thickness of all the reflective, resilient and stressed layer 1420 is typically between 100 nm (0.1 μm) and 10 μm. The thickness of the reflective, resilient and stressed layer 1420 is typically about 25% of the total thickness of the layers. Patterning of the microblinds can be accomplished by any method known to those skilled in the art, including standard optical lithography. However, owing to the large dimensions involved, some methods are particularly advantageous: micro-templating using very large rollers with a mold, laser patterning or a combination of those methods or others.

Within FIG. 14 the microblinds are depicted respectively in the closed and open states. Once released, the released portions of the microblinds curl by themselves due to the inherent stress, which defines the open state. To close them, a voltage is applied between the conductor within the underlying stack 1410 and reflective, resilient and stressed layer 1420. This voltage must be high enough that the electrostatic attraction exerted is larger than the inherent stress that induces the curling of the reflective, resilient and stressed layer 1420. The value of the actuation voltage is proportional to the stress and the thicknesses of the release layer and insulator.

Figure 15:
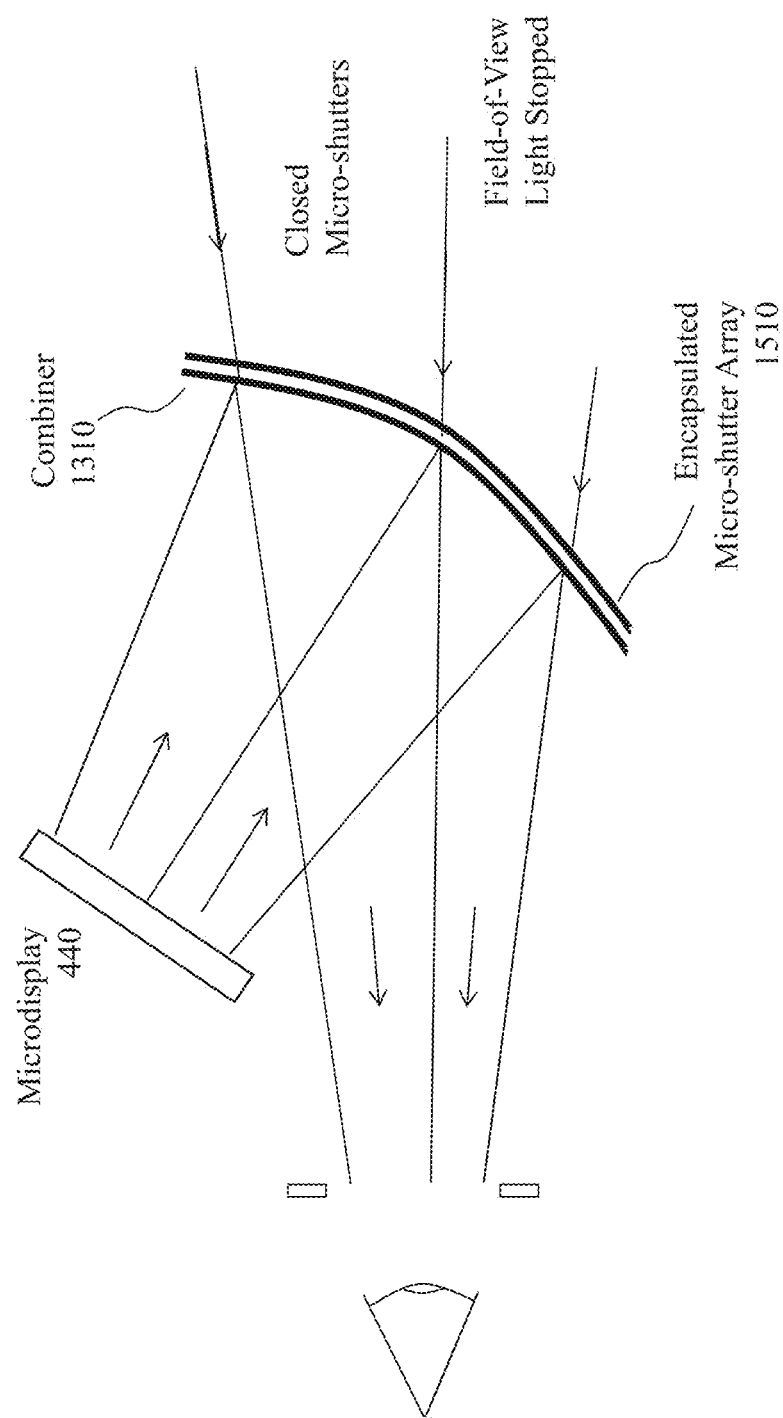
FIG. 15 depicts an exemplary optical configuration combining a micro-display with a user's field-of-view (FOV) according to an embodiment of the invention through a "concave" combiner such as depicted in FIG. 13A together with micro-shutters such as depicted in FIG. 14.

Now referring to FIG. 15 there is depicted an exemplary optical configuration combining a micro-display with a user's field-of-view (FOV) according to an embodiment of the invention through a "concave" combiner 1310 such as depicted in FIG. 13A together with an Encapsulated Micro-Shutter Array 1510 such as depicted in FIG. 14. It would be evident to one of skill in the art that the MicroDisplay 440 may be controlled to display content over a portion or all of its display area and that the content may be displayed in multiple selected locations simultaneously. Accordingly, a full, partial or multiple image segments can be projected and coupled to the user's vision via the Combiner 1310. The Encapsulated Micro-Shutter Array 1510 disposed behind the Combiner 1310 between the external FOV and the Combiner 1310 can be selectively driven to be transparent over some portions of the user's FOV, opaque over others (micro-shutter maintained closed) or partially opaque (micro-shutter duty cycled between closed and open with variations in duty cycle changing the degree of opacity.

Accordingly, the Encapsulated Micro-Shutter Array 1510 can be controlled to provide a range of functionalities to the NR2I-HMD. For example, FOV content may be selectively blocked where image content is to be displayed. Optionally, the Encapsulated Micro-Shutter Array 1510 may be used to reduce overall external FOV brightness.

Optionally, a NR2I system may also employ an Encapsulated Micro-Shutter Array 1510 in combination with a camera forming part of the NR2I-HMD system. Accordingly, the selective shutters may also be used to improve the dynamic range of the imaging sensor by placing a shutter over each sensor pixel or a group of sensor pixels. Accordingly, the shutters can be used to implement pixel-level exposure-control of the image sensor or by adjusting the exposure time for each pixel or pixel-group independently, the dynamic range of the imaging sensor can be enhanced. Any pixel (or pixel group) that is approaching saturation can have its exposure-time reduced, while leaving the exposure-time for other pixels untouched. A pixel (or group) that is receiving little light and has a low signal-to-noise ratio may have its exposure lengthened. Post-processing of the pixel value and exposure-time allows a single image to be comprised that has dynamic range and signal-to-noise performance greater than that of the sensor alone. For example, a sensor pixel whose exposure time was half the time of another might have its pixel-reading doubled in order to calibrate it with respect to the other pixel.

Within embodiments of the invention the exposure-control could be implemented via an adaptive process. According to an embodiment of the invention the process flow may comprise:

Step 1: Capture first image;
Step 2: Compute image luminance/intensity histogram;
Step 3: Assign to each pixel or pixel-region its bin-number from the histogram (number of histogram bins may be much smaller than all possible pixel intensities multiple pixel-intensities may be mapped to the same bin as well);
Step 4: Establish an exposure-control map in dependence upon the histogram-map, in which pixels or regions that map to the brighter histogram buckets are given reduced exposure, and pixels or regions mapped to lower-intensity bins are given increased exposure;
Step 5: Compute the received image pixel intensity as a function of both received sensor pixel intensity and the pixel's exposure control; and
Step 6: Repeat this process periodically.

Options to adjust the process may include, but are not limited to:

Continuously compute the histograms but only periodically update all the mappings;
Perform exposure control changes only periodically, at a rate less than the frame rate;
Only perform exposure-control computations on detection of a metric over a threshold, for example a luminance changes faster than some specific rate, in part or all of the received image;
Limit the variation in shutter-control to certain prescribed values in order to simplify image-processing. For example, provide four levels of exposure-control wherein each level (time) is one half or double of another. Pixel-math then simplifies to shift-left or shift-right of binary sensor values (doublings and halvings of the reported sensor pixel intensity) in generated the received image pixel intensities.
Use different global parameters in the exposure control in dependence upon the pixel colour. Per-colour histograms (as opposed to grey-scale). Different exposures and mapping math per-colour. Sensor-pixels of greater sensitivity given reduced exposure compared to pixels of higher sensitivity Where histogram bins are adaptive, the bin-parameters ("catchment areas") are defined in dependence upon the number of pixels that fall into the bins for the received image. For example, suppose we want to have four levels of exposure control. Move histogram bin boundaries until roughly one-fourth of all pixels fall into each bin, lowest-intensity bin gets highest exposure, highest intensity-bin gets lowest exposure, in between gets in-between exposure.

The Camera 120 within the NR2I-HMD may be a charge coupled device (CCD) camera with high depth-of-field optics such as found in a range of high volume consumer electronic devices such as smartphones, a high quality CCD sensor such as employed in digital SLRs allowing high resolution magnification and/or image stabilisation etc. In other embodiments, the Camera 120 may be a Complementary Metal Oxide Semiconductor (CMOS) image sensor with appropriate optics. Optionally, the Camera 1120 may be external to the NR2I display and associated with an item of apparel of the user or an item of equipment employed by the user or independent of the user, their clothing and equipment. In other various embodiments, the image capture device is any imaging device with an analog or digital signal output that can be sent to the NR2I display for processing or to the user's PED for processing and display on the NR2I display. The image-capture device may implement High Dynamic Range processing using exposure-control through the use of micro-shutters that control light incident on the sensors.

It would be evident that the micro-shutter technology discussed and depicted supra would be compatible with direct integration to a CMOS CCD design imaging sensor.

Figure 16:
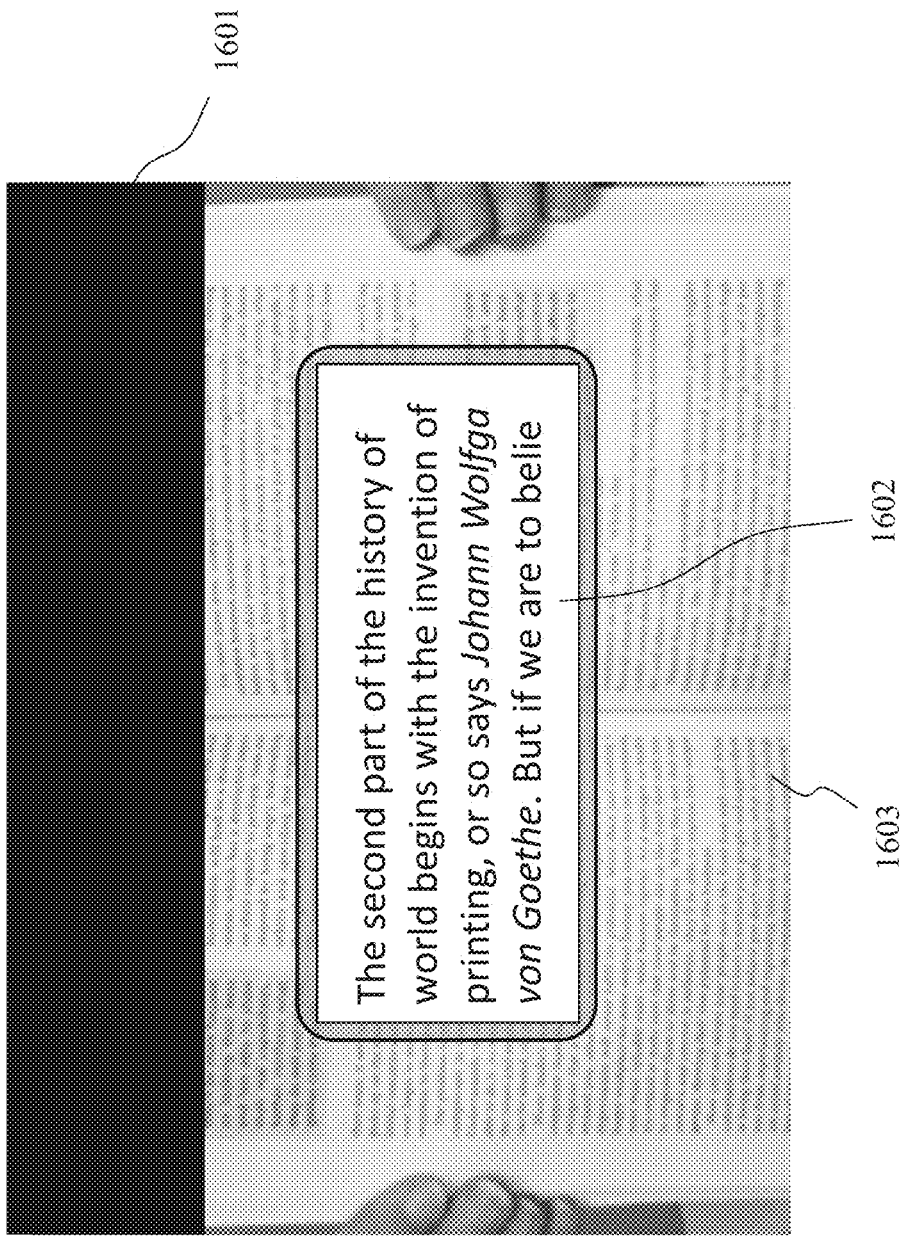
FIG. 16 depicts a simulated view presented to a NR2I-HMD system user according to an embodiment of the invention whereby the user's view through the optical train with respect to their external FOV may be set fully transparent, fully opaque or partially transparent.

Referring to FIG. 16 depicts a simulated view presented to a NR2I-HMD system user according to an embodiment of the invention whereby the user's view through the optical train with respect to their external FOV may be set fully transparent 1603, fully opaque 1601 or partially transparent 1602. Such an optical train being that depicted in FIG. 15, though in other embodiments the selectively-opaque layer may be applied in other areas, for instance proximate Surface S2 of free-form prism-based optical trains interposed between S2 and the freeform corrector 460 of FIG. 6, or on the opposite, forward-facing surface of the freeform corrector 460.

Figure 17:
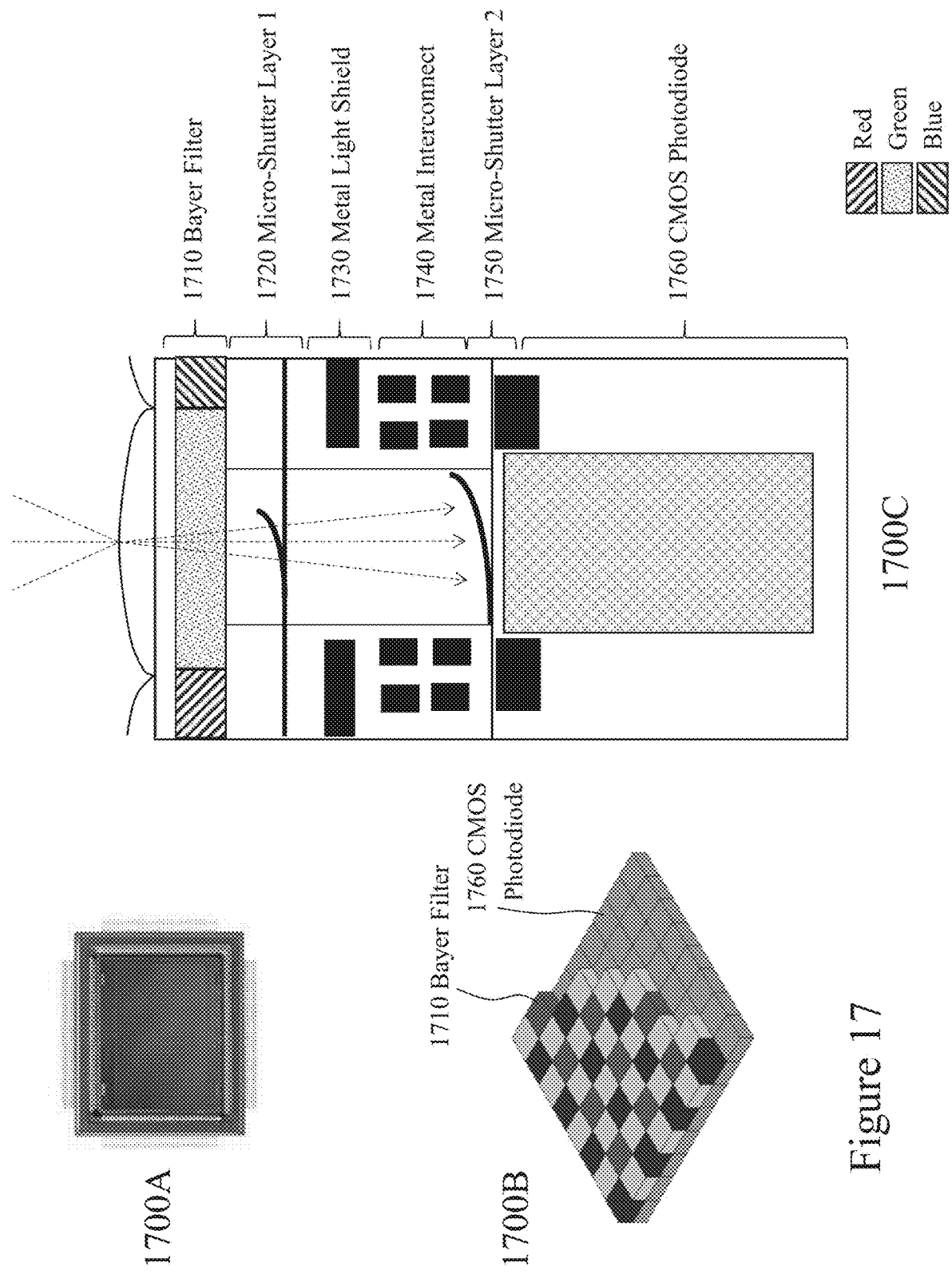
FIG. 17 depicts a pixel of a selectively shuttered CMOS image sensor for use within a NR2I-HMD according to an embodiment of the invention.

Now referring to FIG. 17 there is a pixel of a selectively shuttered CMOS sensor in first image 1700A for use within a NR2I-HMD according to an embodiment of the invention. Second image 1700B depicts the Bayer filter mosaic 1710 of colour filters atop the colorless CMOS photodiodes 1760 in their arrayed form. Accordingly, a depicted in third image 1700C the CMOS photodiode 1760 is topped by a stack comprising, from bottom to top:
- Micro-shutter layer 2 1750;
- Metal interconnect 1740;
- Metal light shield 1730;
- Micro-shutter layer 1 1720; and
- Bayer filter 1710, As depicted the microshutter layer 2 1750 is formed prior to deposition and etching of the metal interconnect 1740 and Metal light shield 1730 so that the microshutter is able to roll up/deploy within a recess in the stacked dielectric/metal structure. Similarly, Micro-shutter layer 1 has the microshutters within openings in an upper dielectric layer atop which the Bayer filters 1710 are disposed. Such microshutters may also be employed within the NIR Sensor(s) 620.

Optionally, one or more additional aspects of the microshutters may be exploited including but not limited to:
- A single micro-shutter imposed in light-path for each pixel, e.g. micro-shutter layer 1 or micro-shutter layer 2;
- Dual micro-shutters may be imposed in light-path for each pixel;
- Shutter(s) may be synchronized with sensor image acquisition (e.g. at frame-rate);
- Individual micro-shutter control allows variable 0-100% exposure, per-pixel, per-frame, if necessary;
- Metallization interconnect for micro-shutter array control overlaps with existing CMOS sensor wiring and/or light shield, causing no decrease in photo-diode light reception;
- On-chip shutter configuration storage;
- Multiple bits to define exposure control;
- Low-light, longer exposure, potentially with reduced frame rate, coupled with exposure control achieves higher sensor dynamic range; and
- Vacuum encapsulation of shutter layer for flutter-free fast switching.

Figure 18:
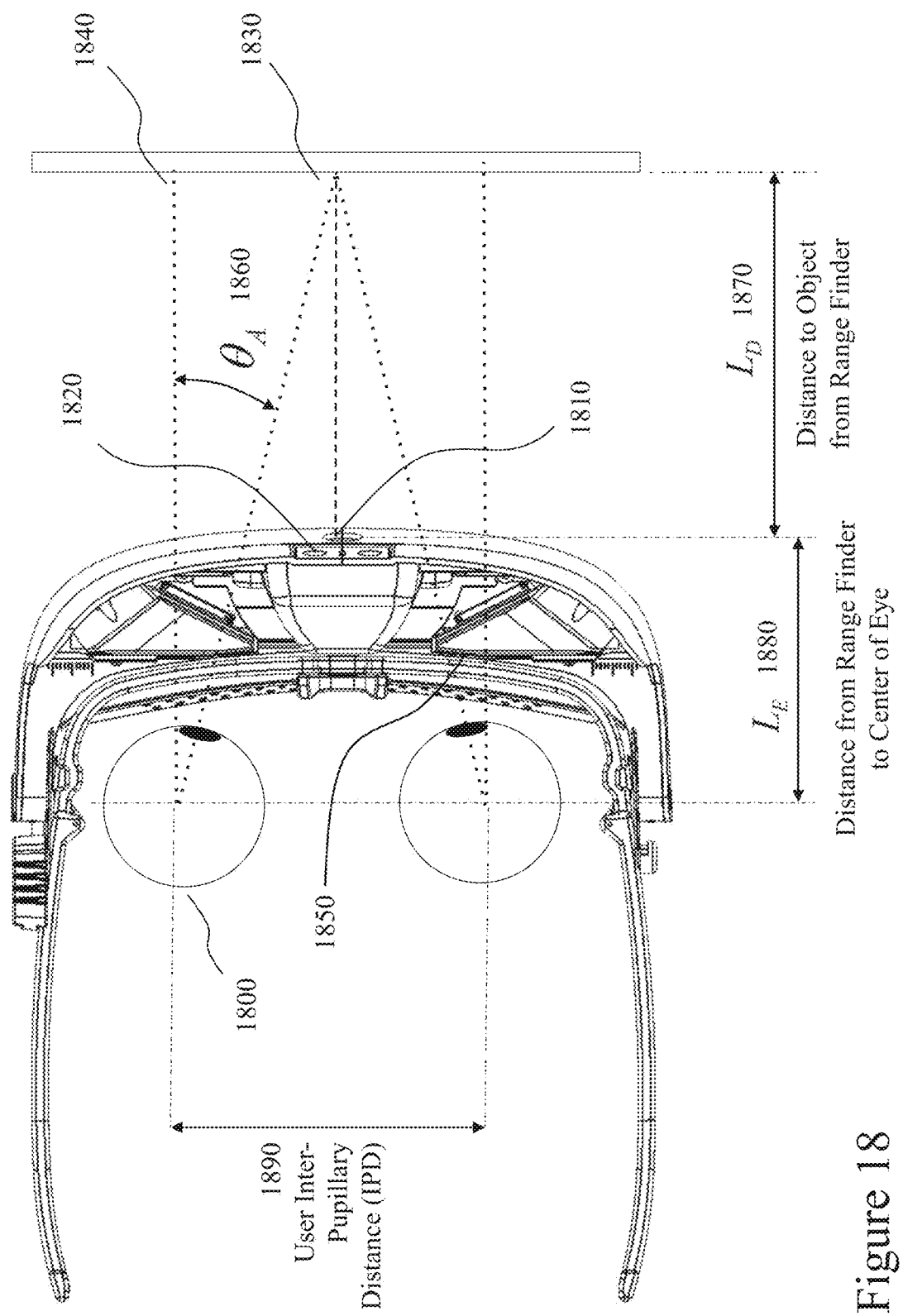
FIG. 18 depicts the angular and distance relationships for a range finder within a NR2I-HMD system according to an embodiment of the invention.

Now referring to FIG. 18 there is depicted the scenario when a healthy, un-aided human eye 1800 focusses at a centered, far distant object 1840 (i.e. "at infinity" as commonly referred to). The eyeball shape is adjusted to bring focus to infinity, and the angle $\theta_A$ 1860 of the two eyes are controlled such that the pupils are facing directly ahead, i.e. the eyes are in a parallel orientation, and $\theta_A$=0. As the object of interest moves closer towards the user, two effects occur. One is that the eyeball shape is adjusted to bring the focal-depth in from infinity to match the distance to the object (accommodation), and the second is that the eyeballs are rotated towards each other so that each eyeball is aligned with the object of interest, and the eyes are no longer in a parallel position (vergence). In the limit, the user is cross-eyed staring at the bridge of their nose, and the inter-pupil distance (IPD) 1890 has reduced substantially as the eyes gaze turned inwards. Typical NR2I systems provide the image at a fixed focal depth of infinity, and the IPD of the images are fixed, which may result in diplopia (double-vision) or eye-strain when viewing close objects, as the eyes are not operating in a "natural" manner for close objects. Improved usability can be achieved if a mechanical or electronic IPD adjustment is made dynamic, and according to the distance to the object being viewed, as identified through a combination of eye-tracking and FoV image depth-mapping, achieved using either a range finding system or through indirect means such as depth-mapping from defocus-information, or other means, such as stereoscopy or LIDAR.

For NR2I systems employing a built-in camera, the auto-focus features of the image capture system may be used to direct the digital image processing system to laterally translate the images inwards towards the nose as the objected focused-upon decreases in depth from infinity. This dynamic IPD display can more accurately mimic real-world conditions and behaviours, reducing eyestrain and improving usability.

The function that relates distance to the object to the number of pixels by which to digitally translate the displayed images may be simple or complex. Again referring to FIG. 18, a simple example might be to take distance information from either a depth-map derived from image data or the rangefinder 1820, and for distances $L_D$ 1870 less than some threshold T to laterally translate the left and right image pixels towards each other by a function of $L_D$ 1870 and T, f(T,D), until a second, minimum, distance threshold is reached.

A more complex example might be to consider the geometry of the situation as follows in order to take advantage of the small angle approximations $\sin(x) \approx x$, and $\cos(x) \approx 1$ for small x. Suppose the width of the display areas 1850 is covered by a micro-display of P pixels in width, achieving a horizontal field-of-view angle of V degrees. The small-angle approximation here is that there are P/V pixels per degree of viewing angle. Assuming a centered object 1830, the tangent of the eye-angle $\theta_A$ 1860 to the object 1830 is half the user IPD 1890 divided by the distance from the centre of the user's eye to the rangefinder, $L_E$ 1880 plus the distance from the rangefinder to the object $L_D$ 1870 as given by Equation (1). In this manner, the number of pixels to shift may be given by either Equation (2) or (3) for example where f(*) might be the identity function or alternatively may be one of a number of functions that threshold, limit, scale, etc.

$$\theta_A = \arctan\left(\frac{IPD}{(2 \times (L_D + L_E))}\right) \quad (1)$$

$$\text{Pixels\_to\_Shift} = A \times \frac{P}{V} \quad (2)$$

$$\text{Pixels\_to\_Shift} = f\left(A \times \frac{P}{V}\right) \quad (3)$$

More complex examples still might consider off-centered objects, employ both eye tracking data and the range to the object of gaze and then shift the images asymmetrically, and/or independently for left and right eyes, and/or in the vertical orientation and/or rotational translations as well, the display dynamically responding to the user's gaze. In such cases although the user's eyes 1800 are focused on an off-center object the central rangefinder 1820 will measure the depth to the centered object 1830. Gaze-tracking implemented with any of a variety of mechanisms (for example using additional imaging devices directed towards the user's eyeball or eyeballs) may be employed to allow an improved image to be displayed. First, by employing both a depth-map derived from the image-data, in combination with the location within the image to which the user's gaze is directed through gaze-tracking, as well as the current focal depth, then the system may derive the difference in depth between where the camera is currently focused versus where the user is gazing, and thus issue a focusing command to bring the gazed-at object into improved focus. Secondly, as the object is now no longer centered in the horizontal field of view, each eye's rotation assumes a different angle, $\theta_L$ for the left eye and $\theta_R$ for the right eye.

Analogous to the symmetric case above, a lateral image-shift may now be computed independently for each of the left and right displays such that each eye perceives the image of the object being gazed-at in the correct location for an object at that depth and offset from centre being viewed in the absence of the near-to-eye HMD system, and thus making the image appear more natural to the user. Further, the combination of a central range finder 1820 and image-based depth-mapping also allows periodic or continuous calibration of the image-derived depth map at the central field of view as measured by the rangefinder.

In a manner similar to that described for the horizontal direction, both eye tracking data and the range to the object of gaze may be used to then shift the left and right display images symmetrically or asymmetrically, and/or independently for left and right eyes, and/or in the vertical orientation as well, the displays dynamically responding to the location of the user's gaze. A means for performing such shifting of image content before presentation to the user is described in detail within U.S. Provisional Patent Application 62/150,911 entitled "Methods and Devices for Optical Aberration Correction," the contents of which are incorporated herein by reference.

These image translations, either simple or complex, may be employed alone or in combination in order to minimize a visual degradation of the user, such as double-vision for example. An assistant or the user themselves may employ an input device or devices to select and adjust the translations, rotations, corrections etc. applied to improve the user's visual acuity for that particular user. These settings may be modified over time through a training program to train one or more aspects of the user's visual system, including, for example, their eye, muscles, nerves, neural processing, towards a specific objective (e.g. "lazy eye" muscle strengthening. In some instances, it may be beneficial to occlude an image continuously, periodically, randomly, presented to one or other eye, or on only portions of a presented image to allow a weaker eye and/or further neural processing to strengthen itself in a training process.

Within other embodiments of the invention such training may be invoked when the user is playing a game or performing another predetermined task, or it may be continuously applied. In embodiments of the invention, the portion of an image to one or other eye may be varied over time based upon one or more factors including, for example, current activity, degree of image processing applied, and image source. An optician or other eye-specialist, or the user themselves may define a training regimen that is then imposed upon the user by the NR2I display. The training regimen may be adaptive, based on feedback provided by the eye-tracking system.

Figure 19A:
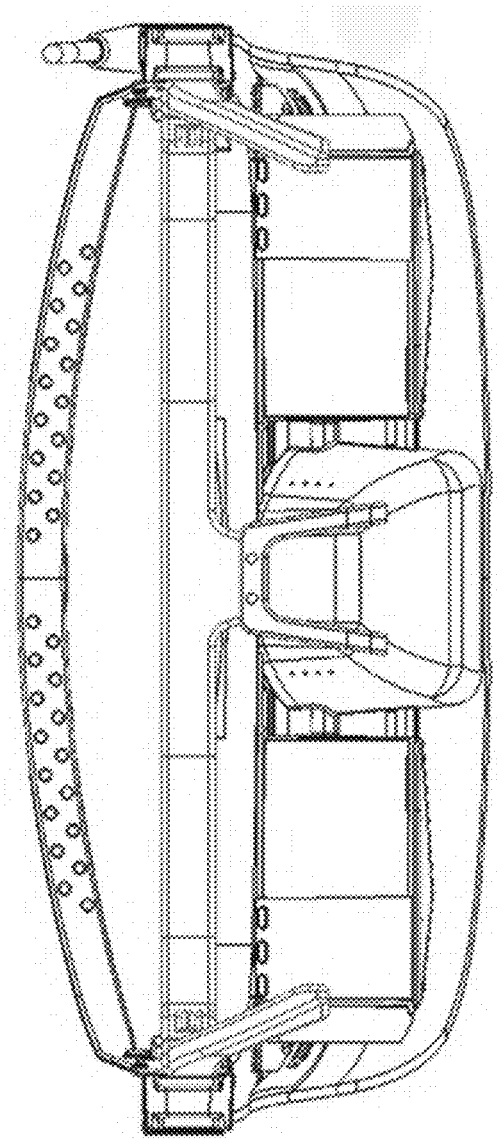
FIGS. 19A and 19B depict the inner facing portion of an immersive NR2I-HMD system according to an embodiment of the invention when the dual display portions are set to maximum and minimum inter-pupillary distance (IMD) respectively.
Figure 19B:
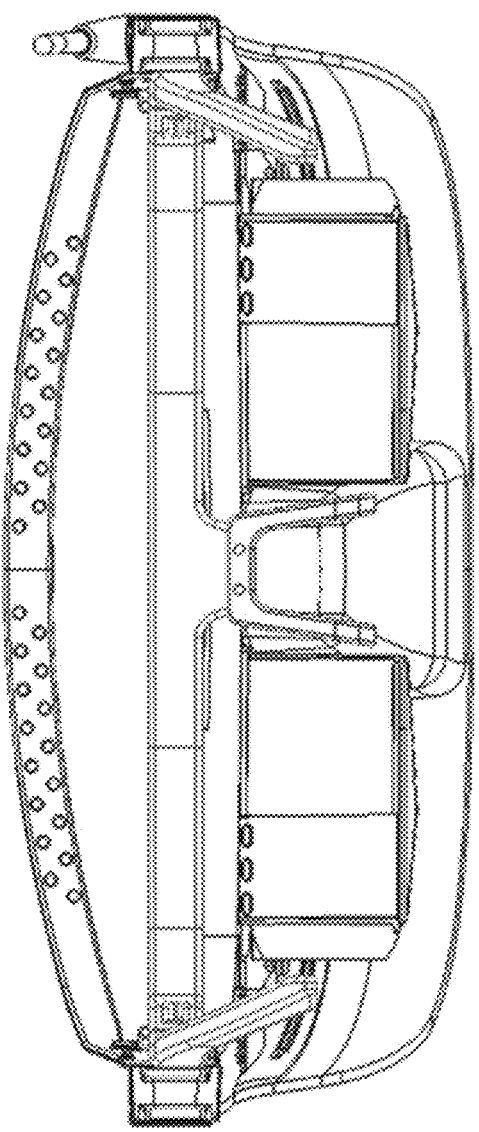

Now referring to FIGS. 19A and 19B respectively an NR2I display is presented from the user's perspective allowing the POD (the display assembly for each eye being collectively referred to as a POD) adjustment for display Inter-Pupil Distance (IPD) to be visualized, nominally defined as the lateral distance between the centres of the left and right viewing areas, and nominally set to match the distance between the user's pupils, although the user might choose alternate preferred locations, for instance locating the displays closer than their own IPD for consistent close-up use. Referring to FIG. 19A the PODs are depicted at their maximum IPD of approximately 70 mm (approximately 2.75 inches) where the mechanical IPD adjustment is made by sliding the PODs in and out upon their rail-shaped mounts, though any POD attachment scheme that allows lateral translation might be employed. In FIG. 19B the PODs are depicted at their minimum IPD of approximately 40 mm (approximately 1.6 inches). During initial fitting an initial or average IPD setting for the user is fixed, for example using a set-screw operating on the POD assemblies. After this fixed IPD has been set, the NR2I display electronics may further dynamically control the horizontal location of the images displayed to the user's eyes (and thus the effective display IPD) through simple digital translation of the images displayed on each of the two microdisplays. For example, to digitally increase the IPD after the PODs have been mechanically fixed the image displayed by the left POD would be digitally shifted left, and the image displayed by the right POD digitally shifted right. Iteration between digital and mechanical IPD adjustment may be employed to reduce fitting time, for example by starting from an initial factory default IPD, digitally adjusting until the user is satisfied with the setting, reading the digital IPD setting from the NR2I system, then mechanically adjusting the IPD to the digital setting as read, in order to maximize usable display area. The combination allows pixel-level IPD control. Additional micro-display pixels beyond the desired display resolution may be employed, e.g. "border" pixels which are similarly used to translate images for digital image-stabilization, or if no such information or pixels are available, suitable null data may be presented.

The depicted bioptic immersive NR2I system in FIGS. 19A and 19B is similar to that depicted in FIGS. 1A to 2F in isolation from a user in side elevation with the NR2I down. Within FIGS. 19A and 19B the NR2I display is depicted assembled together with a lens less frame at the maximum IPD and minimum IPDs respectively. These being established during initial configuration of the NR2I to the user via a rigid rail and clamping assembly such as described and depicted in respect of FIG. 3. Accordingly, the lens less frame rests upon the ears of the user and the bridge of their nose with weight relief provided through the optional headstrap depicted that fits across the wearer's forehead when the NR2I is worn.

Figure 19C:
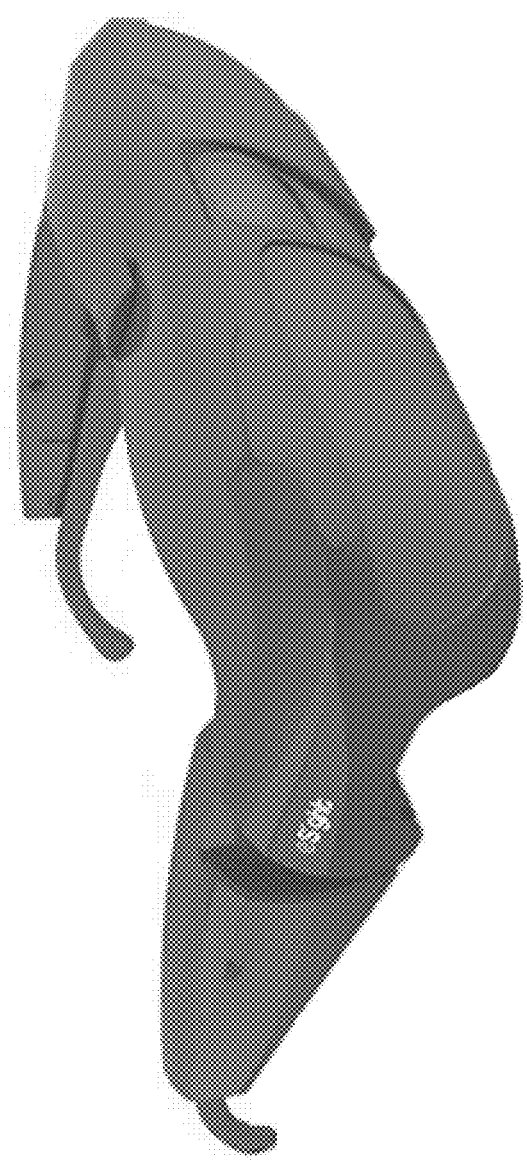
FIGS. 19C and 19D depict external perspective views of transmissive NR2I-HMD systems according to embodiments of the invention.
Figure 19D:
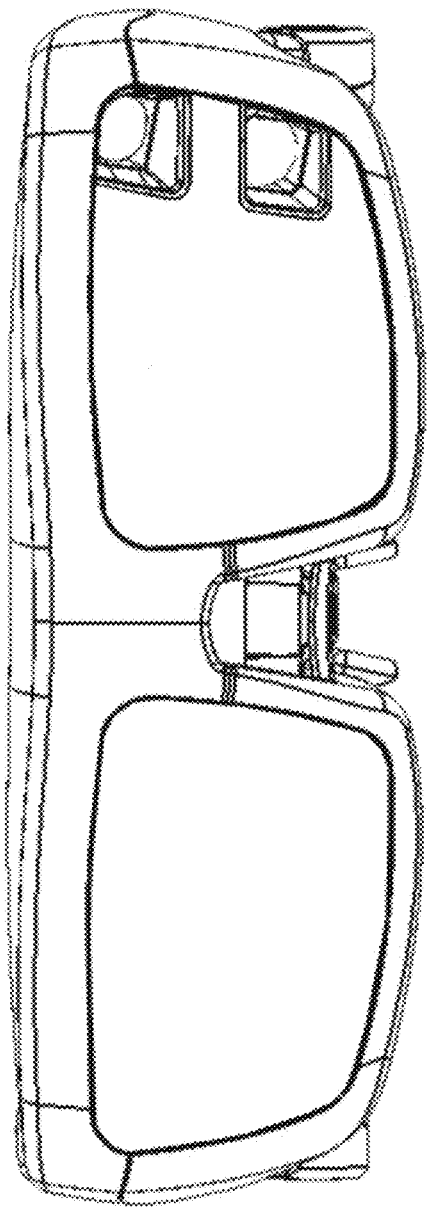

Alternatively, as depicted in FIGS. 19C and 19D the lens less frame and NR2I-HMD demountable may be configured with adjustable IPD as discussed in respect of FIG. 3 but within a transmissive NR2I context. Accordingly, the exterior frame of the demountable portion includes optical windows allowing the user to view through the freeform prism to their exterior world. Optionally, the lens less frame may be replaced with a frame with prescription lenses or alternative lenses may be provided with or without a prescription such as those that are tinted, polarizing or photochromic, for example. In either instance, the exterior of the demountable portion around the optical windows comprises one or more baffles such as upper baffles, lower baffles, and side baffles which block extraneous light.

Now referring to FIGS. 20A and 20B there are depicted the bioptic immersive NR2I system similar to that depicted in FIGS. 19A and 19B where the NR2I display is depicted assembled together with a lens less frame at the maximum IPD and minimum IPDs respectively. However, in this instance the freeform prism assembly now incorporates gaze/eye tracking optics. Considering initially this is depicted in FIG. 20A as four NIR LEDs 2010 disposed at the four corners of the freeform prism which is a lateral freeform prism in the left-hand assembly coupled to a Lateral Mounted Display Assembly with LED & Sensor Circuit Assembly 2020 whereas in the right-hand assembly it is a Vertical Mounted Display Assembly with LED & Sensor Circuit Assembly 2030. In each instance the NIR Sensor has been omitted for clarity but one or more NIR Sensors may be disposed as discussed supra. In another embodiment alternate locations for the IR image-sensors, for instance mounted at the bottom of PODs, directly facing the user's eyes are used, depicted as alternate IR sensor location 2200.

In contrast within FIG. 20B on the left-hand side there is a Lateral Mounted Display Assembly with LED & Sensor Circuit Assembly 2040 which is coupled to a Lateral Freeform Prism with Waveguides 2050. Hence, on the right-hand side there is Vertical Mounted Display Assembly with LED & Sensor Circuit Assembly 2060 which is coupled to a Vertical Freeform Prism with Waveguides 2070. In each instance of vertical or lateral freeform prisms there are four Waveguide Exits 2080 which direct the NIR optical signals to the eye in the same physical locations as if they were populated with the NIR LEDs in FIG. 20A. However, in FIG. 20B the NIR LEDs are within their associated display/control circuit assemblies. In FIG. 20B the NIR sensor is similarly omitted for clarity but it would be evident to one of skill in the art that the NIR Sensor may be similarly co-located with the NIR Sources and their driver circuits etc. such that optical signals from the user's eye are coupled back to the NIR Sensor via other optical waveguides formed into or formed in association with the freeform prism. Alternatively, the waveguides may be employed solely for the NIR Sources and the NIR Sensor(s) are disposed as discussed supra with respect to the freeform prism(s).

Accordingly, the designs depicted within FIGS. 20A and 20B allow the NIR Sources, NIR LEDs, to either directly illuminate the eye when mounted in the pods or be routed via waveguides. Optionally, with the optical waveguides a single LED can be coupled to multiple waveguides and hence support multiple emitters within the face forward portion of the pods unless individual control of the emitting points is required, e.g. for differentiating multiple NIR Sensor readings and associating to a specific NIR source. Optionally, the waveguides may be designed to provide off-axis illumination relative to the normal of the freeform prism at that point. Within the embodiments described and depicted in respect of FIGS. 20A and 20B the NIR LEDs are assembled within sub-assemblies that are rigidly attached to a frame of the NR2I-HMD which incorporate the freeform prism, the microdisplay, the NIR Sources, NIR Sensor, the mounting to the rail and associated local control and power circuits. Accordingly, the NIR Sources and NIR Sensor are co-referenced to the freeform prism and their spatial relationship does not vary.

However, in other embodiments of the invention the NIR LEDs and/or NIR Sensor may be physically referenced to the frame of the HMD independent of the placement of the freeform prism etc. Optionally, the NIR LEDs may be configured to generate what the inventors refer to as "structured" light which defines a geometrical pattern/structure such that whilst the geometry adjusts as the IPD is varied the eye-tracking can be compensated for the variation in NR2I geometry between NIR source and sensor through the data retrieved from the structured light.

Optionally, the NIR LEDs may be physically separate from the freeform prism assemblies but the locations of the NIR emission physically referenced with respect to the freeform prism through the use of optical fiber connections between the NIR Sources and freeform prism assembly.

Figure 20C:
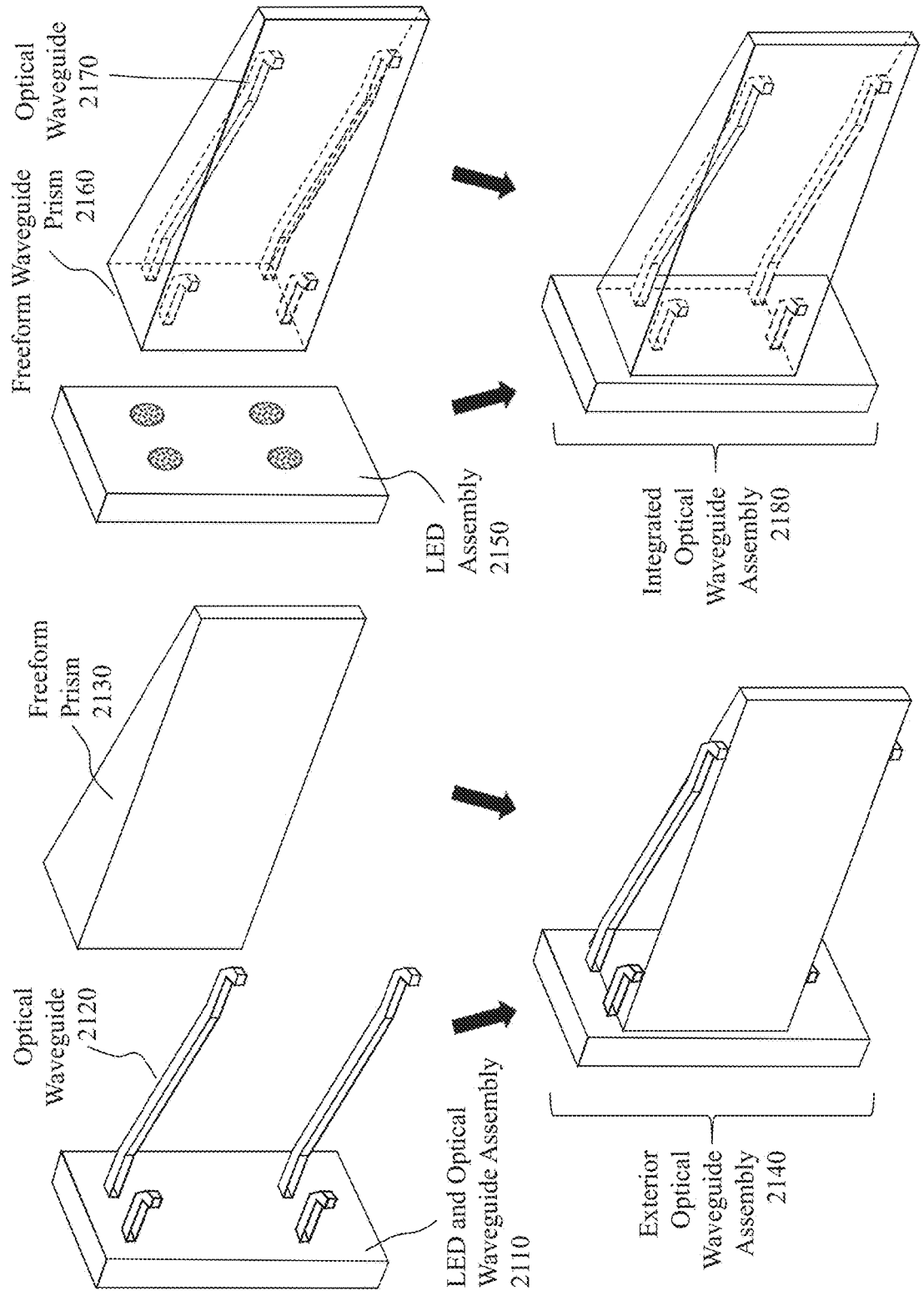
FIG. 20C is a schematic drawing showing comparison between a wedge-shaped prism with planar surfaces versus a wedge-shaped prism with freeform surfaces.
Figure 24:
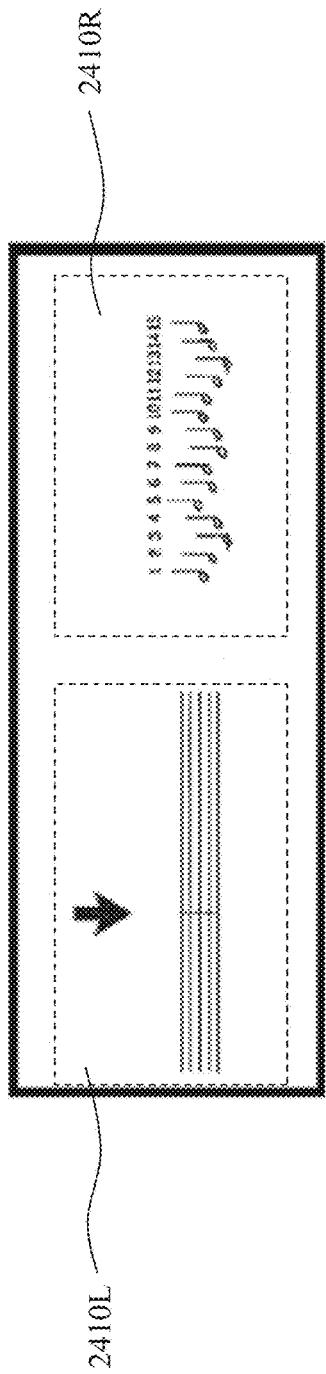
FIG. 24 depicts a configuration image presented to a user of a NR2I-HMD according to an embodiment of the invention wherein the test measures the relative posture of the user's eyes in the lateral plane.

Referring to FIG. 20C there are depicted simplified sketches of a wedge-shaped prism with planar surfaces as opposed to a wedge-shaped prism with freeform surfaces indicating options for combining the prism with optical waveguides. Accordingly, on the left-hand side is depicted an Exterior Optical Waveguide Assembly 2140 and on the right-hand side an Integrated Optical Waveguide Assembly 2180.

The Exterior Optical Waveguide Assembly 2140 is comprised of a LED and Optical Waveguide Assembly 2110 and the Freeform Prism 2130. As depicted the Optical Waveguides 2120 are external to the Freeform Prism 2130 such that the Freeform Prism 2130 can be formed independently and then assembled with the LED and Optical Waveguide Assembly 2110, Within an embodiment of the invention the LED and Optical Waveguide Assembly 2110 may be a molded plastic, molded polymer, molded glass, etc. with recesses in the rear surface to accept insertion of LED devices such as those within TO-Can packaging wherein the TO-Can packaging may include in addition to the hermetic housing of the NIR LED an optical lens or other optical elements.

The Integrated Optical Waveguide Assembly 2180 is comprised of a LED Assembly 2150 and a Freeform Waveguide Prism 2160. The Freeform Waveguide Prism 2160 being the same geometry as the Freeform Prism 2130 but has Optical Waveguides 2170 formed within. As depicted, these are within the body of the Freeform Waveguide Prism 2160 whilst within other embodiments of the invention they may be formed on the surface(s) of the freeform prism. The LED assembly incorporates the NIR LEDs and is assembled with the Freeform Waveguide Prism 2160 to form the Integrated Optical Waveguide Assembly 218.

It would be evident that within other embodiments of the invention these techniques may support integration of optical waveguides to couple received reflected signals from the user's eye to the NIR Sensor(s). It would be evident that other construction approaches and methodologies may be employed within departing from the scope of the invention.

Now referring to FIG. 21 there is depicted an exemplary code segment for performing separate distortion map corrections for digital pre-compensation of chromatic distortion in the red, green, and blue display portions without dynamic IPD correction. This methodology as described by the inventors in "Methods and Devices for Optical Aberration Correction" filed Apr. 22, 2015 with application No. U.S. 62/150,911 and its formalization and continuations including, but not limited to, U.S. Ser. No. 15/135,805 and U.S. Ser. No. 15/799,075. The exemplary code segment applies a static distortion map to image data such that the image displayed upon the micro-display once subjected to the chromatic distortions of the freeform prism is perceived correctly by the user. As the chromatic distortion is different for red, green, and blue then different maps are used such that whilst the three different colour signals may combine in the user's eye to provide the target colour at the target location the three display pixels are not necessarily associated with a single pixel of the display depending upon the distortions being corrected.

However, extending this as depicted in FIG. 22 there is presented an exemplary code segment for performing separate distortion map corrections for digital pre-compensation of chromatic distortion in the red, green, and blue display portions with dynamic IPD vergence correction. Accordingly, the pixel mapping is dynamically associated based upon the determined shift in the IPD which is established through the variable uXShift.

Accordingly, the two OpenGL code samples in FIGS. 21 and 22 relate to the use of independent red, green, and blue texture-maps for the correction of the chromatic aberration introduced by a freeform prism-lens according to an embodiment of the invention. The code snippet of FIG. 21B has been augmented relative to that of FIG. 21A by the inclusion of a lateral image-shift using the variable uXShift which can be independently programmed for left and right displays such that the effective display IPD can be varied a function of viewed-object distance, thus achieving a degree of bio-mimicry of the natural viewing environment. Within the embodiment described and depicted in respect of FIG. 18 or with an integrated camera range-finding mechanism digital processing may be employed to provide distance information to the image-processing subsystem. The induced lateral shift may be a simple function, e.g. uXShift=x/d where x is a configurable scaling parameter and d is the distance established by the NR2I display/system such as via the rangefinder. It should be evident to those skilled in the art that alternate means of range-finding, alternate functions for mapping from range to uXShift, etc. are within the scope of the invention. It would be evident to one of skill in the art that an image processing pipeline may be employed to apply the vertical translations and/or offsets, rotational translations and/or offsets, and other mappings/corrections required by the user.

It would be further evident that the NR2I may be adjusted to reflect a particular vision issue for a user in respect of this where the natural retinal motion may be different for the user in one or both eyes. With respect to the code snippet of FIG. 21B the process first checks that the lateral shift is still within the valid image area, and if not, replaces the image data with (0,0,0,1) i.e. an opaque black display. An improvement upon this black-filling approach within scope of the current invention is to provide image-sources of greater pixel-width than that of the display so that full display-width is maintained as the user's eyes rotate and the display-images are shifted or panned across the source image.

A NR2I-HMD according to an embodiment of the invention may employ a configuration initialization process at the initial use of the device by a user, wherein the variable uXShift may be determined and employed during this initial set-up process along with others before the process proceeds to a training mode and establishing triggers for changing any mode or modes of the NR2I-HMD. Accordingly, an exemplary process flow may comprise:

Step 1: Obtain user identity;
Step 2: Retrieve configuration settings for NR2I-HMD from memory, either HMD memory or a PED associated with the NR2I-HMD;
Step 3: Configure dynamic image processing settings from retrieved configuration settings;
Step 4: Configure algorithms for image processing, IPD, distortion maps etc.;
Step 5: Configure any different modes of the NR2I;
Step 6: Establish trigger conditions for configuration changes;
Step 6: Establish trigger conditions for mode changes;
Step 7: If the training mode has not previously been executed then configure training otherwise proceed to use;
Step 8: Monitor mode triggers for changes and upon detecting a mode trigger meeting one of the predetermined criteria trigger the appropriate mode change.

Trigger conditions for a mode change may include, but not be limited to, ambient conditions (e.g. night versus day, artificial light versus), image content being acquired (e.g. reading, watching television, walking, driving etc.), gaze-tracking, inertial sensor within the NR2I-HMD, manual input, etc.

Now referring to FIGS. 24 to 30 there are depicted exemplary images provided to a user during a training/configuration sequence for a NR2I. Accordingly, considering FIG. 24 there is depicted a test screen, potentially one of several, relating to measuring the relative posture of the eyes in the lateral plane. The left eye sees a musical staff with a prominent arrow, left image 2410L, whilst the right eye sees numbered notes, right image 2410R. With both eyes open, the subject will fuse the notes onto the staff. The arrow should point to the musical note #8. The user is then prompted with a series of questions and varying images. Accordingly, the user is initially asked "Do you see a series of musical notes? If yes, ask how many." The answer is 15. The subject is then told that a musical staff with a white arrow will appear. Simultaneously, the NR2I turns the LEFT eye switch ON and asks which note the arrow is pointing to. The subject's initial response is the answer you are looking for. The arrow pointing to #8 is ideal, or orthophoric, pointing between 3.5 and 12.5 is the accepted norm. 1 to 8 indicates esophoria, 8 to 15 indicates exophoria. Each number represents one prism diopter of power. The user may be visually prompted or audibly prompted or both depending upon the configuration of the NR2I, e.g. with speakers or through an associated PED/FED whilst their responses may be determined via audible, motion, text entry etc. again according to the configuration of the NR2I and any associated PED/FED.

Figure 25:
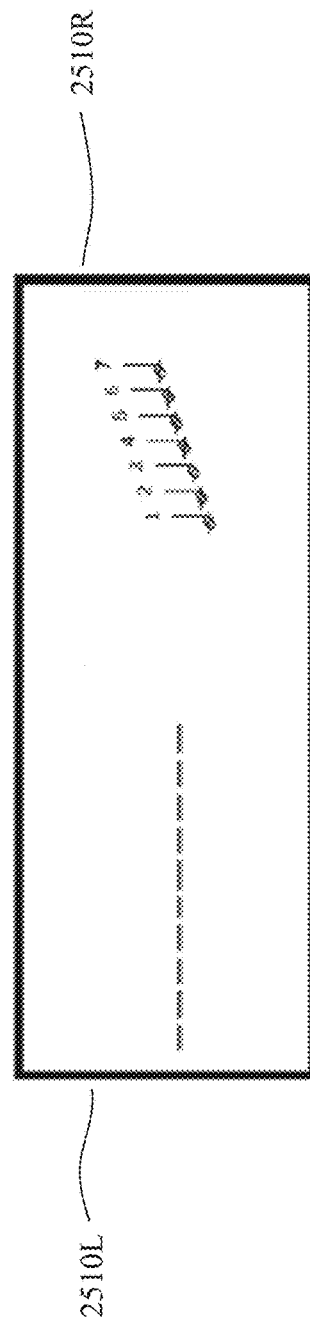
FIG. 25 depicts a configuration image presented to a user of a NR2I-HMD according to an embodiment of the invention wherein the test measures the relative posture of the user's eyes in the vertical plane.

Referring to FIG. 25 there is depicted a test screen, potentially one of several, relating to measuring the relative posture of the eyes in the vertical plane. Musical notes are seen with the right eye, right image 2510R, with a series of red dashes with the left eye, left image 2510L. The test records the number of the notes through which the red line passes where for ideal vision the note should align precisely across from the red line #4. Accordingly, the process executes the sequence:

Step 1: Ask question 1 "Do you see a series of musical notes? If yes, ask how many?";
Step 2: Receive user's initial response, which should be 7;
Step 3: Advise the subject a red broken line will appear and simultaneously turn the LEFT eye switch ON;
Step 4: Ask question 2 "The line crosses the round part of which note?";
Step 5: Receive subject's answer.

The subject's initial response is the answer you are looking for where the red broken line passing through note #4 is ideal or orthophoric. Anywhere from 2.5 to 5.5 is the accepted norm. If the subject complains of movement, ask where the line was first seen. Each number represents one half prism diopter of power, 1 to 4 indicates left hyperphoria, 4 to 7 indicates right hyperphoria.

Figure 26:
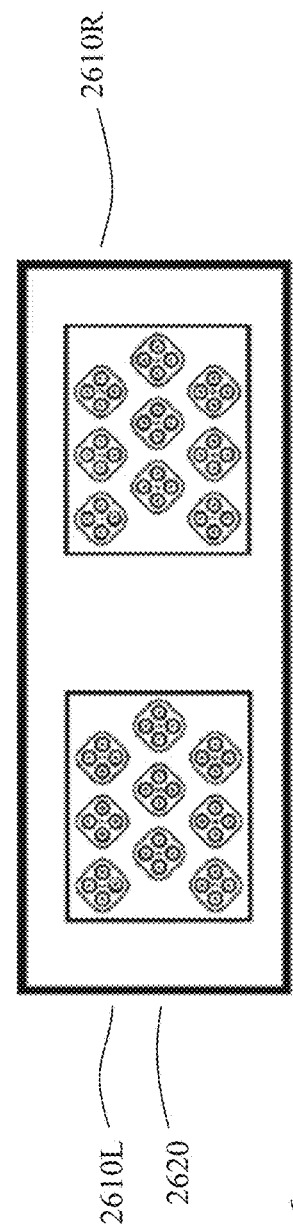
FIG. 26 depicts a configuration image presented to a user of a NR2I-HMD according to an embodiment of the invention wherein the test measures the user's binocularity.

Referring to FIG. 26 there is depicted a test screen, potentially one of several, relating to measuring binocularity. In order to perceive depth perception, both eyes are required to work together. Omit this test if there is little or no vision in one eye. The ability to judge relative distances without the aid of monocular clues is the goal of this stereotest. The difficulty in identifying the "floating" ring increases in each of the nine steps in this series. The left and right images 2610L and 2610R may comprise varying apparent depth of a ring 2620 within the set of 9 rings.

Accordingly, the process comprises an initial question "Study target #1. Does the bottom ring seem to be floating toward you?" If the answer is YES, then proceed with "In target #2, which ring is floating toward you? #3, #4?" This test requires a little extra time, so being patient is extremely important. On occasion, a subject with good acuity scores will fail to fuse the left and right eye patterns and experience an overlapping of images. Turn the dial back to a test where the subject can stabilize fusion, then proceed. Reading all the circles correctly through #9 is normal depth perception. Correctly answering the circles through #5 is acceptable depth perception. When the subject misses two consecutive circles, use the last correct answer as the score. Table 1 below defines the user's stereopsis in accordance with how far they progress through the test together with Stephen-Fry percentages which defines the amount of visual efficiency required to determine a particular angle of stereopsis (85% is considered average).

TABLE 1

Stereo Depth Key

| 1 | 2 | 3 | 4 | 5 | 6 | 7 | 8 | 9 | |
|---|---|---|---|---|---|---|---|---|---|
| B | L | B | T | T | L | R | L | R | Target |
| 400 | 200 | 100 | 70 | 50 | 40 | 30 | 25 | 20 | Stereopsis Angle (seconds of arc) |
| 15 | 30 | 50 | 60 | 70 | 75 | 82 | 90 | 95 | Shephard-Fry Percentages |

Figure 27:
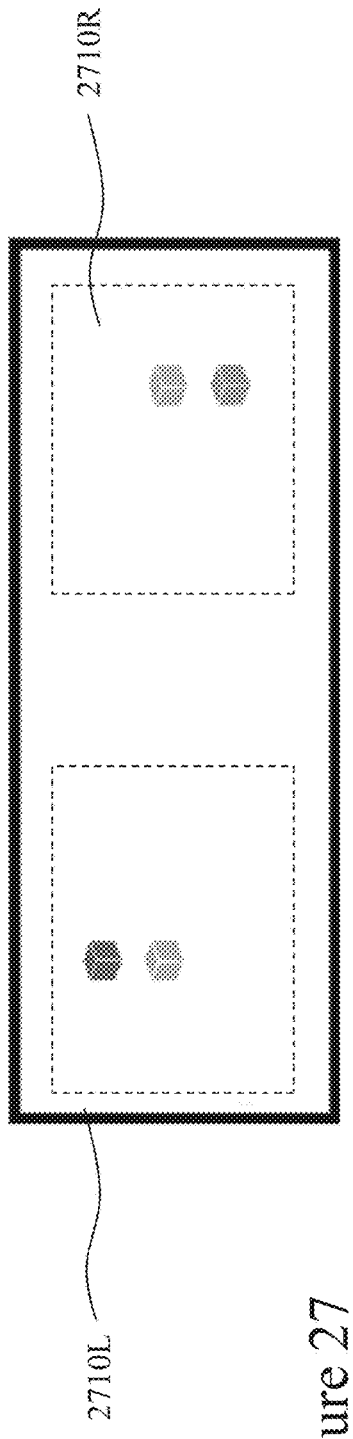
FIG. 27 depicts a configuration image presented to a user of a NR2I-HMD according to an embodiment of the invention wherein the test measures the FOV perception in lateral and vertical planes.

Referring to FIG. 27 there is depicted a test screen, potentially one of several, relating to measuring colour/spatial content. The user is asked "How many boxes do you see?" In the example depicted left eye is presented left image 2710L with a red box and a white box whilst the right eye is presented a white box and a blue box in right image 2710R. With respect to "scoring" then the left eye sees a red box and a white box, and the right eye sees a white box and a blue box. Together, both eyes should see THREE boxes. Red on top, white in the middle, and blue on the bottom. Any other combination is a "FAIL". This test can be extended to present different colours, different shapes, different spatial positions to test aspect of the user's vision.

Figure 28:
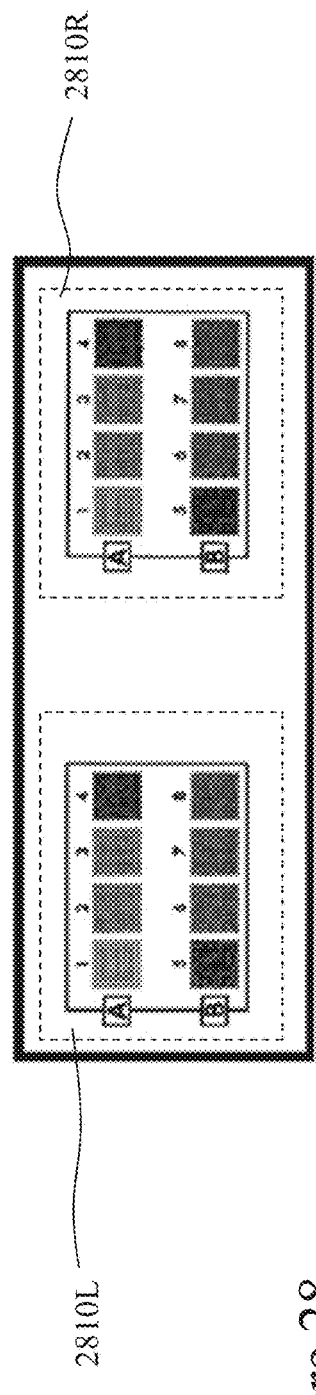
FIG. 28 depicts a configuration image presented to a user of a NR2I-HMD according to an embodiment of the invention wherein the test measures the user's colour perception.

Referring to FIG. 28 there is depicted a test screen, potentially one of several, relating to measuring/screening color perception. It will identify deficiencies, but it does not classify them. Eight Pseudo-Isochromatic Ishihara Plates are accurately and authentically reproduced for this test. This test is a set for a minimal visual acuity of 20/70. If a subject has 20/70 acuity or lower, the subject could fail the test because of low vision, not poor color perception. Accordingly, the user is asked "Which way is the "E" pointing in each block? Top, Bottom, Right or Left, starting with block #1."

A subject with normal color perception can identify the "E" in each of the eight blocks. Acceptable color perception is correctly identifying five of the eight "E" characters. Blocks 2 and 3 are the most difficult to identify, so it is recommended to test block 1 then 4, 5, 6, 7, 8 and then come back to 2 and 3. Any subject who fails one or more tests in blocks 1, 2, or 3 should be retested at a later date. When retested, many subjects will pass the second time. There are many normal reasons for this, such as medications, tiredness or anxiety. Retesting also makes referrals more valid. In respect of the correct sequence then Table 2 lists the orientations.

TABLE 2

Pseudo-Isochromatic Ishihara Plates

| A | 1 = R | 2 = L | 3 = B | 4 = T |
|---|-------|-------|-------|-------|
| B | 5 = B | 6 = L | 7 = T | 8 = R |

Figure 29:
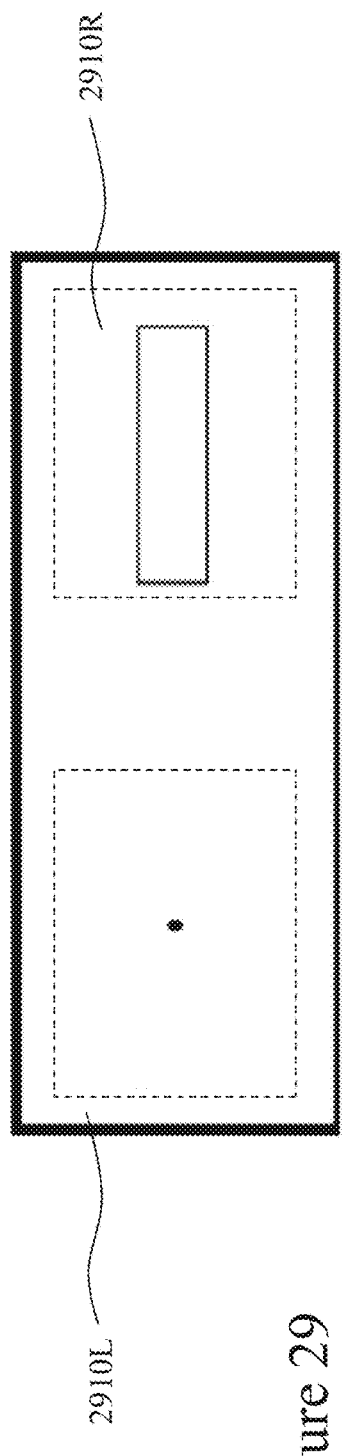
FIG. 29 depicts a configuration image presented to a user of a NR2I-HMD according to an embodiment of the invention wherein the test measures the user's temporal and spatial responsivity.

Referring to FIG. 29 there is depicted a test screen, potentially one of several, wherein the user's responsiveness is tested. The user is initially asked "Do you see a box?" If yes, then the subject is told that a red ball will be thrown at the box, simultaneously, the Left eye switch is turned on and the user asked, "Where did the ball land, IN or OUT of the box?" If the user answers IN the box it is a PASS, OUT of the box is a FAIL. The initial response without time to consider is taken.

Referring to FIG. 30 there are depicted test images 3000A to 3000C for determining astigmatism in the user. An image is presented to the user in one eye and then in the other eye. If the user does not have astigmatism, the lines will appear sharply focused and equally dark when viewed with each eye. The user has astigmatism if they indicate some sets of lines appear sharp and dark, while others are blurred and lighter. Optionally, multiple images may be employed with varying line widths, patterns, etc.

Referring to FIG. 31 there are depicted first to third images 3100A to 3100C relating to colour blindness. First image 3100A being an original image presented wherein according to the user's identification of numbers alternate patterns such a second image 3100B or third image 3100C are presented to the user. Second image 3100B represents shifting green numbering to blue and third image 3100C represents shifting red numbering to blue. Optionally, rather than just adjusting the numbers the backgrounds might be changed as well.

According to an embodiment of the invention the NR2I may present a sequence of images and seek responses from the user. For example, according to an exemplary process:
    Step 1: Analyze user vision to determine a set of discernable shades
    Step 2: If no colouration is discernable, jump to grey-scale processing
    Step 3: Say set of discernable shades is of size/cardinality N, then divide full-colour palette into N spectral regions;
    Step 4: Create a mapping from N spectral regions to the shade-set;
    Step 5: Save the discernible shade-set against the user identity, and spectral region-information for each user.

Accordingly, when the user is identified as the present wearer of the device then the NR2I may reconfigure processing for this user. As image data arrives, from any source such as camera, external, synthesized, etc. then bin the pixels of the image into spectral regions. Replace the image-content of pixels that map to each spectral region with the discernible shade associated with that spectral region in the user's profile.

Optionally a user may be allowed to store multiple such templates, select amongst them. Some templates might use all discernible shades, some might use only highest-perceived-contrast shades to ensure user-detection of presented shade-differences, etc.

Optionally, the discernible shade-set (or sets) is/are stored and static, specific to the user, but the colour-mapping of image-pixels to these shade-sets is dynamic.

Optionally, incoming images are analyzed for colour-content, viewable-object-identity, semantics, image-features, text content, etc. and either the entire image is processed according to a discernible shade set or different regions are processed with different discernible shade sets according to complexity of image, processing delay etc.

Optionally, mapping from image-pixel-colours to discernible shades is based on determining primary image content discretely or in combination with an established operating mode/user input etc. Optionally, the image may be pre-processed in a separate pipeline to extract salient content and establish the discernible shade set in dependence upon the salient content of the image.

Optionally, two colour-translations are algorithmically selected-from, for example a "maximum contrast" set, and a "maximum hues" set, the former may be used under challenging conditions to maximise likelihood of user sensing differences in the image or to establish essential content is acquired when images are highly dynamic (e.g. a user turning and searching for something), and the latter used when the user desires to perceive the subtlety of colouration (e.g. has established where they want to search and now seeks to identify discrete objects etc.). It would be evident that greater refinement beyond a pair of colour-transformations may be employed according to the capabilities of the NR2I processing circuitry, the user preferences, etc. 2, of course.

The user should be able to "rotate and constrain" the remapping functions to each of Red, Green, and Blue, and to any angle on a colour-wheel. For example, "I want to have all my colour-perception used to detect the various shades of red (or blue, or green, or . . . ) that are in the current image." Alternately, the user can specify that the discernible hue-set should be used to maximize the likelihood of perceiving the difference between different colours across the entire spectrum, but irrespective, of luminance, say. In this case the mapping might be "blue is brighter, red is dimmer" so that chrominance has been re-mapped to luminance. Suppose the user can perceive lots of shades of blue, some ability to discern various reds, but shades of green are imperceptible. Green pixels found in the image can be re-mapped to combinations of red and blue at different intensities.

Within other embodiments of the invention artificial effects may also be introduced. If, for example, green is imperceivable, detected green objects could be covered with a pattern drawn in perceivable red and blue, such as a cross-hatching effect or "Green objects get a boundary drawn around them in red, with inward-pointing-arrows in blue" or "flash blue then red" etc. Generally, the NR2I will look up imperceivable hues from the user's stored profile; find and outline regions and objects in image with this colouration, and then apply secondary effects such as edge-detection, cartooning, and colour-remapping on these regions to make them perceivable to user.

In any of the above, enhance/augment the set of discernable hues by applying temporal variation that maps to the chromatic difference in object-image. For example, a user sees only red and blue. The amount of green present in a pixel could be represented by varying the amplitude of modulation and frequency of modulation of red and blue, which are discernible. For example, high-saturation green is represented as fast amplitude variation, low-saturation green by slower amplitude variations or alternatively the depth of amplitude modulation could be varied while frequency constant, or a combination of frequency modulation and amplitude modulation. It would be evident that these techniques could be applied to whole objects, image-regions, specific colour-regions in image, edges of objects, etc. Enhancement may include mapping a colour palette to spatial variations as well. High-contrast edges may exploit minimum and maximum (or a set of highly) discernible shades in alternation or sequenced in space and time.

The colouration of the targets used within the training may be varied and results compared to detect and compensate for any chromatic variations in optics or user perception. It would also be evident that multiple maps may be maintained, or adjusted, for instance to account for chromatic aberration in the NR2I optics pipeline.

Figure 32:
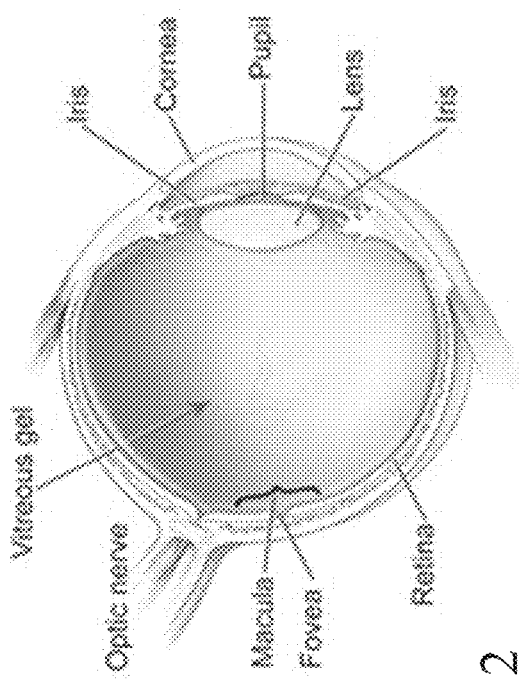
FIG. 32 depicts a cross-section of a human eye indicating its non-spherical nature.

Now referring to FIG. 32 there is depicted a cross-section of a human eye indicating its non-spherical nature. Accordingly, deformation of the image reflected off the eye is caused by variations in the surface of the eye, e.g. the bump caused by the cornea. Hence, as discussed supra by shining structured light off the eye, and observing the deformation of the reflection, the distorted reflected image may be correlated to a position and orientation of the user's eye. This light may be structured as dots in known locations, straight lines, curved lines, or even an arbitrary, but known image, for example the real-world FOV scene as both captured by a camera and as reflected by the eye and captured by a different camera. This may remove the requirement for additional NIR sources and detectors. However, if the FOV image is dim or dark then no eye tracking can be performed in that scenario absent dedicated eye-tracking/gaze-tracking elements within the NR2I.

Figure 33:
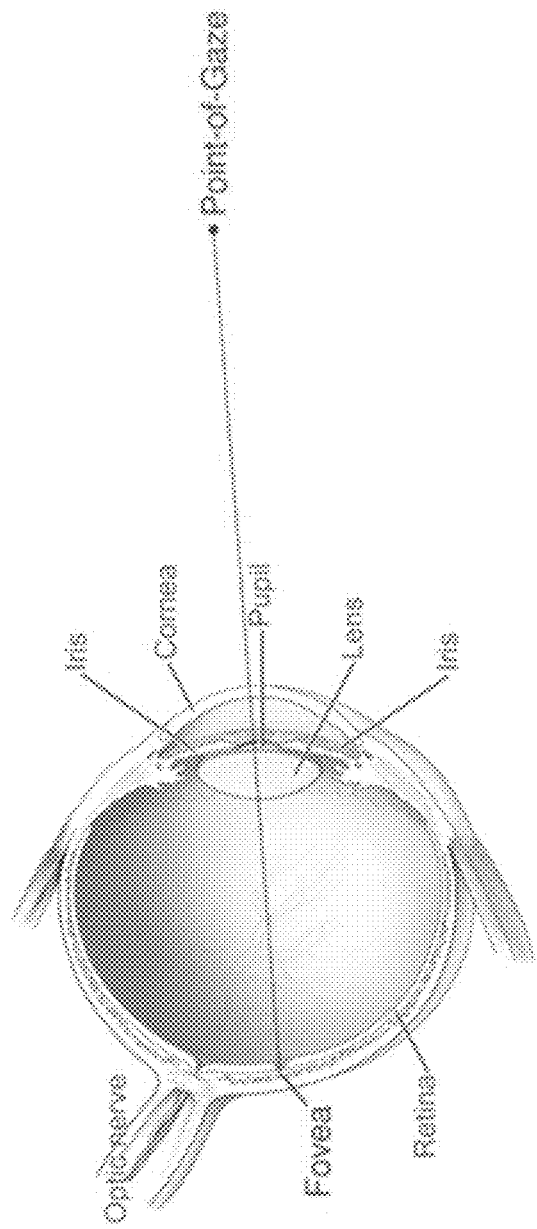
FIG. 33 depicts a cross-section of human eye of a user without macular degeneration to depict the relationship between their point of gaze, pupil and fovea maculate and how a user's preferred retinal location (PRI) can be automatically mapped within a NR2I-HMD system according to an embodiment of the invention.

Referring to FIG. 33 depicts a cross-section of human eye of a user without macular degeneration to depict the relationship between their point of gaze, pupil and fovea maculate and how a user's preferred retinal location (PRI) can be automatically mapped within a NR2I-HMD system according to an embodiment of the invention. In well-sighted individuals, the geometry is as-shown, where the direction of their gaze/interest is on a line from the fovea/macula i.e. the region of highest cone-density and resolution through centre of cornea. However, with macular degeneration or other defects/diseases affecting the user's vision then they will over a period of time established what is referred to by the inventors as a "preferred retinal location" PRL. This represents where they prefer to view their FOV and this may not align with their Point of Gaze (POG) or "optical axis" as shown in FIG. 33. For example, with macular degeneration in order to see the user will gaze, for example, left such that the image is received upon their functioning retina rather than the dead macula region. Accordingly, establishing a PRL in association with their POG becomes important to ensure that as the user's gaze adjusts that the image is projected to regions of the retina that work so that the user can actually see.

Figure 34:
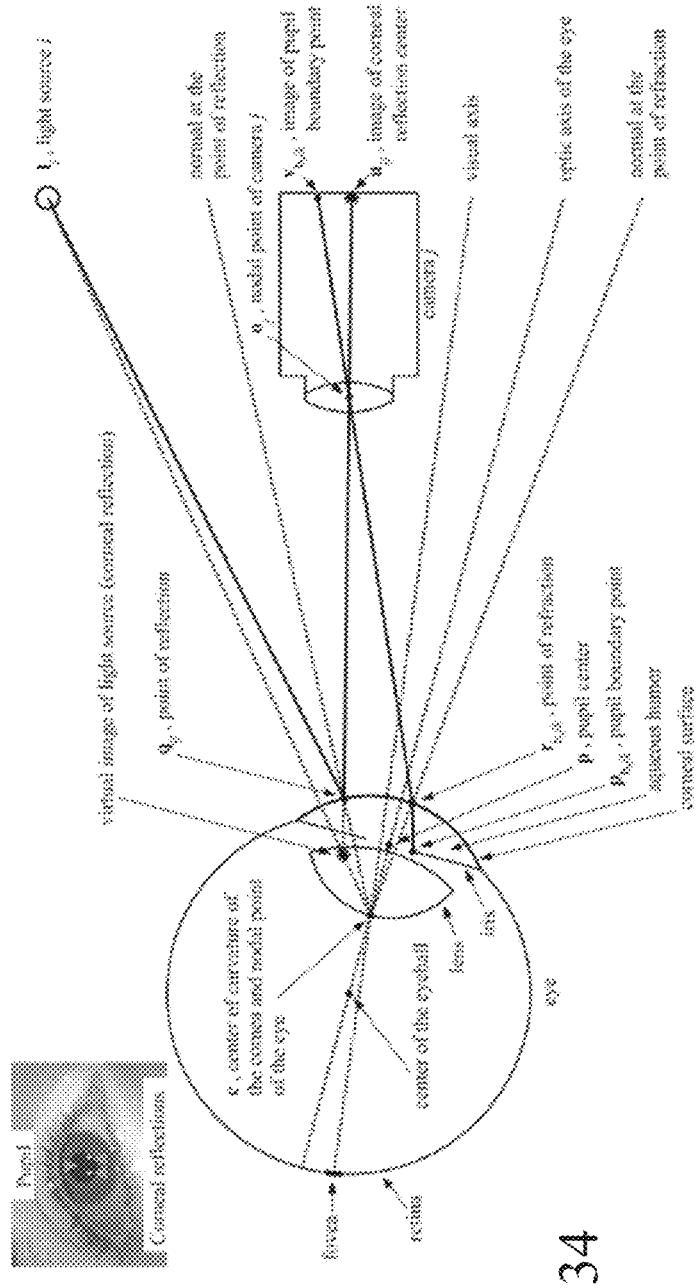
FIGS. 34 and 35 depict ray-tracing diagrams (not to scale) showing schematic representations of an eye, a camera and a light source together with an inset eye image indicating the pupil and two corneal reflections which is then disrupted with multiple reflections and spatial displacements arising when the user wears prescription lenses in combination with a NR2I-HMD according to an embodiment of the invention.
Figure 35:
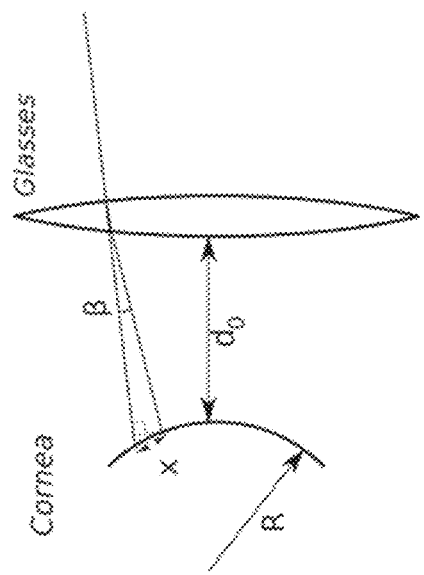

Now referring to FIGS. 34 and 35 there are depicted ray-tracing diagrams (not to scale) showing schematic representations of an eye, a camera and a light source together with an inset eye image indicating the pupil and two corneal reflections which is then disrupted with multiple reflections and spatial displacements arising when the user wears prescription lenses in combination with a NR2I-HMD according to an embodiment of the invention. Accordingly, when considering prescription lenses or any other lens or optical element disposed between the freeform prism lens or other optical combiner structure and the user's eye.

Accordingly, prescription glasses even with coatings, which are generally targeted for visible region of the electromagnetic spectrum only, provide spurious reflections (not shown) and distort the position of the corneal reflection and/or pupil edge locations (as-shown). Within an embodiment of the invention multiple structured light sources may be selectively illuminated in sequence in order to auto-detect the presence/absence of prescription glasses etc., establish locations of spurious reflections for later filtering, and form part of the configuration of the NR2I to the user. A temporal lighting sequence may also be defined to minimize interference between corneal and lens reflections. Corrections in respect of eye tracking in terms of x and y will typically depend upon the lens diopter, lens shape etc. as well as the specific geometry of NR2I to glasses, eye etc. Prescription lenses may achieve same diopter with a variety of lens shapes and some will cause reflections, others nasty reflections, and some no issues. The lens-surface facing the NR2I may be convex, concave, or flat, as may the other facet towards the user's eye. An ability to enter the user's prescription lens-shape and prescription may be employed to minimize spurious reflections within an eye-tracking system as a subset of potential illumination sources may be employed. For example, a linear array of NIR LEDs may be employed with specific LEDs activated for certain lens prescriptions and others for other lens prescriptions. Alternatively, they may be selectively activated to see which do or not generate spurious reflections. This may be undertaken with an optometrist, for example, using an IR camera to view the user's face with a trial NR2I absent the frame/cover so that the optical signals can be visualized. In some embodiments of the invention it may be beneficial for a user's prescription lenses to further include a discrete IR anti-reflective coating to one or both sides of prescription lens to reduce glare or a broad visible-NIR anti-reflective coating on the outer surface.

In order to calibrate the eye-tracking system to accommodate varying eye-relief, IPD, possibly interposed prescription lenses, and other effects, an automated eye-tracking training and calibration process may be employed. In this process the user is displayed a series of images with objects-of-interest located in a variety of known positions within the display area. The user is instructed to gaze at these objects, which might be simple dots, or cross-hairs or other targets, presented in colour and contrast so they are easily discernable by the user, while the eye-tracking system self-calibrates at each location. A plurality of display/calibration points are exercised, and the eye-tracking system builds a map, using interpolation, extrapolation, curve-fitting and similar means to form complete mapping from all display-points to received-eye-tracking-coordinates. This calibration-map can then be used in inverse to estimate the location of a user's gaze within the display area from the received eye-tracking location, accommodating and compensating for all distortions within the system. Separate training and calibration maps may be created for use with and without interposed prescription lenses. The eye-track calibration map may be part of a user's profile, so that new maps are automatically loaded using user IDs or biometric user recognition should different users employ the same NR2I display.

Figure 36:
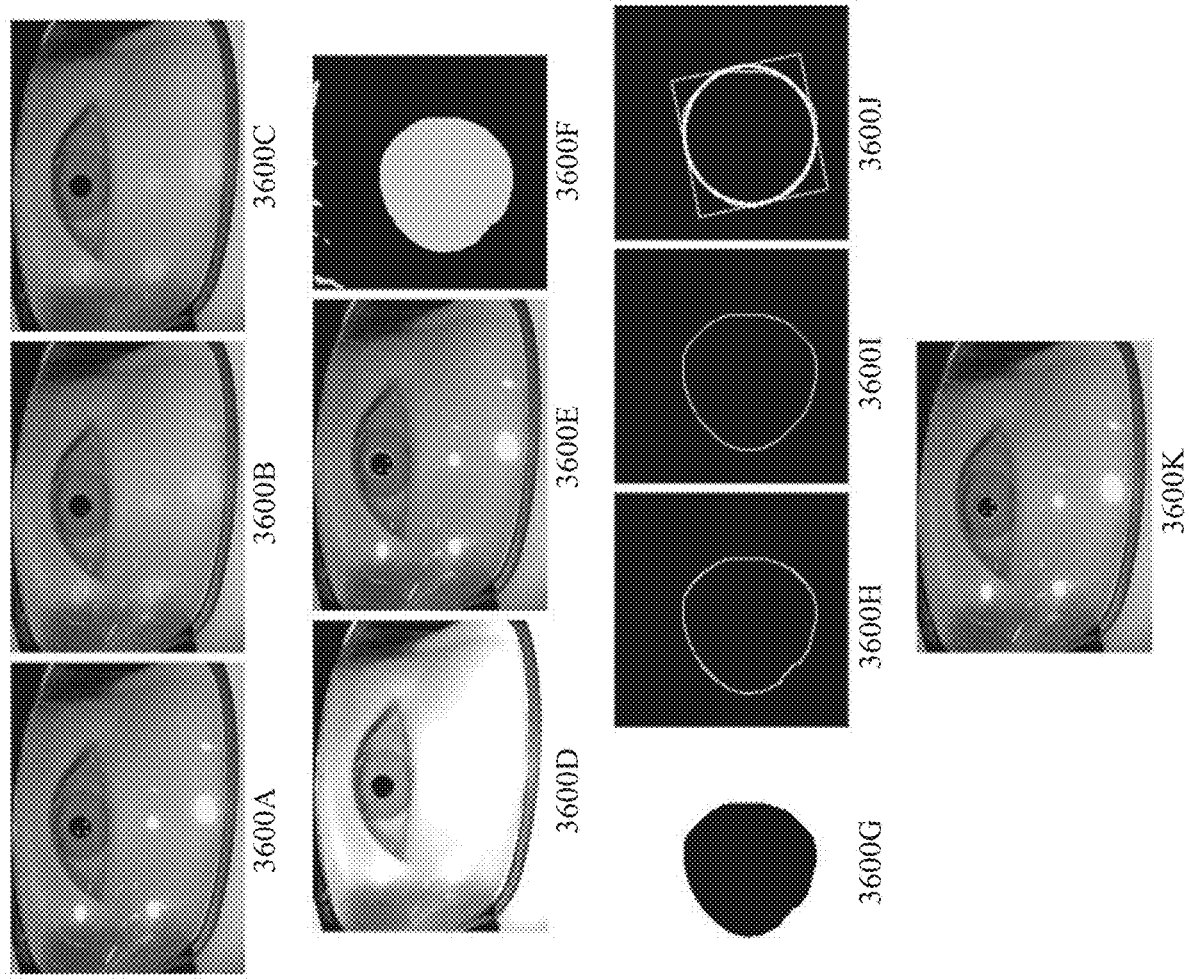
FIG. 36 depicts examples of images obtained from an exemplary pupil detection process depicting the (a) Original image; (b) After erasure of the SR regions; (c) Image resulting from morphological operations; (d) Image resulting from histogram stretching; (e) Pupil area that is detected by the CED method; (f) Binarized image of the predetermined area (based on the detected pupil region) from (d); (g) Image resulting from morphological erosion and dilation of (f); (h) Result from component labeling and canny edge detection; (i) Result from the convex hull method; (j) Result from ellipse fitting; (k) Result of the pupil detection process.

Now referring to FIG. 36 there are depicted examples of images obtained from an exemplary pupil detection process depicting:

First image 3600A: Original image acquired;
Second image 3600B: After erasure of the specular reflection (SR) regions;
Third image 3600C: Image resulting from morphological operations;
Fourth image 3600D: Image resulting from histogram stretching;
Fifth image 3600E: Pupil area that is detected by the circular edge detection (CED) method;
Sixth image 3600F: Binarized image of the predetermined area (based on the detected pupil region) from 3600D;
Seventh image 3600G: Image resulting from morphological erosion and dilation of 3600F;
Eighth image 3600H: Result from component labeling and canny edge detection;
Ninth image 3600 I: Result from the convex hull method;
Tenth image 3600J: Result from ellipse fitting; and
Eleventh image 3600 K: Result of the pupil detection process.

The NR2I selectively illuminates the NIR LEDs thereby allowing detection of the spurious reflections from the eye so that these can be eliminated. These are also removed by discarding pixel-values above a threshold, smoothing and blending these images (first to third images 3600A to 3600C). The resulting blending smoothed image is then contrast stretched (fourth image 3600D) before the circular edge detection process is performed (fifth image 3600E). This may be employed directly, or the image/data further processed through binarization, edge detection, convex hulling, and fitting an ellipsoid (sixth to tenth images 3600F to 3600J). The pupil is then defined as being at the centre of the ellipsoid, i.e. halfway between two foci.

Figure 37:
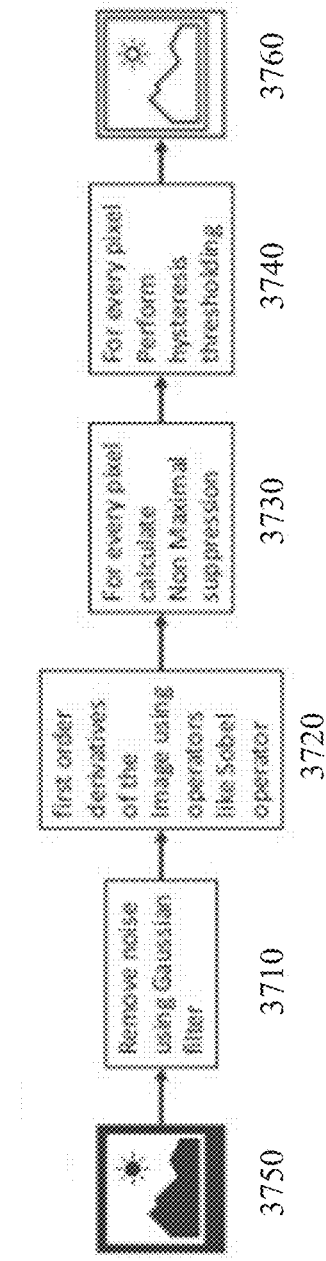
FIG. 37 depicts exemplary software segment and process flow for a canny edge detection process which may form part of automated processes within a NR2I-HMD according to an embodiment of the invention.

FIG. 37 depicts exemplary software segment and process flow for a canny edge detection process which may form part of automated processes within a NR2I-HMD according to an embodiment of the invention such as described supra in respect of pupil detection process in FIG. 36. Such a process may also be employed in processing an image to determine image content etc. As depicted the process flow comprises first to fourth steps 3710 to 3740 applied to an acquired image 3750 to yield an edge detected image 3760, these being:

First step 3710: Remove noise by applying a Gaussian filter;
Second step 3720: Generate first order derivatives of the image using operators, e.g. the Sobel operator;
Third step 3730: For every pixel calculate a non-maximal suppression;
Fourth step 3740: For every pixel perform hysteresis thresholding.

Now referring to FIGS. 38 and 39 there are depicted alternate binocular image projection techniques that may be employed within a NR2I-HMD system according to embodiments of the invention. Referring to FIG. 38 the left and right optical displays are driven with the same image thereby generating identical left and right images 3810L and 3810R to the user's eyes which are then fused by the user's visual processes to perceived image 3820. In contrast in FIG. 39 partially overlapping images from an originally wider-field of view are presented to the left and right eyes as represented by left and right images 3910L and 3910R. These are then perceived as merged image 3920 which provides a wider FOV and is closer to the normal human visual process as the other left and right portions of the image may be likened to the left and right peripheral image information acquired by the user's normal process. Accordingly, the monocularity of portions of the extreme portions of the image is natural.

Figure 40:
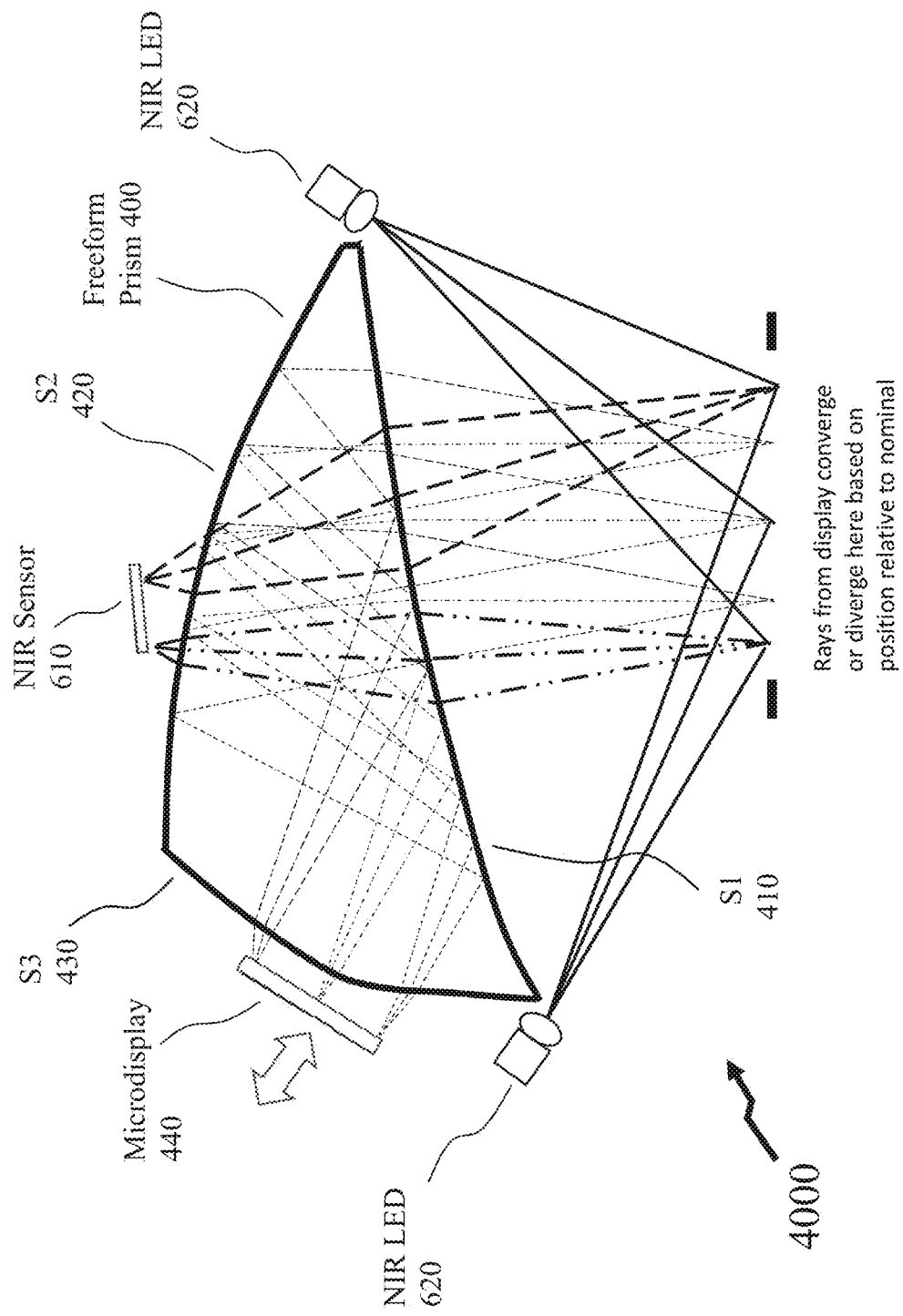
FIG. 40 depicts a freeform lens assembly according to an embodiment of the invention for an exemplary NR2I-HMD employing multiple sources of NIR light directly coupled to the user's eye together with an imaging sensor upon the rear facet for determining the user's eye's "optical depth" relative to the freeform lens allowing adjustment of the display device to correct for a user's prescription.

FIG. 40 depicts a freeform lens assembly according to an embodiment of the invention for an exemplary NR2I-HMD employing multiple sources of NIR light directly coupled to the user's eye together with an imaging sensor upon the rear facet for determining the user's eye's "optical depth" relative to the freeform lens allowing adjustment of the display device to correct for a user's prescription. Accordingly, in common with the previous embodiments of the invention depicted in respect of FIGS. 7 to 11 the wedge shaped freeform prism is depicted horizontal with a lateral FOV with the image from the MicroDisplay 440 undertaking dual reflections before being coupled to the user's eye. The NR LEDs 620 are directly coupled to the user's eye without passing through the Freeform Prism 400 whilst the NIR Sensor 610 is disposed adjacent to surface S2 420 such that the reflected signals from the user's eye are directly coupled through surfaces S1 410 and S2 420. In contrast to the previous embodiments of the invention depicted in respect of FIGS. 7 to 11 the MicroDisplay 440 can translate normal to surface S3 430. Accordingly, moving the MicroDisplay 440 closer/further from the Freeform Prism 400 causes a focal length adjustment which is corrected by the user's eye in opposition to their normal prescription. Accordingly, the focal length of the optical train (pipeline) is accordingly adjusted to accommodate the user's prescription.

Optionally, variants of the configuration depicted in FIG. 40 may be implemented to respond to eye-tracking variations. Optionally the motion may be motorized, use piezo-electric actuation, or it may be manual/mechanical. Within an alternate embodiment of the invention a dual-opposing-wedge structure may be employed to provide finer control, and translation of the wedge or wedges in one direction being converted to an orthogonal direction. In respect of automation then the user may be identified through iris and/or retina scanning or an alternate configuration method. Accordingly, based upon the user identity and the retrieved configuration settings the MicroDisplay 440 may adjust to compensate for the user's prescription. During fitting of the NR2I-HMD the user may be presented with reference images wherein the MicroDisplay 440 position is adjusted and user feedback employed to establish the preferred position.

As noted supra in respect of embodiments of the invention a user of a NR2I system may be near or far-sighted and require corrective lenses interposed between eye and NR2I display. The optical paths between eye and eye-tracking system will be affected by interposed lenses. The user's diopter prescription may be configured, and/or optical-path distortion of the eye-tracking system be detected in order to provide compensation for the corrective lenses.

Alternatively, especially in the case of immersive NR2I where forward-view diopter correction is not required but the user requires prescription lenses, the optical paths of the NR2I display may be configured to provide uncollimated light towards the user and diopter-correction achieved through an adjustment of the eye-relief, or z-distance between eye and display assembly, see for example FIG. 40. A small selection of optical trains or settings of varying power, along with variable eye-relief could accommodate a larger variety of prescriptions. By accommodating the user's prescription within the NR2I display as opposed to interposing corrective lenses, the eye-tracking system is simplified.

Embodiments of the invention may be implemented to support NR2I eye-tracking and the NR2I system may alternately be made adaptive to the user's specific geometry and (optional) prescription lenses by following the process:

Step A: Determine user's prescription;
Step B: Fit prescription lenses to user and/or HMD (lens designed, may be coated for min IR reflection of eye-tracking light);
Step C: Perform user-calibration of all device display-geometry parameters (IPD, vergence, relief, height, torsion, etc. Some may be electronic, some are mechanical, used in combination);
Step D: Display images with targets for user focus/gaze at a plurality of locations using the HMD;
Step E: Track user's gaze direction during focus on these locations using IR eye-tracking;
Step F: Create a table of target image locations and measured gaze directions;
Step G: Form and store a compensation map from image to gaze for that user, at that prescription, at that given NR2I-to-eye geometry (which may also vary, for example with bioptic display angle); and
Step H: Repeat for other users, prescriptions, geometries, bioptic angle settings.

Optionally, the compensation-map may be interpolated, a polynomial spline, or other function of the coordinate-pairings. Similarly, within other embodiments of the invention target images to determine gaze and/or PRL may be simple forms e.g. cross-hairs where the fixation-location is fixed, or more complex tasks such as reading where the user indicates the fixation location by reading aloud the word or letter, or musical note, for example.

Within other embodiments of the invention a combination function of eye-tracking and bioptic may be employed such that as the display assembly is rotated, the geometry with respect to the user's eye changes, and the system compensates. There are at least two ways these features can interact. By measuring the rotation angle (either directly with an encoder, say, or inferring based on, for example, inertial sensing, or from eye-tracking itself) we can know that the display has been shifted with respect to the user's eye. Using knowledge of the amount of rotation and/or translation between user-frame and display-frame, image processing can be altered to optimize viewing in the new position. Further, knowledge of the rotation/translation can be used to alter the parameters of the eye-tracking itself, for instance in a structured-light based eye-tracking approach, the pupil-tracking algorithm can be altered to accommodate the new display-eye geometry. Optionally, auto-detection of the bioptic angle may be performed by observing reflections off the user's eye of either the world, main display or the IR LEDs.

Within an embodiment of the invention a NIR eye-tracking compensation process for a bioptic NR2I may comprise a process having the following step:

Step 1: Move display to bottom and note reflection locations as eye is moved to focus on image-targets placed on display for this purpose;
Step 2: Move display to middle and note reflection locations as above;
Step 3: Move display to upper usable position and note reflection locations as above;
Step 4: Move display to out-of-use-up position and note reflection locations as above;
Step 5: Build a map from received reflection-locations versus eye direction and bioptic angle;
Step 6: Store the map, which may be user-specific or generic for multiple users.

Accordingly, when eye-tracking:
Step 7: Determine the bioptic angle using either this map-based approach or other means (e.g. angle- or inertial-sensor) before interpreting reflections; and
Step 8: Compensate the eye-tracking system for NR2I bioptic angle (or another physical reconfiguration) based on measured or estimated-from-eye-tracker-itself angle The fixation-locations for calibration may be preferentially selected around the periphery to determine extrema of the mapping functions. The targets may decrease in size during training to assist in user-focus. The targets may be moved in order to train the eye-tracking system in the user's saccade-patterns for the purpose of filtering these and determining true PRL (saccade-learning/filtering can also be performed within the controller if appropriate.

Where the NR2I employs image-shifting for the purpose of vergence adjustment or stereoscopy, the eye-tracking system may be compensated for such shifts. The eye-tracking system may also be used to track the eye and perform vergence adjustment image-shifts based on the detected user's gaze. Adjustment may be in combination with depth-map of observed image (focus on closer objects, eyes converge, further, diverge). Left/right, up down, converging, diverging, all shifts are possible.

In accordance with embodiments of the invention, the position and orientation of the user's eye is tracked by any of several means. This information is used within embodiments of the invention to assist and automate any of several tasks.

In accordance with embodiments of the invention with respect to focusing the region of interest to the user may be inferred from the direction of gaze or PRL. The optics pipeline may be controlled using this information to bring into best focus and clarity this region. In one embodiment where a camera is used to create a digital display of a real-world scene (or other 3-D scene possibly right in front of the user, or . . . ) around the user, the camera's focus can be adjusted to focus at the depth of the objects located at the user's region of interest. A depth-map of the image content created by the camera may be obtained through any of a number of means. As the user's eye pans over the image, the focus can be dynamically adjusted so that the camera's focal depth is adjusted to match the depth-map of the captured scene. Image-depth-through defocus-metrics may be used in this.

In accordance with embodiments of the invention with respect to the physical configuration then it would be evident to one skilled in the art that it is advantageous in NR2I systems to align the eye box of the display with respect to the user's eyes. Embodiments of the invention allow lateral adjustment of the displays to align with the user's IPD, and the eye box of each of the right and left displays, if both present, with the user's right and left eyes, respectively. Vertical and fore-and-aft adjustment is made possible through, for example, an adjustable nose-bridge and/or temple arms and/or demountable display assembly and/or bioptic hinge. The user's eye position with respect to the display may be measured using the IR sensor and user feedback provided through visual (through the NR2I display itself), audio and/or tactile mechanisms (e.g. vibration). In a manually-adjusted configuration, the user is provided with feedback indications of what fitting adjustments to make in order to bring the NR2I into proper alignment with their face, head, and eye geometries. Arrows on the screen can indicate required direction of adjustment, or vibration on left or right temple-arms for left or right adjustment, respectively.

In accordance with embodiments of the invention with respect to eye-tracking, gaze-direction etc. then a NIR sensor may be used to image the user's eye, for example the iris or retina. This image acquired from the user may be used in a number of ways including but not limited to:
   The image may be compared against one or more stored reference images to identify the user;
   Features may be extracted from the image to be compared against reference features, as opposed to direct image comparisons;
   Unauthorized users whose image or stored features do not match a stored reference may be refused access to the N2I display;
   Once identified, the user's ID may be used to store and later customize the display to the user's specific head and eye geometry and preferences, and other user interface preferences and settings (contrast, colour, other image processing, application and menu preferences and settings);
   Where the N2I includes motorized adjustments, the ID allows automatic physical adjustments; and
   Where the N2I includes manual adjustments, the User identity can provide feedback specific to the user from their stored profile, i.e. target images or instructions for adjustment.

In accordance with embodiments of the invention with respect to eye-tracking, gaze-direction, NIR illumination etc. for the calibration and user-specific device tuning then it would be also evident that these can be employed to perform diagnostics with respect to the user. These may include, but not be limited to:
   Strabismus (deviating eyes) which may be inward (esotropia), outward (exotropia), up (hypertropia), down (hypotropia), intorted, or extorted (in- and excyclotorsion respectively);
   Comitant strabismus is constant over gaze, incomitant varies by direction. IDEA: develop map of exact strabismus depending on gaze location, vary the individual PRL for each eye;
   Perform Hirschberg or Krimsky tests to detect strabismus (ocular misalignment) through corneal reflex testing;
   Cover/uncover testing used to detect tropia wherein the non-preferred eye does not move when covered/uncovered. Orthophoric users' eyes will not shift, but remain on ROI object. Alternating tropia is when either eye will move to fixate when the other is covered. Alternating cover testing can be employed to detect phorias;
   "Pseudo-Isochromatic Ishihara Plates" to detect colour-sensitivity with a pattern in noise.

Within embodiments of the invention user-phorias may be detected through combination of image projections that alternate between left and right eyes whilst observing gaze direction for each eye, and noting vergence. Sample images to be presented to the user for detecting these and other conditions were discussed supra in respect of FIGS. 24 to 30.

In accordance with embodiments of the invention with respect to colour a NR2I may be employed in order to:
   Create images to be presented to user in succession with colour-variation but not intensity/luminance variation between images or sub-portions of the images;
   Alternate images to determine the limits of the user's colour sensitivity in different areas of the colour-palette, R, G, B, Yellow, Purple, etc. Reduce the colour- and intensity-differences until they are undetectable by the user. Back up one. That is the user limit. Hone in on the "edge of detectability" by reducing step sizes;
   Determine the user's greatest colour-differentiation (e.g. measure flight-time of eye to hit target, fastest-to-target means most discernible, using eye-tracking), or use standard embedded-image-in-dots test to find the right colours for max detection;
   Create a map, specific to the user, of the full colour-intensity gamut to that colour-intensity gamut that is discernible to the user (in those conditions, in that mode . . . );

Re-map image colours and intensities from source-gamut to user-gamut on images presented to users so they can see them more clearly;

When "alerts" or "alarms" or important notices or highlighting of objects is required, use the pre-determined user-detectability palette to select those colours that are most in contrast/discernible to the user. Flash or highlight or edge-enhance or re-colour the important information in the user's preferred colours;

Auto-load all things like preferred colour-sets based on user identity, either auto-detected (pupil and iris through eye-track, say) or manually configured.

A NR2I HMD may not fit straight on certain users and accordingly embodiments of the invention allow individual torsion-control on each display in addition to IPD adjustments etc. Optionally, eye-tracking systems may compensate for such rotation.

As discussed supra a user's pupil may be mapped and accordingly its size may be tracked using the eye-facing camera. The user may be stimulated with differing intensities and colours of light from the micro-display and the pupil dilation response tracked. The user's dilation response may be stored for historical comparison, or compared to standard metrics for evaluation of health, evidence of concussion, inebriation, etc. A similar process may be employed for dot-tracking response.

Within embodiments of the invention a NR2I HMD may employ one or more elements including but not limited to one or more displays, image content from one or more sources, input interface (internal e.g. camera or external e.g. PDF over some communications link or from memory) to receive image content, processing (image and logic), non-volatile and volatile memory, stored algorithms, user preferences, user identity information (biometric or simple user identity and password). Sensors to determine ambient conditions, motion and position (inertial/magnetic sensor, real-world structured light processing, internal sensors e.g. bioptic hinge angle). Forward-facing sensors: one or more visible light cameras, IR cameras, sonar or IR range finder depth-mapper, depth map based on direct sense or inferred from captured-image defocus information, eye tracking subsystem compensated for bioptic and prescription lenses. Vector or array image-processing. Use of rendering pipeline for image processing as described in "aberration correction" patent. Parallelization of eye-tracking algorithms using rendering pipeline. NR2I HMDs may employ any subset of these.

Figure 41:
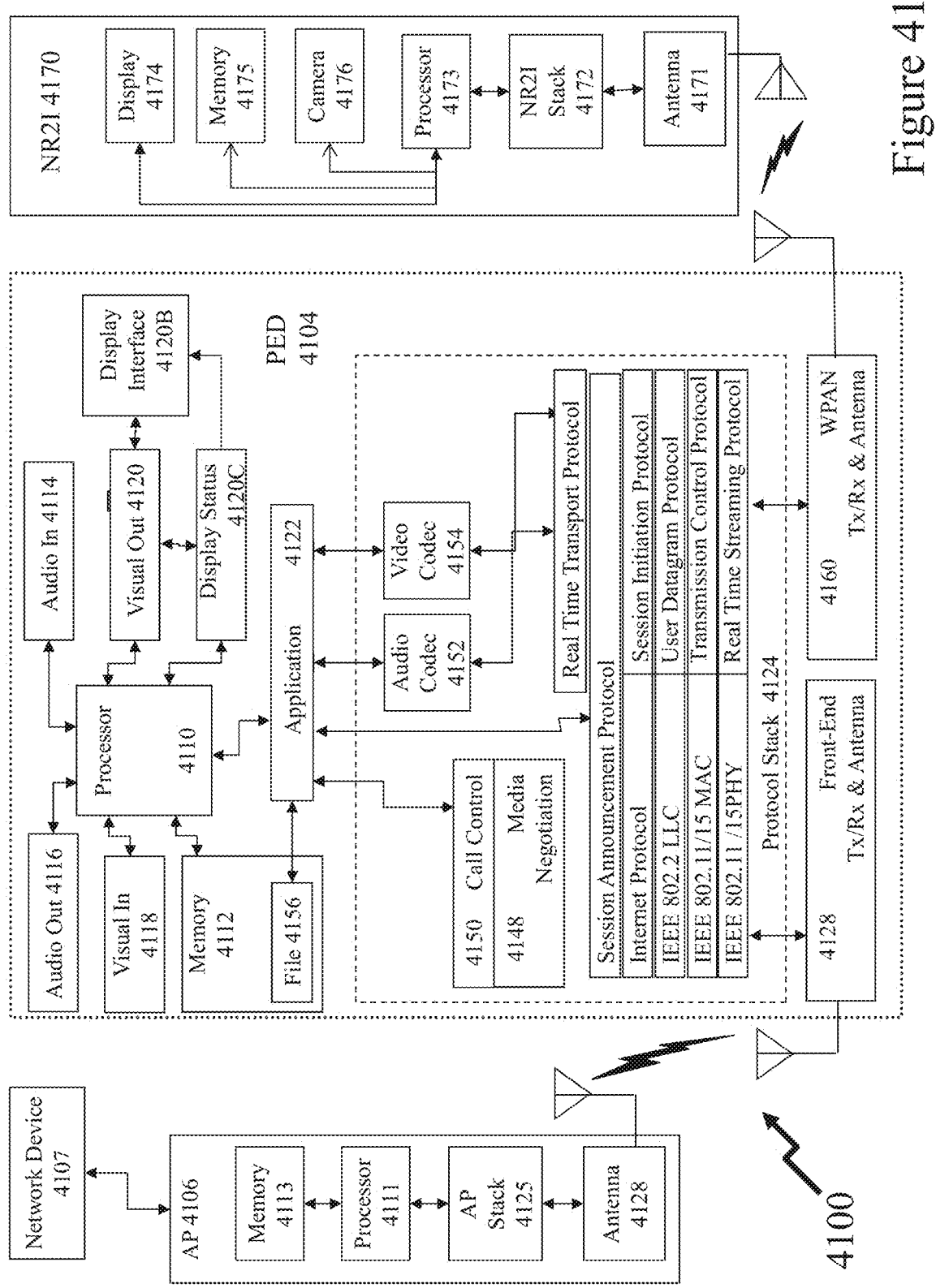
FIG. 41 depicts a portable electronic device supporting a head mounted device according to an embodiment of the invention.

Referring to FIG. 41 there is depicted a portable electronic device 4104 supporting an interface to a NR2I 4170 according to an embodiment of the invention. Also depicted within the PED 4104 is the protocol architecture as part of a simplified functional diagram of a system 4100 that includes a portable electronic device (PED) 4104, such as a smartphone, an Access Point (AP) 4106, such as a Wi-Fi access point or wireless cellular base station, and one or more network devices 4107, such as communication servers, streaming media servers, and routers for example. Network devices 4107 may be coupled to AP 4106 via any combination of networks, wired, wireless and/or optical communication. The PED 4104 includes one or more processors 4110 and a memory 4112 coupled to processor(s) 4110. AP 4106 also includes one or more processors 4111 and a memory 4113 coupled to processor(s) 4111. A non-exhaustive list of examples for any of processors 4110 and 4111 includes a central processing unit (CPU), a digital signal processor (DSP), a reduced instruction set computer (RISC), a complex instruction set computer (CISC) and the like.

Furthermore, any of processors 4110 and 4111 may be part of application specific integrated circuits (ASICs) or may be a part of application specific standard products (ASSPs). A non-exhaustive list of examples for memories 4112 and 4113 includes any combination of the following semiconductor devices such as registers, latches, ROM, EEPROM, flash memory devices, non-volatile random-access memory devices (NVRAM), SDRAM, DRAM, double data rate (DDR) memory devices, SRAM, universal serial bus (USB) removable memory, and the like.

PED 4104 may include an audio input element 4114, for example a microphone, and an audio output element 4116, for example, a speaker, coupled to any of processors 4110. PED 4104 may include a video input element 4118, for example, a video camera, and a visual output element 4120, for example an LCD display, coupled to any of processors 4110. The visual output element 4120 is also coupled to display interface 4120B and display status 4120C. PED 4104 includes one or more applications 4122 that are typically stored in memory 4112 and are executable by any combination of processors 4110. PED 4104 includes a protocol stack 4124 and AP 4106 includes a communication stack 4125. Within system 4100 protocol stack 4124 is shown as IEEE 802.11/15 protocol stack but alternatively may exploit other protocol stacks such as an Internet Engineering Task Force (IETF) multimedia protocol stack for example. Likewise, AP stack 4125 exploits a protocol stack but is not expanded for clarity. Elements of protocol stack 4124 and AP stack 4125 may be implemented in any combination of software, firmware and/or hardware.

Applications 4122 may be able to create maintain and/or terminate communication sessions with any of devices 4107 by way of AP 4106. Typically, applications 4122 may activate any of the SAP, SIP, RTSP, media negotiation and call control modules for that purpose. Typically, information may propagate from the SAP, SIP, RTSP, media negotiation and call control modules to PHY module 4126 through TCP module 4138, IP module 4134, LLC module 4132 and MAC module 4130. It would be apparent to one skilled in the art that elements of the PED 4104 may also be implemented within the AP 4106.

Also depicted is NR2I 4170 which is coupled to the PED 4104 through WPAN interface between Antenna 4171 and WPAN Tx/Rx & Antenna 4160. Antenna 4171 is connected to NR2I Stack 4172 and therein to processor 4173. Processor 4173 is coupled to camera 4176, memory 4175, and display 4174. NR2I 4170 being for example NR2I 370 described above in respect of FIG. 3. Accordingly, NR2I 4170 may, for example, utilize the processor 4110 within PED 4104 for processing functionality such that a lower power processor 4173 is deployed within NR2I 4170 controlling acquisition of image data from camera 4176 and presentation of modified image data to user via display 4174 with instruction sets and some algorithms for example stored within the memory 4175. It would be evident that data relating to the particular individual's visual defects may be stored within memory 4112 of PED 4104 and/or memory 4175 of NR2I 4170. This information may be remotely transferred to the PED 4104 and/or NR2I 4170 from a remote system such as an optometry system characterising the individual's visual defects via Network Device 4107 and AP 4106. For example, the eSight Generation 3 NR2I supports a wired USB connection to the PED/FED as well as a Bluetooth connection. Accordingly, a Wi-Fi connection to the NR2I 4170 would be via the PED/FED and either the Bluetooth or wired connection. These interfaces (or others, e.g. HDMI, etc.) may be used to either provide image-data to the NR2I display for enhancement and display, or may be used to transmit the image being presented to the user to another device or display ("display replication") or both. Display-replication can be particularly useful during clinician-assisted training calibration, and device setup, described in-supra.

Optionally, the processing of image data may be solely within the NR2I 4170, solely within the PED 4104, distributed between them, capable of executed independently upon both, or dynamically allocated according to constraints such as processor loading, battery status etc. Accordingly, the image acquired from a camera associated with the NR2I 4170 may be processed by the NR2I 4170 directly but image data to be displayed acquired from an external source processed by the PED 4104 for combination with that provided by the NR2I 4170 or in replacement thereof. Optionally, processing within the NR2I 4170 may be off-loaded to the PED 4104 during instances of low battery of the NR2I 4170, for example, wherein the user may also be advised to make an electrical connection between the NR2I 4170 and PED 4104 in order to remove power drain from the Bluetooth interface or another local PAN etc.

Accordingly, it would be evident to one skilled the art that the NR2I with associated PED may accordingly download original software and/or revisions for a variety of functions including diagnostics, display image generation, and image processing algorithms as well as revised ophthalmic data relating to the individual's eye or eyes. Accordingly, it is possible to conceive of a single generic NR2I being manufactured that is then configured to the individual through software and patient ophthalmic data. Optionally, the elements of the PED required for network interfacing via a wireless network (where implemented), NR2I interfacing through a WPAN protocol, processor, etc. may be implemented in a discrete standalone PED as opposed to exploiting a consumer PED. A PED such as described in respect of FIG. 20 allows the user to adapt the algorithms employed through selection from internal memory as well as define an ROI through a touchscreen, touchpad, or keypad interface for example.

Further the user interface on the PED may be context aware such that the user is provided with different interfaces, software options, and configurations for example based upon factors including but not limited to cellular tower accessed, Wi-Fi/WiMAX transceiver connection, GPS location, and local associated devices. Accordingly, the NR2I may be reconfigured upon the determined context of the user based upon the PED determined context. Optionally, the NR2I may determine the context itself based upon any of the preceding techniques where such features are part of the NR2I configuration as well as based upon processing the received image from the camera. For example, the NR2I configuration for the user wherein the context is sitting watching television based upon processing the image from the camera may be different to that determined when the user is reading, walking, driving etc. In some instances, the determined context may be overridden by the user such as, for example, the NR2I associates with the Bluetooth interface of the user's vehicle but in this instance the user is a passenger rather than the driver.

It would be evident to one skilled in the art that in some circumstances the user may elect to load a different image processing algorithm and/or NR2I application as opposed to those provided with the NR2I. For example, a third-party vendor may offer an algorithm not offered by the NR2I vendor or the NR2I vendor may approve third party vendors to develop algorithms addressing particular requirements. For example, a third-party vendor may develop an information sign set for the Japan, China etc. whereas another third-party vendor may provide this for Europe.

Optionally the NR2I can also present visual content to the user which has been sourced from an electronic device, such as a television, computer display, multimedia player, gaming console, personal video recorder (PVR), or cable network set-top box for example. This electronic content may be transmitted wirelessly for example to the NR2I directly or via a PED to which the NR2I is interfaced. Alternatively, the electronic content may be sourced through a wired interface such as USB, I2C, RS485, etc. as discussed above. In the instances that the content is sourced from an electronic device, such as a television, computer display, multimedia player, gaming console, personal video recorder (PVR), or cable network set-top box for example then the configuration of the NR2I may be common to multiple electronic devices and their "normal" world engagement or the configuration of the NR2I for their "normal" world engagement and the electronic devices may be different. These differences may for example be different processing variable values for a common algorithm or it may be different algorithms.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents. Such variations and modifications of the embodiments described herein includes that specific dimensions, variables, scaling factors, ratios, etc. may be varied within different limits or that these may be approximate rather than absolute.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A near-to-eye (NR2I) display system comprising:
   a freeform prism lens (prism) disposed parallel to a transverse plane of a user;
   a micro-display proximate a first face of the prism for displaying content to a user of the NR2I system wherein light emitted from the micro-display and received by the prism emerges from the prism and subsequently impinges upon an eye of the user;
   an infra-red sensor to image a portion of the user's eye to which the prism relates, the infra-red sensor receiving infra-red light reflected from the user's eye directly from a different face of the prism than those proximate the micro-display and that proximate the user's eye with no reflection of the reflected infra-red light occurring between the user's eye and the infra-red sensor;

one or more infra-red optical sources to illuminate the user's eye;

an integrated processing capability; and computer readable instructions within a non-volatile non-transitory storage medium for execution by the integrated processing capability in order to detect a direction of a preferred retinal location of the user based upon information acquired from the infra-red sensor; wherein the one or more infra-red sources comprises at least one of:

an optical infra-red source disposed proximate a different face of the prism than that proximate to the micro-display;

an optical infra-red source illuminating the user's eye directly and not via the prism;

an optical infra-red source coupled to the user's eye via an optical waveguide disposed within an assembly comprising the prism; and an optical infra-red source coupled to the user's eye via an optical waveguide formed within the prism.

2. The NR2I display system according to claim 1, wherein the infra-red sensor does not have at least one of an optical lens and a pinhole disposed between it and the prism.

3. A near-to-eye eye-tracked head-mounted display (NR2I display), comprising:

a micro-display for generating an image to be viewed by a user, the micro-display having a display optical path and an exit pupil associated therewith;

a first plane located at the micro-display and a second plane located at the exit pupil;

an eye-facing image sensor configured to receive reflected optical radiation reflected from a user's eye, the image sensor having a sensor optical path associated therewith where the sensor optical path has no reflection between the user's eye and the image sensor;

one or more infra-red optical sources to illuminate the user's eye; and display optics disposed in optical communication with the micro-display along the display optical path and in optical communication with the image sensor along the sensor optical path, the display optics having a selected surface closest to the micro-display and the image sensor, the display optics located relative to the micro-display and image sensor such that the display and image sensor optical paths impinge upon differing respective portions of the selected surface; wherein the display optical path within the display optics is substantially parallel to a line joining the centres of the user's eyes;

the one or more infra-red sources comprises at least one of:

an optical infra-red source disposed proximate a different face of the prism than that proximate to the micro-display;

an optical infra-red source illuminating the user's eye directly and not via the prism;

an optical infra-red source coupled to the user's eye via an optical waveguide disposed within an assembly comprising the prism; and an optical infra-red source coupled to the user's eye via an optical waveguide formed within the prism; and the micro-display, image sensor, and display optics form part of a bioptic assembly allowing the user to move the NR2I display between a first position with it disposed up such that the NR2I display is not within the user's line of sight and a second position with it disposed down such that the NR2I display is within the user's line of sight.

4. The NR2I display according to claim 3, wherein the eye-facing image sensor receives reflected optical radiation from a plurality of near infra-red optical sources;

wherein the plurality of optical sources are coupled to the user's eye at least one of:

directly without passing through the display optics;

through the display optics;

through a plurality of optical waveguides disposed separate to the display optics; and through a plurality of optical waveguides integrated within the display optics.

5. The NR2I display according to claim 3, wherein the NR2I display incorporates a lens disposed between the display optics and the user's eye; and the image sensor allows for at least one of:

determination through eye-tracking of the presence of the lens; and adjustment of at least one of an estimated gaze direction and position of the micro-display relative to the display optics to compensate for the presence of the lens.

6. The NR2I display according to claim 3, wherein an adjustment of a position of the micro-display relative to the display optics from an initial position is made in order to provide an adjusted optical path, the adjusted optical path being that the user would have through the display optics with a prescription lens to their prescription disposed between the display optics and user's eye.

7. The NR2I display according to claim 3, wherein the image sensor receives reflected optical radiation from a plurality of near infra-red optical sources which are integrated with the micro-display.

8. A near-to-eye (NR2I) display system comprising:

a head mounted display; wherein the head mounted display comprises:

one or more infra-red optical sources to illuminate the user's eye;

a first assembly comprising at least a pair of temple arms that bear some or all of the weight of an attached display assembly, and a first portion of a hinged attachment to a second assembly;

the second assembly, the second assembly comprising at least a micro-display, an optical train to allow a user to view the image created by the micro-display, an infra-red sensor used to image the user's eye(s), and a second portion of the hinged attachment to the first assembly; and a processing system that determines the direction of a user's preferred retinal location within the displayed image; wherein the processing of the users preferred retinal location is performed in dependence upon the angle of the hinged attachment between the two assemblies;

the optical train comprises a freeform prism lens (prism) disposed parallel to a transverse plane of a user;

infra-red light reflected from the user's eye is coupled to the infra-red sensor via the prism without a reflection of the reflected infra-red light occurring within the prism; and the one or more infra-red sources comprises at least one of:
- an optical infra-red source disposed proximate a different face of the prism than that proximate to the micro-display;
- an optical infra-red source illuminating the user's eye directly and not via the prism;
- an optical infra-red source coupled to the user's eye via an optical waveguide disposed within an assembly comprising the prism; and
- an optical infra-red source coupled to the user's eye via an optical waveguide formed within the prism.

9. The NR2I display system according to claim 8, wherein at least one of:
- the optical train is a horizontally disposed freeform prism;
- the optical train is a horizontally disposed freeform prism with a freeform compensator for the user's direct field of view; and
- the infra-red sensor is disposed in front of the user's eye.

10. The NR2I display system according to claim 8, wherein the head mounted display comprises:
- an assembly comprising a freeform prism lens and a micro-display for projecting image-light onto a predetermined region of a first surface of said freeform prism-lens, said image light performing two internal reflections within the freeform prism-lens before exiting the freeform prism-lens for viewing by the user with an eye, wherein
- the micro-display is fixedly held in position by said assembly relative to said first surface of the freeform prism lens and proximate a temple of the user nearest the user's eye viewing the projected image-light, such assembly having attachment features such that vertical angular motion of the assembly across the user's vertical field of view when attached to a body of the NR2I system is made possible, in order to allow positioning of the display above the user's line of sight.

11. The NR2I display system according to claim 10, further comprising:
- a second assembly comprising a second freeform prism lens, a second micro-display for projecting image-light onto a predetermined region of a first surface of said second freeform prism-lens, said image light performing two internal reflections within the second freeform prism-lens before exiting the second freeform prism-lens for viewing by the user with their other eye, wherein
- the second micro-display is fixedly held in position relative to said first surface of the second freeform prism lens and proximate the user's other temple by said second assembly, such assembly having attachment features such that lateral motion of the second assembly across the user's horizontal field of view when attached to the body of the NR2I system is made possible allowing the positions and separation of the assembly and second assembly to be established in dependence upon the positions and the inter-pupil distance of the user's eyes.

12. The NR2I display system according to claim 8, wherein the head mounted display comprises:
- a freeform prism lens and a micro-display for projecting image-light onto a first surface of said freeform prism-lens, said image light projecting onto a second surface of said freeform prism-lens performing a first internal reflection to a third surface of the freeform prism-lens, a second internal reflection from the third surface towards a predetermined region of the second surface whereupon the light exits the freeform prism-lens towards the user's eye through said predetermined region; wherein
- external light is prevented from entering the second surface excluding said predetermined region through at least one of an applied coating to the second surface of the freeform prism-lens and opaque structures external to the freeform prism-lens.

13. The NR2I display system according to claim 8, wherein the head mounted display comprises:
- a display assembly with a horizontal track to allow forward and backward movement of the display assembly relative to the user's head;
- a headband with a curved track located at the front-center, containing integral battery compartments used to power the NR2I system;
- a member connecting the horizontal track on the display assembly to the curved track on the headband, said member having a curved structure to mate with the curved track of the headband; wherein
- the display assembly may be translated forward and backward to adjust eye-relief, and moved vertically wherein the display assembly rotates relative to the user's head as moved upwards and downwards independence upon the curved track.

14. The NR2I display system according to claim 8, wherein the head mounted display comprises:
- an optical sensor; and
- at least one micro-shutter of a plurality of micro-shutters.

15. A near-to-eye (NR2I) display system comprising:
a head mounted display; wherein
the head mounted display comprises:
- a left optical assembly comprising a first micro-display disposed in a predetermined position relative to the front of a left eye of a user of the NR2I display and a first optical train to couple the first micro-display to the user's left eye;
- a right optical assembly comprising a second micro-display disposed in a predetermined position relative to the front of a right eye of a user of the NR2I display and a second optical train to couple the second micro-display to the user's right eye; and
- a processor to generate the content to be displayed by the first micro-display and the second micro-display wherein an image to be viewed by the user is split into a first predetermined portion for display by the first micro-display and a second predetermined portion for display by the second micro-display; wherein
a predetermined portion of the first predetermined portion of the image overlaps a predetermined portion of the second predetermined portion of the image such that the user can view a wide field of view.

16. A near-to-eye (NR2I) display system comprising:
a head mounted display; wherein
the head mounted display comprises:
- an assembly comprising a freeform prism lens disposed parallel to a transverse plane of a user and a micro-display for projecting image-light onto a predetermined region of a first surface of said freeform prism-lens, said image light performing two internal reflections within the freeform prism-lens before exiting the freeform prism-lens for viewing by the user with an eye;
- a second assembly comprising a second freeform prism lens disposed parallel to the transverse plane of the user and a second micro-display for projecting image-light onto a predetermined region of a first surface of said second freeform prism-lens, said image light performing two internal reflections within the second freeform prism-lens before exiting the second freeform prism-lens for viewing by the user with their other eye;

an infra-red sensor to image a portion of one of the eye and the other eye, the infra-red sensor receiving infra-red light reflected from the one of the eye and other eye directly from a different face of the one of the freeform prism lens and second freeform prism lens than those proximate the associated one of the micro-display and the second micro-display with the one of the eye and the other eye and that proximate the one of the eye and the other eye with no reflection of infra-red light occurring between the one of the freeform prism lens and second freeform prism lens and the infra-red sensor; and one or more infra-red optical sources; wherein the one or more infra-red sources comprises at least one of:
an optical infra-red source disposed either proximate a different face of the freeform prism lens than that proximate to the micro-display when illuminating the eye of the user or proximate a different face of the second freeform prism lens than that proximate to the second microdisplay when illuminating the other eye of the user;
an optical infra-red source illuminating either the eye of the user directly and not via the freeform prism lens or the other eye of the user directly and not via the second freeform prism lens;
an optical infra-red source coupled via an optical waveguide disposed within either an assembly comprising the freeform prism lens when illuminating the eye of the user or another assembly comprising the second freeform prism lens when illuminating the other eye of the user; and
an optical infra-red source coupled to the user's eye via an optical waveguide formed within either the freeform prism lens when illuminating the eye of the user or the second freeform prism lens when illuminating the other eye of the user;

the micro-display is fixedly held in position by said assembly relative to said first surface of the freeform prism lens and proximate a temple of the user nearest the user's eye viewing the projected image-light, such assembly having attachment features such that vertical angular motion of the assembly across the user's vertical field of view when attached to a body of the NR2I system is made possible, in order to allow positioning of the display above the user's line of sight; and the second micro-display is fixedly held in position relative to said first surface of the second freeform prism lens and proximate the user's other temple by said second assembly, such assembly having attachment features such that lateral motion of the second assembly across the user's horizontal field of view when attached to the body of the NR2I system is made possible allowing the positions and separation of the assembly and second assembly to be established in dependence upon the positions and the inter-pupil distance of the user's eyes.

17. A near-to-eye (NR2I) display system comprising:
a head mounted display; wherein
the head mounted display comprises:
one or more infra-red optical sources to illuminate the user's eye;
a display assembly comprising micro-display and a freeform prism lens (prism) disposed parallel to a transverse plane of a user of the head mounted display with a horizontal track to allow forward and backward movement of the display assembly relative to the user's head;
an infra-red sensor;
a headband with a curved track located at the front-center, containing integral battery compartments used to power the NR2I system; and
a member connecting the horizontal track on the display assembly to the curved track on the headband, said member having a curved structure to mate with the curved track of the headband; wherein
the micro-display is proximate a face of the prism for displaying content to the user of the NR2I system wherein light emitted from the micro-display and received by the prism emerges from the prism and subsequently directly impinges upon the user's eye;
an infra-red sensor to image a portion of the user's eye, the infra-red sensor receiving infra-red light reflected from the user's eye directly from a different face of the prism than that proximate the micro-display and that proximate the user's eye with no reflection of the reflected infra-red light occurring within the prism and the infra-red sensor;
the display assembly may be translated forward and backward to adjust eye-relief and moved vertically wherein the display assembly rotates relative to the user's head as moved upwards and downwards independence upon the curved track; and
the one or more infra-red sources comprises at least one of:
an optical infra-red source disposed proximate a different face of the prism than that proximate to the micro-display;
an optical infra-red source illuminating the user's eye directly and not via the prism;
an optical infra-red source coupled to the user's eye via an optical waveguide disposed within an assembly comprising the prism; and
an optical infra-red source coupled to the user's eye via an optical waveguide formed within the prism.

18. A near-to-eye (NR2I) display system comprising:
a head mounted display; wherein
the head mounted display comprises:
a first assembly comprising at least a pair of temple arms that bear some or all of the weight of an attached display assembly, and a first portion of a hinged attachment to a second assembly;
the second assembly, the second assembly comprising at least a micro-display, an optical train to allow a user to view the image created by the micro-display, an infra-red sensor used to image the user's eye(s), and a second portion of the hinged attachment to the first assembly;
a processing system that determines the direction of a user's preferred retinal location within the displayed image;
an optical train to couple the micro-display to the user's eye and allow the user to view their external environment through the optical train; and a plurality of micro-shutters disposed with respect to the optical train between the external environment and the optical train; wherein the micro-display is disposed in a predetermined position relative to a front of an eye of a user of the NR2I display;

the processing of the users preferred retinal location is performed in dependence upon the angle of the hinged attachment between the two assemblies;

the user can view a synthesized image comprising:
- a first portion provided by one or more display regions of the micro-display; and
- a second portion provided by one or more environment regions of the external environment;

a first subset of the plurality of micro-shutters associated with the one or more display regions are configured to block the external environment; and a second subset of the plurality of micro-shutters associated with the one or more environment regions are configured to pass the external environment.

19. A near-to-eye (NR2I) display system comprising:
a head mounted display; wherein
the head mounted display comprises:
- a first assembly comprising at least a pair of temple arms that bear some or all of the weight of an attached display assembly, and a first portion of a hinged attachment to a second assembly;
- the second assembly, the second assembly comprising at least a micro-display, an optical train to allow a user to view the image created by the micro-display, an infra-red sensor used to image the user's eye(s), and a second portion of the hinged attachment to the first assembly; and
- a processing system that determines the direction of a user's preferred retinal location within the displayed image; wherein the processing of the users preferred retinal location is performed in dependence upon the angle of the hinged attachment between the two assemblies; and the second assembly comprises:
- a left optical assembly comprising a first micro-display disposed in a predetermined position relative to a front of a left eye of a user of the NR2I display and a first optical train to couple the first micro-display to the user's left eye;
- a right optical assembly comprising a second micro-display disposed in a predetermined position relative to a front of a right eye of the user of the NR2I display and a second optical train to couple the second micro-display to the user's right eye;
- a processor to generate the content to be displayed by the first micro-display and the second micro-display wherein an image to be viewed by the user is split into a first predetermined portion for display by the first micro-display and a second predetermined portion for display by the second micro-display; wherein
- a predetermined portion of the first predetermined portion of the image overlaps a predetermined portion of the second predetermined portion of the image such that the user can view a wide field of view.

* * * * *